US009505751B2

(12) United States Patent
Campbell et al.

(10) Patent No.: US 9,505,751 B2
(45) Date of Patent: Nov. 29, 2016

(54) SUBSTITUTED [1,2,4]TRIAZOLO[1,5-A]PYRAZINES AS PHOSPHODIESTERASE INHIBITORS

(71) Applicant: SUNOVION PHARMACEUTICALS INC., Marlborough, MA (US)

(72) Inventors: John Emmerson Campbell, Cambridge, MA (US); Phillip G. Jones, Danvers, MA (US); Scott Malcolm, Southborough, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 14/409,866

(22) PCT Filed: Jun. 19, 2013

(86) PCT No.: PCT/US2013/046483
§ 371 (c)(1),
(2) Date: Dec. 19, 2014

(87) PCT Pub. No.: WO2013/192273
PCT Pub. Date: Dec. 27, 2013

(65) Prior Publication Data
US 2015/0322090 A1    Nov. 12, 2015

Related U.S. Application Data

(60) Provisional application No. 61/661,710, filed on Jun. 19, 2012.

(51) Int. Cl.
| | |
|---|---|
| A61K 31/4985 | (2006.01) |
| C07D 241/38 | (2006.01) |
| C07D 487/04 | (2006.01) |
| C07D 471/04 | (2006.01) |
| A61K 31/437 | (2006.01) |
| A61K 31/4709 | (2006.01) |
| C07D 519/00 | (2006.01) |

(52) U.S. Cl.
CPC ........... *C07D 471/04* (2013.01); *A61K 31/437* (2013.01); *A61K 31/4709* (2013.01); *A61K 31/4985* (2013.01); *C07D 487/04* (2013.01); *C07D 519/00* (2013.01)

(58) Field of Classification Search
CPC ............ A61K 31/4985; C07D 241/38; C07D 487/04
USPC ............ 514/249; 544/350; 548/302.1, 302.7, 548/303.1, 304.4
See application file for complete search history.

(56) References Cited

U.S. PATENT DOCUMENTS

| | | | |
|---|---|---|---|
| 2007/0299079 A1 | 12/2007 | Norbert et al. | |
| 2009/0143391 A1 | 6/2009 | Hofgen et al. | |
| 2011/0178083 A1 | 7/2011 | Ripka et al. | |
| 2013/0150371 A1* | 6/2013 | Chaturvedula | C07D 487/04 514/249 |

FOREIGN PATENT DOCUMENTS

| | | |
|---|---|---|
| WO | WO-2012/065612 A1 | 5/2012 |
| WO | WO-2013/052526 A1 | 4/2013 |

OTHER PUBLICATIONS

Chappie, T. A. et al., Discovery of a series of 6,7-dimethoxy-4-pyrrolidylquinazoline PDE10A inhibitors, J. Med. Chem., 50: 182-185 (2007).
International Search Report for PCT/US2013/046483, 4 pages (Oct. 31, 2013).
Written Opinion for PCT/US2013/046483, 6 pages (Oct. 31, 2013).

* cited by examiner

*Primary Examiner* — Douglas M Willis

(57) ABSTRACT

Provided herein are substituted triazolopyrazine phosphodiesterase inhibitors, and pharmaceutical compositions thereof, useful for the treatment of, for example, central nervous system and metabolic diseases and disorder.

24 Claims, No Drawings

SUBSTITUTED [1,2,4]TRIAZOLO[1,5-A]PYRAZINES AS PHOSPHODIESTERASE INHIBITORS

I. FIELD

Provided herein are heteroaryl compounds useful for treating various disorders or diseases, such as disorders or diseases of the central nervous system and metabolic disorders. Also provided herein are compositions comprising the compounds, and methods of use thereof.

II. BACKGROUND

Central nervous system (CNS) disorders affect a wide range of the population with differing severity. For example, schizophrenia is a psychopathological disorder of unknown origin, which usually appears for the first time in early adulthood and is marked by characteristics, such as, psychotic symptoms, phasic progression and development, and deterioration in social behavior and professional capability. Characteristic psychotic symptoms include disorders of thought content (e.g., multiple, fragmentary, incoherent, implausible or simply delusional contents, or ideas of persecution) and of mentality (e.g., loss of association, flight of imagination, incoherence, or incomprehensibility), as well as disorders of perceptibility (e.g., hallucinations), emotions (e.g., superficial or inadequate emotions), self-perceptions, intentions, impulses, and inter-human relationships, and psychomotoric disorders (e.g., catatonia). Other symptoms are also associated with this disorder. See, e.g., *Diagnostic and Statistical Manual of Mental Disorders*, 4$^{th}$ Ed., American Psychiatric Association (1997) (DSM-IV™).

Schizophrenia can be classified into various subgroups. For example, the paranoid type is characterized by delusions and hallucinations and absence of thought disorder, disorganized behavior, and affective flattening. The disorganized type, also named hebephrenic schizophrenia, is characterized by the presence of both thought disorder and affective flattening. The catatonic type is characterized by prominent psychomotor disturbances, including symptoms of catatonic stupor and waxy flexibility. In the undifferentiated type, psychotic symptoms are present but the criteria for paranoid, disorganized, or catatonic types have not been met.

The symptoms of schizophrenia normally manifest themselves in three broad categories, i.e., positive, negative and cognitive symptoms. Positive symptoms are those that represent an excess of normal experiences, such as hallucinations, disorganized speech, and delusions. Negative symptoms are those where the patient suffers from a lack of normal experiences, such as anhedonia, lack of motivation, inability to experience pleasure, and lack of social interaction. The cognitive symptoms relate to cognitive impairment in schizophrenics, such as lack of sustained attention, impairment of memory, and deficits in decision making. The current anti-psychotics are somewhat effective in treating the positive symptoms but are less effective in treating the negative or cognitive symptoms. For instance, the current typical or atypical anti-psychotics do not address cognitive or negative symptoms of schizophrenia, and only treat the positive symptoms in approximately 40% of patients.

Cognitive impairments include a decline in cognitive functions or cognitive domains, e.g., working memory, attention and vigilance, verbal learning and memory, visual learning and memory, reasoning and problem solving, e.g., executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts, difficulties in integrating thoughts, feelings and behavior, or difficulties in extinction of irrelevant thoughts.

Agitation is a well-recognized behavioral disorder with a range of symptoms, including hostility, extreme excitement, poor impulse control, tension, and uncooperativeness. Agitation is common in the elderly and often associated with dementia such as those caused by Alzheimer's disease, Parkinson's disease, and Huntington's disease, and by diseases that affect blood vessels, such as stroke or multi-infarct dementia, which is caused by multiple strokes in the brain. An estimated five percent of people aged 65 and older and up to 20 percent of those aged 80 and older are affected by dementia. Of these sufferers, nearly half exhibit behavioral disturbances, such as agitation, wandering, and violent outbursts. Agitated behaviors can also be manifested in cognitively intact elderly people and by those with psychiatric disorders other than dementia.

Dementia is characterized by several cognitive impairments including significant memory deficit and can stand alone, or be an underlying characteristic feature of a variety of diseases, including but not limited to, Alzheimer's disease, Parkinson's disease, Huntington's disease, and multiple sclerosis.

Thus, there remains a great need for effective treatments of various CNS disorders.

Cyclic nucleotide phosphodiesterases (PDEs) are a super family of enzymes encoded by twenty-one genes, and are subdivided into eleven known families based on structure and function. PDEs are modular enzymes having a catalytic domain in the C-terminal portion of the protein and regulatory elements in the N-terminal portion. PDEs hydrolyze the phosphodiester bond of cyclic nucleotides, e.g., cyclic adenosine monophosphate (cAMP) and cyclic guanosine monophosphate (cGMP), converting them into the corresponding monophosphates. cAMP and cGMP function as intracellular second messengers regulating a wide range of intracellular processes. For instance, in neurons cAMP and cGMP activate cyclic-nucleotide-dependent kinases and the subsequent phosphorylation of proteins involved in acute regulation of synaptic transmission and in neuronal differentiation and survival. PDEs are therefore important regulators of a wide variety of physiological processes. PDEs are expressed differentially throughout the organism and cyclic nucleotide signaling is highly compartmentalized within individual cells. Thus, different PDE isozymes can serve distinct physiological functions. Compounds that can selectively inhibit distinct PDE families or isozymes may offer additional therapeutic benefits, fewer side effects, or both.

PDE-10 was first reported in 1999 (Soderling et al., *Proc. Natl. Acad. Sci.*, 1999, 96, 7071-76; Loughney et al., *Gene*, 1999, 234, 109-17; Fujishige et al., *J. Biol. Chem.*, 1999, 274, 18438-45). Homology screening revealed mouse PDE-10A as the first member of the PDE-10 family of enzymes. The human PDE-10 sequence is highly homologous to both the rat and mouse PDE-10 enzymes. The PDE-10 family of enzymes has a lower degree of sequence homology as compared to previously identified PDE families. PDE-10 can hydrolyze both cAMP ($K_m$=0.26 µM) and cGMP ($K_m$=7.2 µM), and has a five-fold greater $V_{max}$ for cGMP than for cAMP.

PDE-10A is primarily expressed in the brain, also found in testes. PDE-10A mRNA and protein are abundant in brain tissues, and are mainly detected at high levels in the medium spiny neurons (MSN) of the striatum, a distribution conserved across mammalian species. The striatal MSNs provide input to the basal ganglia circuit, affecting action selection and execution, and suppressing undesired responses to sensory stimuli. PDE-10A has become an emerging target for the development of new anti-psychotics. Inhibitors of PDE-10A have been shown to increase cAMP and cGMP levels in striatal tissue and have demonstrated efficacy against not only positive but also negative and cognitive symptoms in animal models of schizophrenia. PDE-10A is also useful in treating metabolic disorders, such as diabetes, obesity, and metabolic syndrome.

Citation of any references in this Section of the application is not to be construed as an admission that such reference is prior art to the present application.

III. SUMMARY

Provided herein are compounds of formula (I), or pharmaceutically acceptable salts or stereoisomers thereof:

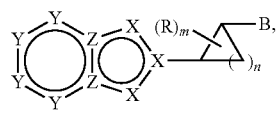

(I)

wherein X, Y, Z, R, B, m, and n are defined herein elsewhere. The compounds are useful for treating various diseases or disorders, such as CNS disorders and metabolic disorders.

Also provided herein are compositions and dosage forms comprising, a compound provided herein, and one or more pharmaceutically acceptable excipient(s). Compositions and dosage forms provided herein may further comprise one or more additional active ingredients.

Also provided herein are methods for the treatment, prevention, and/or management of various disorders, such as a CNS disorder or a metabolic disorder, e.g., the treatment, prevention, and/or amelioration of one or more symptoms of a disorder, using the compounds and compositions provided herein. In one embodiment, the disorders provided herein include, but are not limited to, schizophrenia, psychosis, cognitive disorders, mood disorders, attention deficit disorders, and neurodegenerative diseases. In one embodiment, the disorders include, but are not limited to, neurological disorder, schizophrenia, schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia.

In one embodiment, provided herein is a method of treating, preventing, and/or managing schizophrenia or related disorders, including but not limited to, schizoaffective disorder, schizophreniform disorder, paraphrenia, paranoid personality disorder, schizoid personality disorder, and schizotypal personality disorder; a disease having a psychosis component, including but not limited to, Alzheimer's psychosis, Parkinson's psychosis, shared psychotic disorder, and substance-induced psychotic disorder; cognitive impairment, including but not limited to, cognitive impairment associated with schizophrenia, cognitive deficit in Alzheimer's disease, and cognitive deficit in Parkinson's disease; mood disorder, including but not limited to, bipolar disorder; attention deficit disorder, including but not limited to attention deficit hyperactive disorder; neurodegenerative disease, including but not limited to, Huntington's disease; or depression, including but not limited to, major depressive disorder, unipolar depression, and treatment resistant depression. In one embodiment, provided herein is a method of treating, preventing, and/or managing a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, provided herein is a method of treating, preventing, and/or ameliorating one or more symptoms associated with a disorder provided herein elsewhere (e.g., a CNS disorder or a metabolic disorder), in a subject, such as a mammal, e.g., human, rodent (e.g., mice and rats), cat, dog, and non-human primate, among others. In one embodiment, the method comprises contacting a compound provided herein with a PDE enzyme. In one embodiment, the method comprises contacting a compound provided herein with a PDE enzyme expressed in the central nervous system. In one embodiment, the method comprises contacting a compound provided herein with PDE-10A. In one embodiment, the method comprises contacting a cell with a compound provided herein. In an exemplary embodiment, the cell is a brain cell, such as, e.g., a MSN cell, a neuronal cell, or a glial cell.

IV. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may be optionally substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere. In some embodiments, the alkenyl is optionally substituted with one or more halo.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere. In some embodiments, the alkynyl is optionally substituted with one or more halo.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere. In some embodiments, the cycloalkyl is optionally substituted with one or more halo.

As used herein, and unless otherwise specified, the term "heteroalkyl" refers to a stable straight or branched chain, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms can be consecutive, such as, for example, —$CH_2$—NH—O—$CH_3$ and —$CH_2$—O—Si($CH_3$)$_3$. In certain embodiments, the heteroalkyl is optionally substituted as described herein elsewhere. In some embodiments, the heteroalkyl is optionally substituted with one or more halo.

As used herein, and unless otherwise specified, the term "alkoxyl" or "alkoxy" refers to a stable straight or branched chain, or cyclic hydrocarbon radical, or combinations thereof, consisting of the stated number of carbon atoms and from one or more, in one embodiment, one to three, O atoms, wherein at least one O atom is at the position where the alkoxyl or alkoxy group is attached to the remainder of the molecule. Examples of alkoxyl include, but are not limited to, —O—$CH_3$, —O—$CF_3$, —O—$CH_2$—$CH_3$, —O—$CH_2$—$CH_2$—$CH_3$, —O—CH—($CH_3$)$_2$, and —O—$CH_2$—$CH_2$—O—$CH_3$. In one embodiment, the alkoxyl is optionally substituted as described herein elsewhere. In some embodiments, the alkoxyl is optionally substituted with one or more halo.

As used herein, and unless otherwise specified, the term "aminoalkyl" or "alkylamino" refers to a stable straight or branched chain, or cyclic hydrocarbon radical, or combinations thereof, consisting of the stated number of carbon atoms and from one or more, in one embodiment, one to three, N atoms, wherein at least one N atom is at the position where the aminoalkyl or alkylamino group is attached to the remainder of the molecule. Examples of aminoalkyl include, but are not limited to, —NH—$CH_3$, —N($CH_3$)$_2$, —NH—$CH_2$—$CH_3$, —N($CH_3$)—$CH_2$—$CH_3$, —NH—CH—($CH_3$)$_2$, and —NH—$CH_2$—$CH_2$—N($CH_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. An example of aralkyl includes, but is not limited to, benzyl. In certain embodiments, both alkyl and aryl may be optionally substituted with one or more substituents as described herein elsewhere.

As used herein, and unless otherwise specified, the term "heteroarylalkyl" or "heteroaralkyl" refers to a monovalent alkyl group substituted with heteroaryl. In certain embodiments, both alkyl and heteroaryl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzopyranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1H$), deuterium ($^2H$), tritium ($^3H$), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (=O), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^1$; or (iii) R$^b$ and R$^c$ together with the N atom to which they are attached form heteroaryl or heterocyclyl, optionally substituted with one or more, in one embodiment, one, two, three, or four, substituents Q$^1$. As used herein, all groups that can be substituted are "optionally substituted," unless otherwise specified.

In one embodiment, each Q$^1$ is independently selected from the group consisting of (a) cyano, halo, oxo, and nitro; and (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, depression (e.g., major depressive disorder, dysthymia, and bipolar depressive disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder.

As used herein, and unless otherwise specified, the terms "psychosis," "schizophrenia," "obsessive-compulsive disorder," "substance abuse," "anxiety," "eating disorders," "migraine," and other CNS disorders described herein elsewhere are used herein in a manner consistent with their accepted meanings in the art. See, e.g., *Diagnostic and Statistical Manual of Mental Disorders*, 4th Ed., American Psychiatric Association (1997) (DSM-IV™).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4th Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD), dysthymia, and treatment resistant depression. "Major depressive disorder" is used herein interchangeably with "unipolar depression" and "major depression." "Depression" may also include any condition commonly associated with depression, such as all forms of fatigue (e.g., chronic fatigue syndrome) and cognitive deficits.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (See, e.g., *Harrison's Principles of Internal Medicine*, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the terms "overweight" and "obese" refer to adult persons 18 years or older having a greater than ideal body weight (e.g., greater than ideal body fat) that can be measured by the body mass index (BMI), which is generally correlated with total body fat and the relative risk of suffering from premature death or disability due to diseases as a consequence of the overweight or obese condition. BMI is calculated by weight in kilograms divided by height in meters squared (kg/m$^2$), or alternatively by weight in pounds, multiplied by 703, divided by height in inches squared (lbs×703/in$^2$). Overweight individuals typically have a BMI of between about 25 and about 29, whereas obese individuals typically have a BMI of about 30 or more (see, e.g., National Heart, Lung, and Blood Institute, Clinical Guidelines on the Identification, Evaluation, and Treatment of Overweight and Obesity in Adults, The Evidence Report, Washington, D.C., U.S. Department of Health and Human Services, NIH publication no. 98-4083, 1998). Other means for indicating excess body weight, excess body fat, and obesity include direct measure of body fat and/or waist-to-hip ratio measurements.

As used herein, and unless otherwise specified, the term "metabolic syndrome" is used according to its usual meaning in the art. The American Heart Association characterizes metabolic syndrome as having at least three or more of the following symptoms: 1) elevated waist circumference [>102 cm (40 inches) in men; >88 cm (35 inches) in women]; 2) elevated triglycerides [≥150 mg/dL (>1.695 mmol/L) or drug treatment for elevated triglycerides]; 3) reduced HDL cholesterol [<40 mg/dL (1.036 mmol/L) in men; <50 mg/dL (1.295 mmol/L) in women; or drug treatment for reduced HDL-C]; 4) elevated blood pressure [≥130/85 mmHg or drug treatment for hypertension]; and 5) elevated fasting glucose [≥110 mg/dL or drug treatment for elevated glucose]. According to the World Health Organization, metabolic syndrome includes individuals suffering from diabetes, impaired glucose tolerance, impaired fasting glucose, or insulin resistance plus two or more of the following symptoms: 1) high blood pressure [≥160/90 mmHg]; 2) hyperlipdemia [triglyceride concentration ≥150 mg/dL (1.695 mmol/L) and/or HDL cholesterol <35 mg/dL (0.9 mmol/L) in men and <39 mg/dL (1.0 mmol/L) in women]; 3) central obesity [waist-to-hip ratio of >0.90 for men and >0.85 for women and/or BMI >30 kg/m$^2$]; and 4) microalbuminuria [urinary albumin excretion rate ≥20 μg/min or an albumin-to-creatinine ratio ≥20 mg/kg).

B. Compounds

In one embodiment, provided herein is a compound of formula (I):

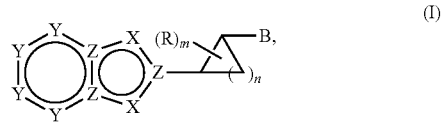

or a pharmaceutically acceptable salt or stereoisomer thereof, wherein n is 1, 2, or 3;

m is 0, 1, 2, 3, 4, 5, 6, 7, or 8; provided that (i) when n is 1, m is 0, 1, 2, 3, or 4; (ii) when n is 2, m is 0, 1, 2, 3, 4, 5, or 6; and (iii) when n is 3, m is 0, 1, 2, 3, 4, 5, 6, 7, or 8;

each R is independently halo or (C$_1$-C$_4$)alkyl;

each X is independently N, CR$^1$, O, or NR$^2$;

each Z is independently N or C;

each Y is independently N or CR$^3$;

provided that

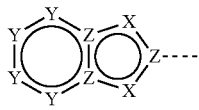

contains 1, 2, 3, 4, or 5 nitrogen ring atoms;

$R^1$ is hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl;

$R^2$ is hydrogen, alkyl, alkenyl, heteroalkyl, cycloalkyl, aryl, heteroaryl, heterocyclyl, carbonyl, or sulfonyl;

each $R^3$ is independently (i) hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl; or (ii) two adjacent occurrences of $R^3$ together with the carbon atoms to which they are attached form an aryl, heteroaryl, cycloalkyl, or heterocyclyl ring;

B is

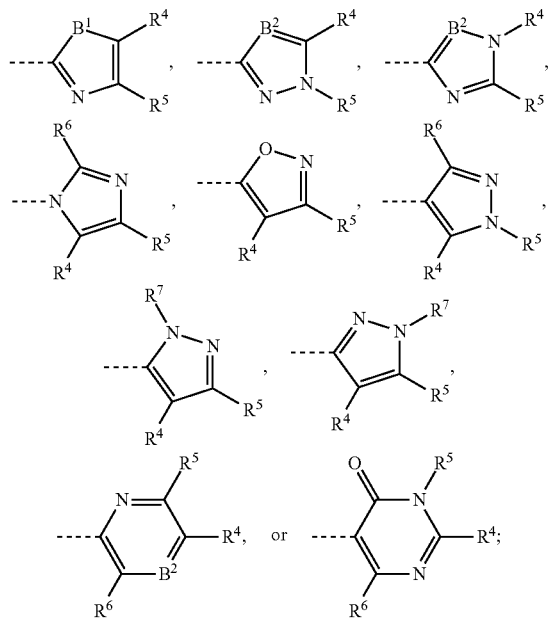

(i) $R^4$ and $R^5$ together with the atoms to which they are attached form a monocyclic or multicyclic aryl, heteroaryl, cycloalkyl, or heterocyclyl ring; or (ii) $R^4$ and $R^5$ are each independently hydrogen, cyano, halo, alkyl, alkenyl, alkoxyl, aminoalkyl, heteroalkyl, cycloalkyl, aralkyl, heteroaralkyl, aryl, heteroaryl, heterocyclyl, hydroxyl, amino, imino, amido, carbonyl, thiol, sulfinyl, or sulfonyl;

$B^1$ is O, S, or $NR^8$;

$B^2$ is $CR^9$ or N;

$R^6$ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;

$R^7$ is hydrogen, alkyl, alkenyl, heteroalkyl, cycloalkyl, aryl, heteroaryl, heterocyclyl, carbonyl, or sulfonyl;

$R^8$ is hydrogen, alkyl, alkenyl, heteroalkyl, cycloalkyl, aryl, heteroaryl, heterocyclyl, carbonyl, or sulfonyl; and $R^9$ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;

provided that a compound of formula (I) is not:

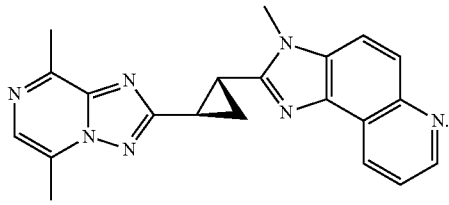 [SMILES: Cc1ncc(C)n2nc([C@@H]3C[C@H]3c3nc4c5cccnc5ccc4n3C)nc12]

In one embodiment, provided herein is a compound of formula (I-A):

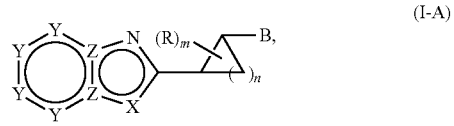

(I-A)

or a pharmaceutically acceptable salt or stereoisomer thereof, wherein n is 1, 2, or 3;

m is 0, 1, 2, 3, 4, 5, 6, 7, or 8; provided that (i) when n is 1, m is 0, 1, 2, 3, or 4; (ii) when n is 2, m is 0, 1, 2, 3, 4, 5, or 6; and (iii) when n is 3, m is 0, 1, 2, 3, 4, 5, 6, 7, or 8;

each R is independently halo or $(C_1-C_4)$alkyl;

X is (i) N or $CR^1$; or (ii) O or $NR^2$;

each Z is independently N or C;

each Y is independently N or $CR^3$;

provided that

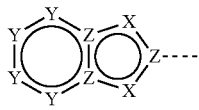

contains 1, 2, 3, 4, or 5 nitrogen ring atoms;

$R^1$ is hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl;

$R^2$ is hydrogen, alkyl, alkenyl, heteroalkyl, cycloalkyl, aryl, heteroaryl, heterocyclyl, carbonyl, or sulfonyl;

each $R^3$ is independently (i) hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl; or (ii) two adjacent occurrences of $R^3$ together with the carbon atoms to which they are attached form an aryl, heteroaryl, cycloalkyl, or heterocyclyl ring;

B is

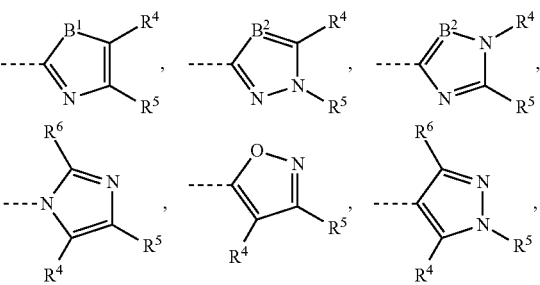

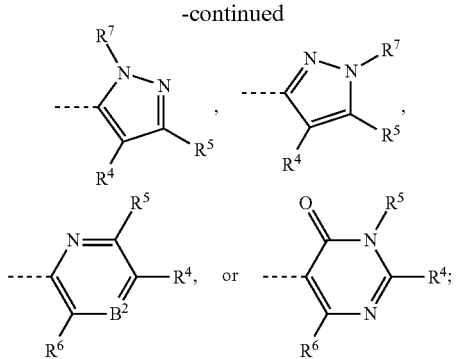

(i) $R^4$ and $R^5$ together with the atoms to which they are attached form a monocyclic or multicyclic aryl, heteroaryl, cycloalkyl, or heterocyclyl ring; or (ii) $R^4$ and $R^5$ are each independently hydrogen, cyano, halo, alkyl, alkenyl, alkoxyl, aminoalkyl, heteroalkyl, cycloalkyl, aralkyl, heteroaralkyl, aryl, heteroaryl, heterocyclyl, hydroxyl, amino, imino, amido, carbonyl, thiol, sulfinyl, or sulfonyl;

$B^1$ is O, S, or $NR^8$;

$B^2$ is $CR^9$ or N;

$R^6$ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;

$R^7$ is hydrogen, alkyl, alkenyl, heteroalkyl, cycloalkyl, aryl, heteroaryl, heterocyclyl, carbonyl, or sulfonyl;

$R^8$ is hydrogen, alkyl, alkenyl, heteroalkyl, cycloalkyl, aryl, heteroaryl, heterocyclyl, carbonyl, or sulfonyl; and $R^9$ is hydrogen, halo, cyano, alkyl, alkenyl, alkoxyl, aminoalkyl, heteroalkyl, cycloalkyl, aralkyl, heteroaralkyl, aryl, heteroaryl, heterocyclyl, amino, amido, carbonyl, thiol, sulfinyl, or sulfonyl;

provided that a compound of formula (I) is not:

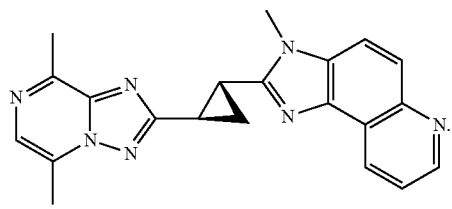 [SMILES: Cc1ncc(C)n2nc([C@@H]3C[C@H]3c3nc4c5cccnc5ccc4n3C)nc12]

In one embodiment, n is 1. In one embodiment, n is 2. In one embodiment, n is 3. In one embodiment, n is 1 or 2.

In one embodiment, m is 0. In one embodiment, m is 1. In one embodiment, m is 2. In one embodiment, m is 3. In one embodiment, m is 4. In one embodiment, m is 5. In one embodiment, m is 6. In one embodiment, m is 7. In one embodiment, m is 8. In one embodiment, m is 1 or 2.

In one embodiment, provided herein is a compound of the following formulae:

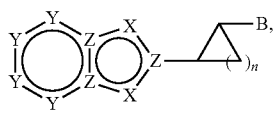 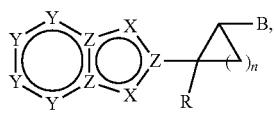

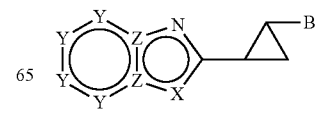 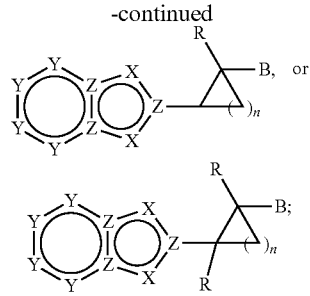

or a pharmaceutically acceptable salt or stereoisomer thereof, wherein X, Y, Z, n, B, and R are defined herein.

In one embodiment, provided herein is a compound of the following formulae:

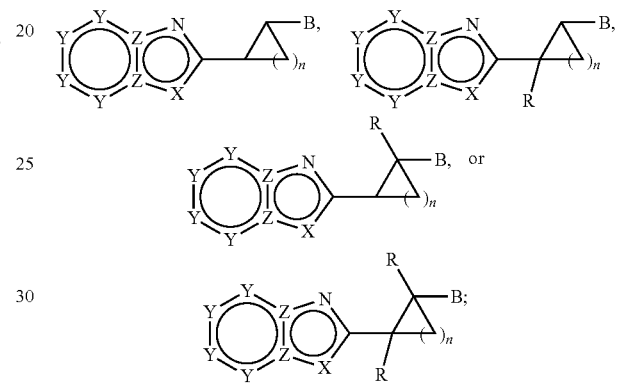

or a pharmaceutically acceptable salt or stereoisomer thereof, wherein X, Y, Z, n, B, and R are defined herein.

In one embodiment, provided herein is a compound of the following formulae:

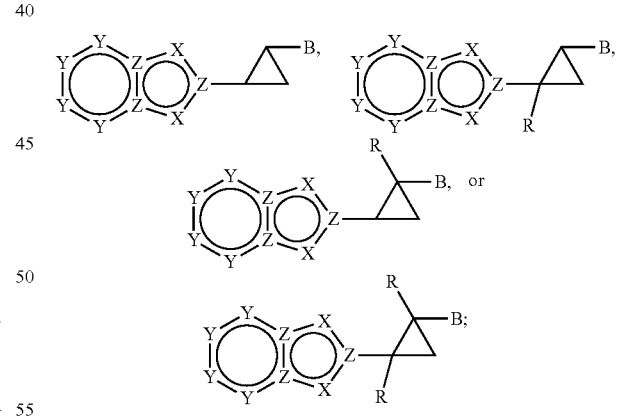

or a pharmaceutically acceptable salt or stereoisomer thereof, wherein X, Y, Z, B, and R are defined herein.

In one embodiment, provided herein is a compound of the following formulae:

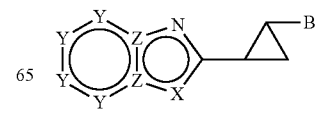 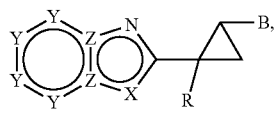

-continued

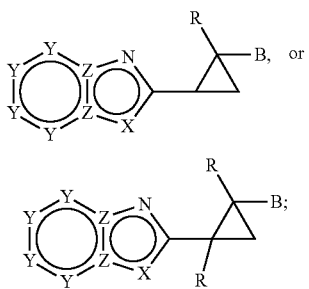

or a pharmaceutically acceptable salt or stereoisomer thereof, wherein X, Y, Z, B, and R are defined herein.

In one embodiment, provided herein is a compound of the following formulae:

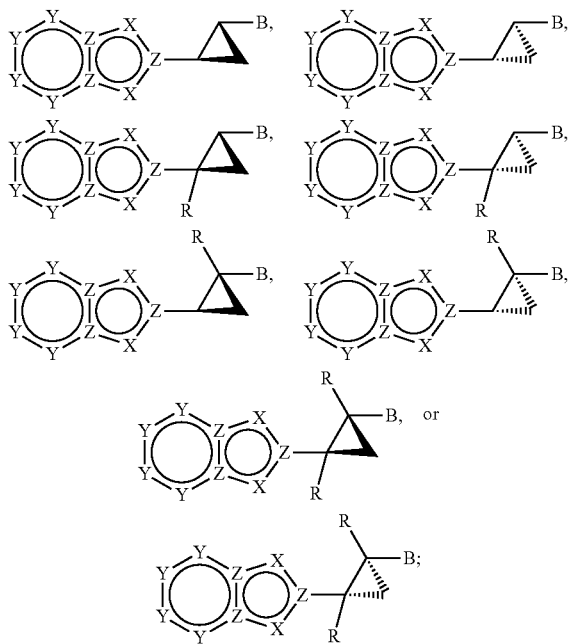

or a pharmaceutically acceptable salt or stereoisomer thereof, wherein X, Y, Z, B, and R are defined herein.

In one embodiment, provided herein is a compound of the following formulae:

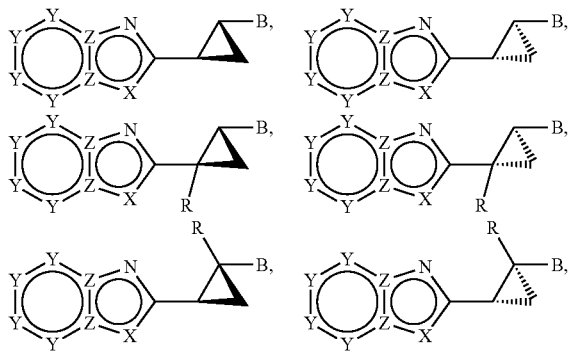

-continued

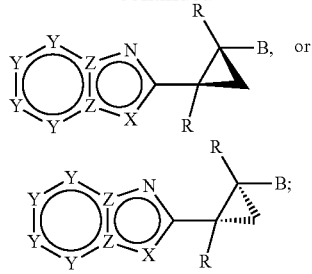

or a pharmaceutically acceptable salt or stereoisomer thereof, wherein X, Y, Z, B, and R are defined herein.

In one embodiment, R is halo (e.g., F, Cl, or Br). In one embodiment, R is $(C_1-C_4)$alkyl (e.g., Me, Et, Pr, or Bu, including optionally substituted Me, Et, Pr, or Bu). In one embodiment, R is methyl.

In one embodiment, X is N. In one embodiment, X is $CR^1$. In one embodiment, X is O. In one embodiment, X is $NR^2$. In one embodiment, X is $CR^1$ or N. In one embodiment, X is O or $NR^2$.

In one embodiment, Z is N. In one embodiment, Z is C. One occurrence of Z may be the same or different from another occurrence of Z.

In one embodiment, in a compound of formula (I), all occurrences of Z are C. In one embodiment, at least one occurrence of Z is C. In one embodiment, at least two occurrences of Z are C. In one embodiment, all occurrences of Z are N. In one embodiment, at least one occurrence of Z is N. In one embodiment, at least two occurrences of Z are N. In one embodiment, one occurrences of Z is C and the other two occurrences of Z are N. In one embodiment, one occurrences of Z is N and the other two occurrences of Z are C.

In one embodiment, in a compound of formula (I-a), two occurrences of Z are N. In one embodiment, two occurrences of Z are C. In one embodiment, one occurrence of Z is N and the other occurrence of Z is C. In one embodiment, at least one of the occurrences of Z is N. In one embodiment, at least one of the occurrences of Z is C.

In one embodiment, Y is N. In one embodiment, Y is $CR^3$. One occurrence of Y may be the same or different from another occurrence of Y.

In one embodiment, $R^1$ is hydrogen. In one embodiment, $R^1$ is halo. In one embodiment, $R^1$ is cyano. In one embodiment, $R^1$ is alkyl. In one embodiment, $R^1$ is alkenyl. In one embodiment, $R^1$ is alkoxyl. In one embodiment, $R^1$ is aminoalkyl. In one embodiment, $R^1$ is heteroalkyl. In one embodiment, $R^1$ is cycloalkyl. In one embodiment, $R^1$ is aryl. In one embodiment, $R^1$ is heteroaryl. In one embodiment, $R^1$ is heterocyclyl. In one embodiment, $R^1$ is amino. In one embodiment, $R^1$ is amido. In one embodiment, $R^1$ is carbonyl. In one embodiment, $R^1$ is thiol. In one embodiment, $R^1$ is sulfinyl. In one embodiment, $R^1$ is sulfonyl. Each $R^1$ is optionally substituted.

In one embodiment, $R^2$ is hydrogen. In one embodiment, $R^2$ is alkyl. In one embodiment, $R^2$ is alkenyl. In one embodiment, $R^2$ is heteroalkyl. In one embodiment, $R^2$ is cycloalkyl. In one embodiment, $R^2$ is aryl. In one embodiment, $R^2$ is heteroaryl. In one embodiment, $R^2$ is heterocyclyl. In one embodiment, $R^2$ is carbonyl. In one embodiment, $R^2$ is sulfonyl. Each $R^2$ is optionally substituted.

In one embodiment, $R^3$ is hydrogen. In one embodiment, $R^3$ is halo. In one embodiment, $R^3$ is cyano. In one embodiment, $R^3$ is alkyl. In one embodiment, $R^3$ is alkenyl. In one embodiment, R³ is alkoxyl. In one embodiment, R³ is aminoalkyl. In one embodiment, R³ is heteroalkyl. In one embodiment, R³ is cycloalkyl. In one embodiment, R³ is aryl. In one embodiment, R³ is heteroaryl. In one embodiment, R³ is heterocyclyl. In one embodiment, R³ is amino. In one embodiment, R³ is amido. In one embodiment, R³ is carbonyl. In one embodiment, R³ is thiol. In one embodiment, R³ is sulfinyl. In one embodiment, R³ is sulfonyl. In one embodiment, each R³ is independently hydrogen, halo, cyano, alkyl, alkenyl, alkoxyl, aminoalkyl, heteroalkyl, cycloalkyl, aryl, heteroaryl, heterocyclyl, amino, amido, carbonyl, thiol, sulfinyl, or sulfonyl. In one embodiment, two adjacent occurrences of R³ together with the carbon atoms to which they are attached form an aryl ring. In one embodiment, two adjacent occurrences of R³ together with the carbon atoms to which they are attached form a heteroaryl ring. In one embodiment, two adjacent occurrences of R³ together with the carbon atoms to which they are attached form a cycloalkyl ring. In one embodiment, two adjacent occurrences of R³ together with the carbon atoms to which they are attached form a heterocyclyl ring. Each R³ is optionally substituted.

In one embodiment, two occurrences of R³ together with the atoms to which they are attached form an aryl, heteroaryl, cycloalkyl, or heterocyclyl ring, including but not limited to, an optionally substituted phenyl, pyridyl, pyrimidyl, pyrazinyl, pyridazinyl, imidazolyl, thienyl, or thiazolyl, or a 5- or 6-membered heterocyclyl ring. In one embodiment, two adjacent occurrences of R³ together with the atoms to which they are attached form an aryl or heteroaryl ring, including but not limited to, an optionally substituted phenyl, pyridyl, pyrimidyl, pyrazinyl, pyridazinyl, imidazolyl, thienyl, or thiazolyl. In one embodiment, two adjacent occurrences of R³ together with the atoms to which they are attached form an optionally substituted pyridyl.

In one embodiment, B is

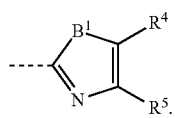

In one embodiment, B is

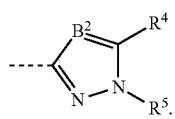

In one embodiment, B is

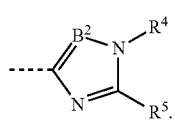

In one embodiment, B is

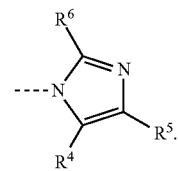

In one embodiment, B is

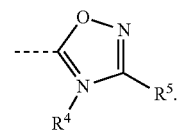

In one embodiment, B is

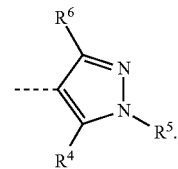

In one embodiment, B is

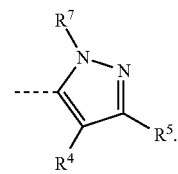

In one embodiment, B is

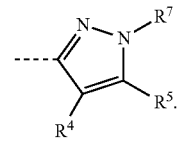

In one embodiment, B is

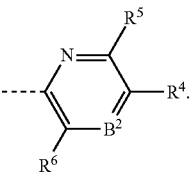

In one embodiment, B is

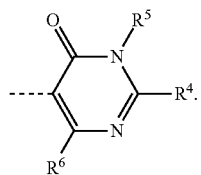

In one embodiment, B is

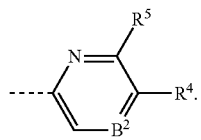

In one embodiment, B is

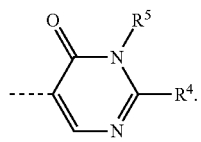

In one embodiment, $R^4$ and $R^5$ are each independently hydrogen, cyano, halo, alkyl, alkenyl, alkoxyl, aminoalkyl, heteroalkyl, cycloalkyl, aralkyl, heteroaralkyl, aryl, heteroaryl, heterocyclyl, hydroxyl, amino, imino, amido, carbonyl, thiol, sulfinyl, or sulfonyl.

In one embodiment, $R^4$ is hydrogen. In one embodiment, $R^4$ is cyano. In one embodiment, $R^4$ is halo. In one embodiment, $R^4$ is alkyl. In one embodiment, $R^4$ is alkenyl. In one embodiment, $R^4$ is alkoxyl. In one embodiment, $R^4$ is aminoalkyl. In one embodiment, $R^4$ is heteroalkyl. In one embodiment, $R^4$ is cycloalkyl. In one embodiment, $R^4$ is aralkyl. In one embodiment, $R^4$ is heteroaralkyl. In one embodiment, $R^4$ is aryl. In one embodiment, $R^4$ is heteroaryl. In one embodiment, $R^4$ is heterocyclyl. In one embodiment, $R^4$ is hydroxyl. In one embodiment, $R^4$ is amino. In one embodiment, $R^4$ is imino. In one embodiment, $R^4$ is amido. In one embodiment, $R^4$ is carbonyl. In one embodiment, $R^4$ is thiol. In one embodiment, $R^4$ is sulfinyl. In one embodiment, $R^4$ is sulfonyl.

In one embodiment, $R^5$ is hydrogen. In one embodiment, $R^5$ is cyano. In one embodiment, $R^5$ is halo. In one embodiment, $R^5$ is alkyl. In one embodiment, $R^5$ is alkenyl. In one embodiment, $R^5$ is alkoxyl. In one embodiment, $R^5$ is aminoalkyl. In one embodiment, $R^5$ is heteroalkyl. In one embodiment, $R^5$ is cycloalkyl. In one embodiment, $R^5$ is aralkyl. In one embodiment, $R^5$ is heteroaralkyl. In one embodiment, $R^5$ is aryl. In one embodiment, $R^5$ is heteroaryl. In one embodiment, $R^5$ is heterocyclyl. In one embodiment, $R^5$ is hydroxyl. In one embodiment, $R^5$ is amino. In one embodiment, $R^5$ is imino. In one embodiment, $R^5$ is amido. In one embodiment, $R^5$ is carbonyl. In one embodiment, $R^5$ is thiol. In one embodiment, $R^5$ is sulfinyl. In one embodiment, $R^5$ is sulfonyl.

In one embodiment, $R^4$ and $R^5$ together form a monocyclic ring and B is a bicyclic ring system. In one embodiment, $R^4$ and $R^5$ together form a multicyclic ring and B is a tricyclic ring system.

In one embodiment, $R^4$ and $R^5$ together with the atoms to which they are attached form a monocyclic aryl ring. In one embodiment, $R^4$ and $R^5$ together with the atoms to which they are attached form a multicyclic aryl ring. In one embodiment, $R^4$ and $R^5$ together with the atoms to which they are attached form a monocyclic heteroaryl ring. In one embodiment, $R^4$ and $R^5$ together with the atoms to which they are attached form a multicyclic heteroaryl ring. In one embodiment, $R^4$ and $R^5$ together with the atoms to which they are attached form a monocyclic cycloalkyl ring. In one embodiment, $R^4$ and $R^5$ together with the atoms to which they are attached form a multicyclic cycloalkyl ring. In one embodiment, $R^4$ and $R^5$ together with the atoms to which they are attached form a monocyclic heterocyclyl ring. In one embodiment, $R^4$ and $R^5$ together with the atoms to which they are attached form a multicyclic heterocyclyl ring. Each monocyclic or multicyclic aryl, heteroaryl, cycloalkyl, or heterocyclyl ring is optionally substituted.

In one embodiment, $R^4$ and $R^5$ together with the atoms to which they are attached form a 6-membered aromatic ring (e.g., aryl or heteroaryl ring), including but not limited to, phenyl ring, pyridyl ring, pyrimidyl ring, pyrazine ring, or pyridazine ring, each of which is optionally substituted.

In one embodiment, $R^4$ and $R^5$ together with the atoms to which they are attached form an aryl, heteroaryl, cycloalkyl, or heterocyclyl ring, including but not limited to, an optionally substituted phenyl, pyridyl, pyrimidyl, pyrazinyl, pyridazinyl, imidazolyl, thienyl, or thiazolyl, or a 5- or 6-membered heterocyclyl ring.

In one embodiment, $B^1$ is O. In one embodiment, $B^1$ is S. In one embodiment, $B^1$ is $NR^8$.

In one embodiment, $B^2$ is $CR^9$. In one embodiment, $B^2$ is N.

In one embodiment, $R^6$ is hydrogen. In one embodiment, $R^6$ is halo. In one embodiment, $R^6$ is cyano. In one embodiment, $R^6$ is alkyl. In one embodiment, $R^6$ is alkenyl. In one embodiment, $R^6$ is alkoxyl. In one embodiment, $R^6$ is aminoalkyl. In one embodiment, $R^6$ is heteroalkyl. In one embodiment, $R^6$ is cycloalkyl. In one embodiment, $R^6$ is aralkyl. In one embodiment, $R^6$ is heteroaralkyl. In one embodiment, $R^6$ is aryl. In one embodiment, $R^6$ is heteroaryl. In one embodiment, $R^6$ is heterocyclyl. In one embodiment, $R^6$ is amino. In one embodiment, $R^6$ is amido. In one embodiment, $R^6$ is carbonyl. In one embodiment, $R^6$ is thiol. In one embodiment, $R^6$ is sulfinyl. In one embodiment, $R^6$ is sulfonyl. Each $R^6$ is optionally substituted.

In one embodiment, $R^7$ is hydrogen. In one embodiment, $R^7$ is alkyl. In one embodiment, $R^7$ is alkenyl. In one embodiment, $R^7$ is heteroalkyl. In one embodiment, $R^7$ is cycloalkyl. In one embodiment, $R^7$ is aryl. In one embodiment, $R^7$ is heteroaryl. In one embodiment, $R^7$ is heterocyclyl. In one embodiment, $R^7$ is carbonyl. In one embodiment, $R^7$ is sulfonyl. Each $R^7$ is optionally substituted.

In one embodiment, $R^8$ is hydrogen. In one embodiment, $R^8$ is alkyl. In one embodiment, $R^8$ is alkenyl. In one embodiment, $R^8$ is heteroalkyl. In one embodiment, $R^8$ is cycloalkyl. In one embodiment, $R^8$ is aryl. In one embodiment, $R^8$ is heteroaryl. In one embodiment, $R^8$ is heterocyclyl. In one embodiment, $R^8$ is carbonyl. In one embodiment, $R^8$ is sulfonyl. Each $R^8$ is optionally substituted.

In one embodiment, $R^9$ is hydrogen. In one embodiment, $R^9$ is halo. In one embodiment, $R^9$ is cyano. In one embodiment, $R^9$ is alkyl. In one embodiment, $R^9$ is alkenyl. In one embodiment, $R^9$ is alkoxyl. In one embodiment, $R^9$ is aminoalkyl. In one embodiment, $R^9$ is heteroalkyl. In one embodiment, $R^9$ is cycloalkyl. In one embodiment, $R^9$ is aralkyl. In one embodiment, $R^9$ is heteroaralkyl. In one embodiment, $R^9$ is aryl. In one embodiment, $R^9$ is heteroaryl. In one embodiment, $R^9$ is heterocyclyl. In one embodiment, $R^9$ is amino. In one embodiment, $R^9$ is amido. In one embodiment, $R^9$ is carbonyl. In one embodiment, $R^9$ is thiol. In one embodiment, $R^9$ is sulfinyl. In one embodiment, $R^9$ is sulfonyl. Each $R^9$ is optionally substituted.

In one embodiment,

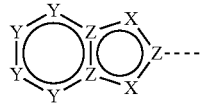

contains from 1 to 2, from 1 to 3, from 1 to 4, from 1 to 5, from 2 to 3, from 2 to 4, from 2 to 5, from 3 to 4, from 3 to 5, or from 4 to 5 nitrogen ring atoms. In one embodiment,

contains one nitrogen ring atom. In one embodiment,

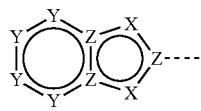

contains two nitrogen ring atoms. In one embodiment,

contains three nitrogen ring atoms. In one embodiment,

contains four nitrogen ring atoms. In one embodiment,

contains five nitrogen ring atoms.

In one embodiment,

contains from 1 to 2, from 1 to 3, from 1 to 4, from 1 to 5, from 2 to 3, from 2 to 4, from 9 to 5 from 3 to 4 from 3 to 5 or from 4 to 5 nitrogen ring atoms. In one embodiment,

contains one nitrogen ring atom. In one embodiment,

contains two nitrogen ring atoms. In one embodiment,

contains three nitrogen ring atoms. In one embodiment,

contains four nitrogen ring atoms. In one embodiment,

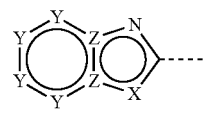

contains five nitrogen ring atoms.

In one embodiment,

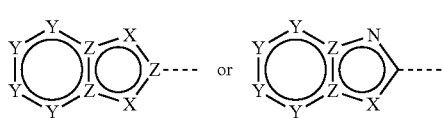

is a bicyclic ring (i.e., when two or more occurrences of Y are $CR^3$, two adjacent occurrences of $R^3$ do not form a ring).

In one embodiment,

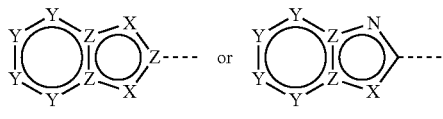

is a tricyclic ring (i.e., when two or more occurrences of Y are $CR^3$, two adjacent occurrences of $R^3$ form a monocyclic ring).

In one embodiment,

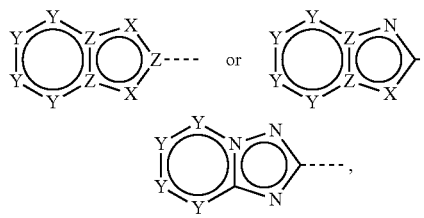

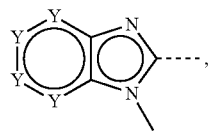

wherein Y is defined herein elsewhere.

In one embodiment,

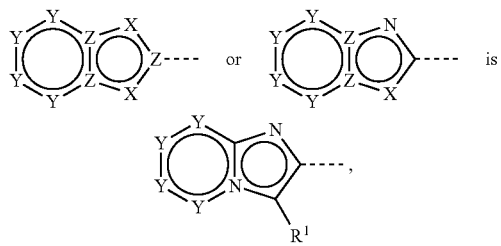

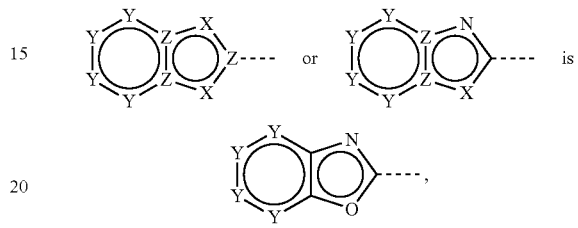

wherein Y is defined herein elsewhere.

In one embodiment, wherein Y and R¹ are defined herein elsewhere.

In one embodiment,

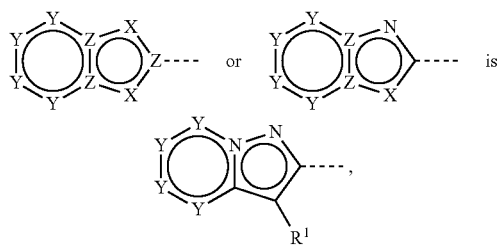

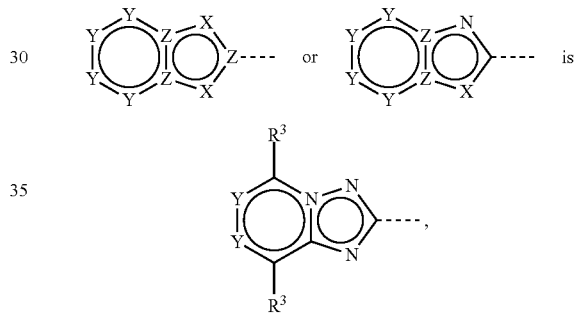

wherein Y and R¹ are defined herein elsewhere.

In one embodiment, R¹ is H, halo, cyano, methyl, ethyl, or CF₃.

In one embodiment, wherein R³ and Y are defined herein elsewhere.

In one embodiment,

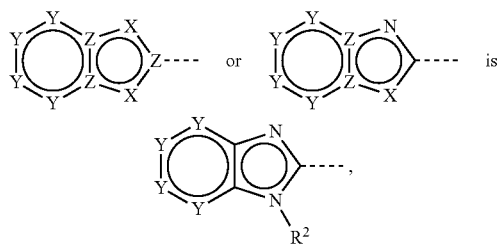

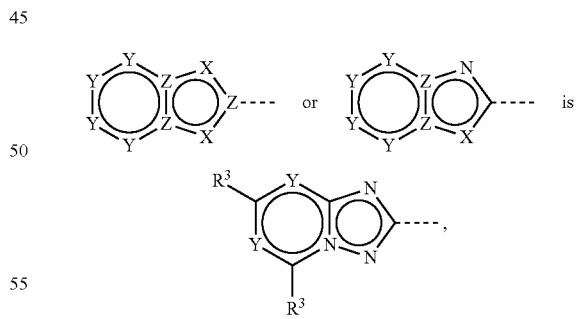

wherein Y and R² are defined herein elsewhere.

In one embodiment, wherein R³ and Y are defined herein elsewhere.

In one embodiment,

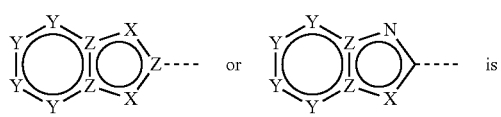

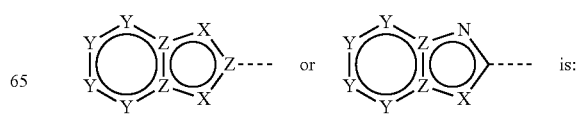

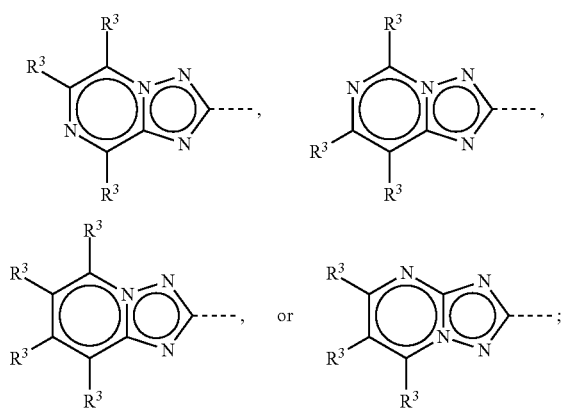
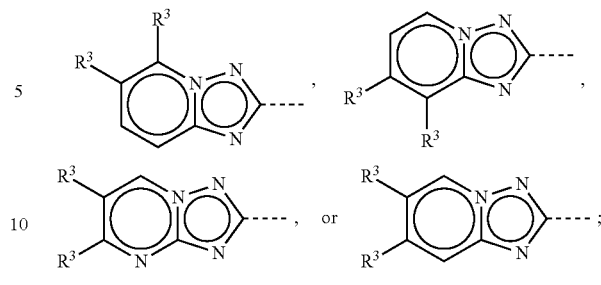
wherein R³ is defined herein elsewhere.
In one embodiment,
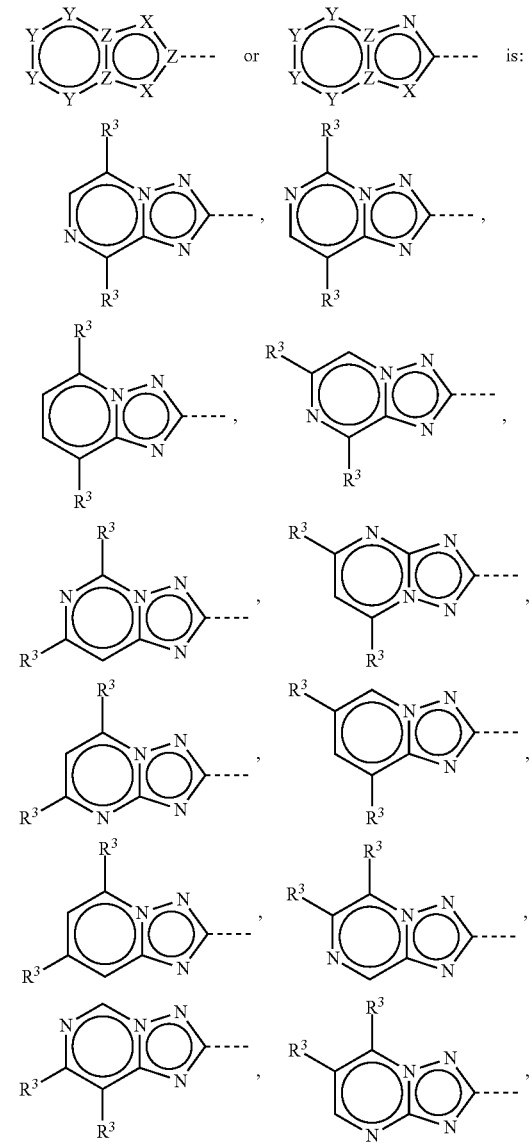
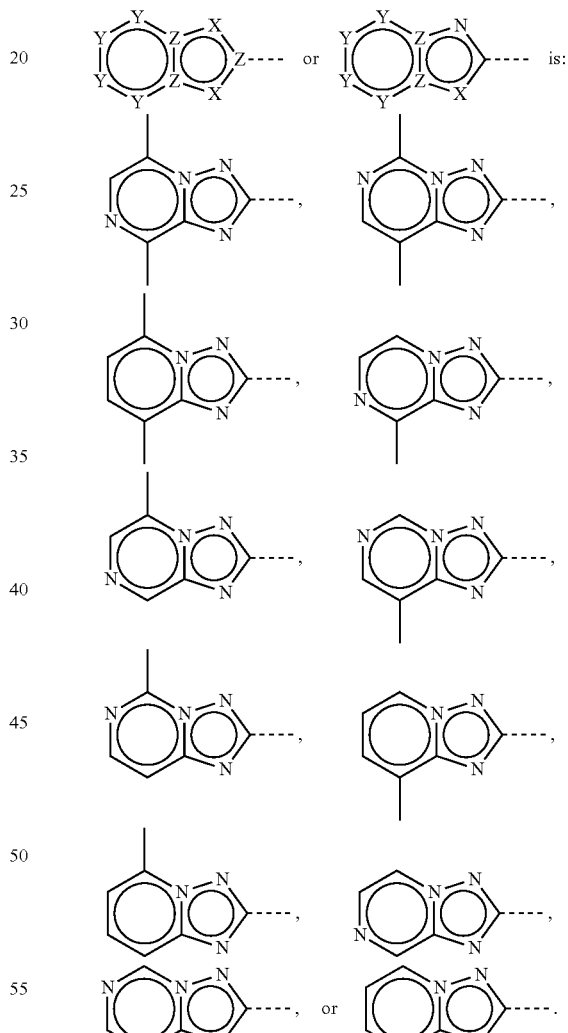
In one embodiment,
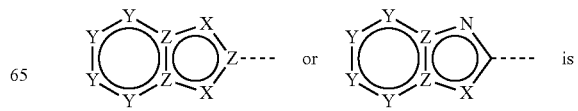

-continued
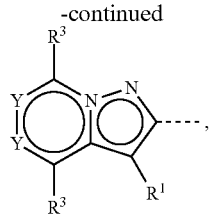
wherein R[1], R[3], and Y are defined herein elsewhere.
In one embodiment,
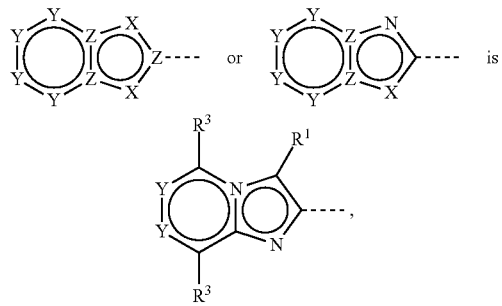
wherein R[1], R[3], and Y are defined herein elsewhere.
In one embodiment.
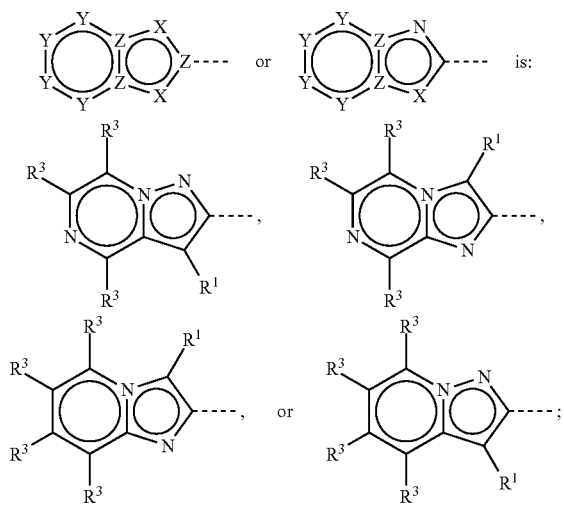
wherein R[1] and R[3] are defined herein elsewhere.
In one embodiment,
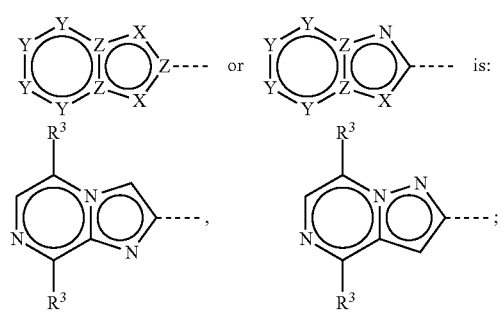
-continued
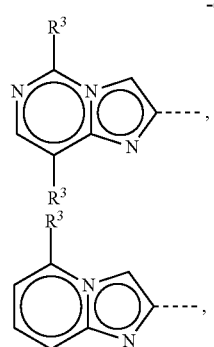
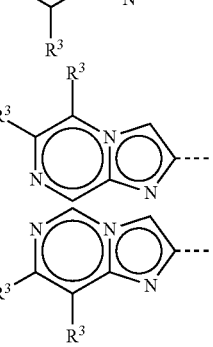
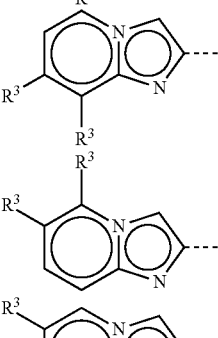
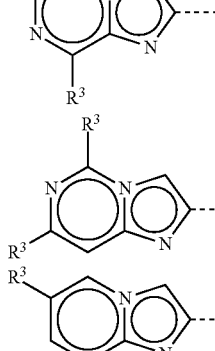
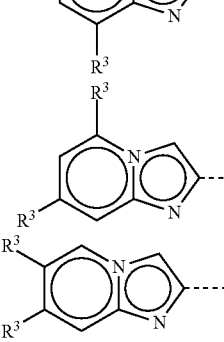
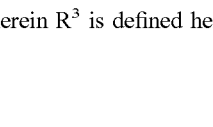
wherein R[3] is defined herein elsewhere.

In one embodiment,
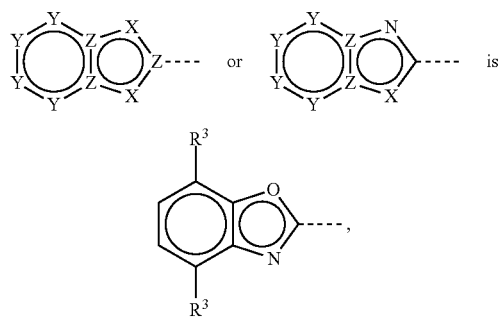
wherein R³ is defined herein elsewhere.
In one embodiment,
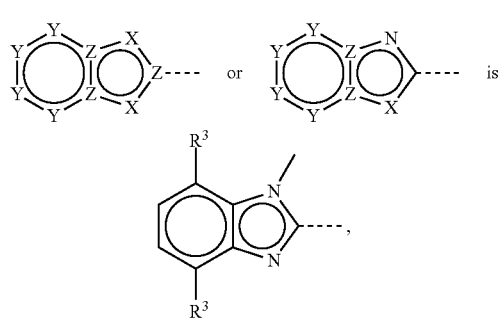
wherein R³ is defined herein elsewhere.
In one embodiment,
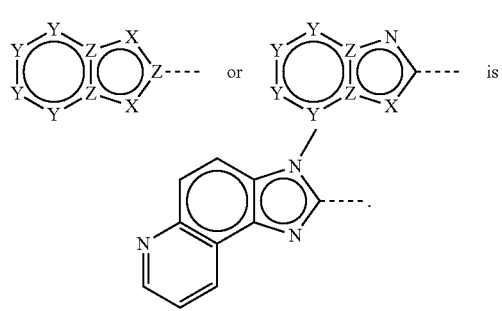
In one embodiment,
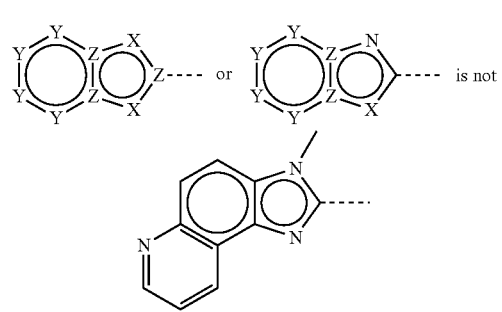
In one embodiment,
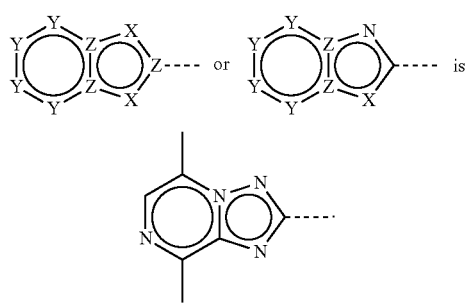
In one embodiment,
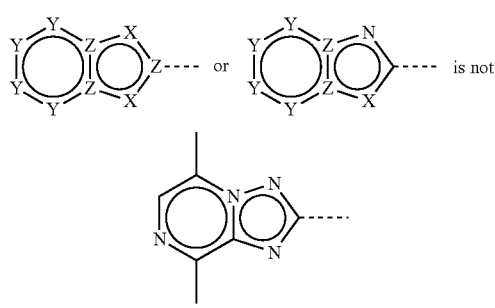 is not
In one embodiment,
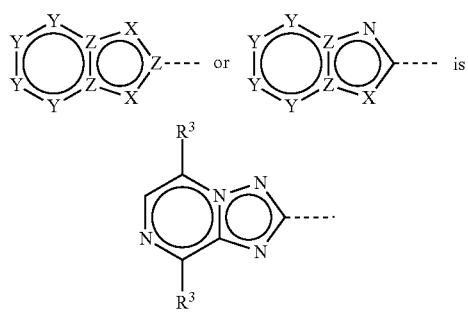
In one embodiment, R³ is methyl.
In one embodiment,
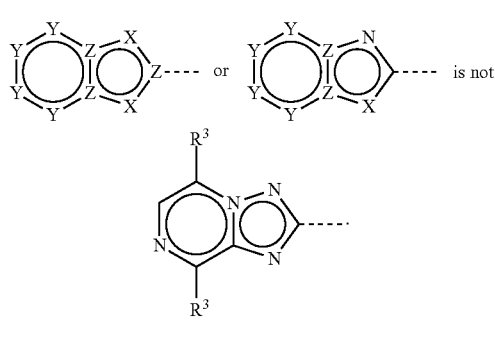 is not
In one embodiment, R³ is not methyl.

In one embodiment,

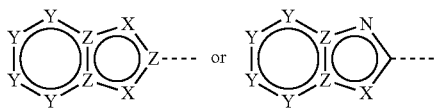

is optionally substituted with up to three substituents. In one embodiment, up to three occurrences of $R^3$ substituting

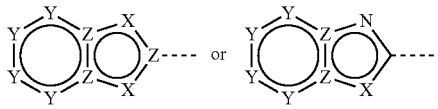

are not hydrogen.

In one embodiment, $R^1$ is hydrogen, halo, cyano, $(C_1-C_6)$alkyl, $(C_1-C_6)$alkoxyl, $(C_1-C_6)$aminoalkyl, $(C_1-C_6)$heteroalkyl, cycloalkyl, aryl, or heteroaryl. In one embodiment, $R^1$ is hydrogen, halo, cyano, $(C_1-C_6)$alkyl, $(C_1-C_6)$alkoxyl, $(C_1-C_6)$aminoalkyl, or $(C_1-C_6)$heteroalkyl. In one embodiment, $R^1$ is H, halo, cyano, methyl, or $CF_3$. In one embodiment, $R^1$ is H or methyl.

In one embodiment, $R^2$ is hydrogen, $(C_1-C_6)$alkyl, $(C_1-C_6)$alkoxyl, $(C_1-C_6)$aminoalkyl, $(C_1-C_6)$heteroalkyl, cycloalkyl, aryl, or heteroaryl. In one embodiment, $R^2$ is hydrogen, $(C_1-C_6)$alkyl, $(C_1-C_6)$alkoxyl, $(C_1-C_6)$aminoalkyl, or $(C_1-C_6)$heteroalkyl. In one embodiment, $R^2$ is H, methyl, or ethyl. In one embodiment, $R^2$ is H or methyl.

In one embodiment, each $R^3$ is independently hydrogen, halo, cyano, $(C_1-C_6)$alkyl, $(C_1-C_6)$alkoxyl, $(C_1-C_6)$aminoalkyl, $(C_1-C_6)$heteroalkyl, cycloalkyl, aryl, or heteroaryl. In one embodiment, each $R^3$ is independently hydrogen, halo, cyano, $(C_1-C_6)$alkyl, $(C_1-C_6)$alkoxyl, or 3- to 6-membered cycloalkyl. In one embodiment, each $R^3$ is independently hydrogen, halo (e.g., F, Cl, or Br), cyano, methyl, ethyl, methoxyl, ethoxyl, $CF_3$, $OCF_3$, or cyclopropyl. In one embodiment, each $R^3$ is independently hydrogen, F, Cl, cyano, methyl, ethyl, methoxyl, ethoxyl, $CF_3$, $OCF_3$, or cyclopropyl. In one embodiment, each $R^3$ is independently hydrogen, F, Cl, methyl, ethyl, $CF_3$, methoxyl, or cyclopropyl. In one embodiment, each $R^3$ is independently hydrogen, methyl, ethyl, chloro, or $CF_3$. In one embodiment, each $R^3$ is independently H, halo (e.g., F or Cl), cyano, methyl, $CF_3$, methoxyl, $OCF_3$, or cyclopropyl. In one embodiment, each $R^3$ is independently hydrogen, methyl, ethyl, $CF_3$, or halo. In one embodiment, each $R^3$ is independently hydrogen, Cl, methyl, or $CF_3$. In one embodiment, each $R^3$ is independently hydrogen or methyl. In one embodiment, two adjacent occurrences of $R^3$ together with the atoms to which they are attached form a 5- or 6-membered aryl to heteroaryl ring (e.g., optionally substituted benzene or pyridine). In one embodiment, two adjacent occurrences of $R^3$ do not form a ring.

In one embodiment, B is

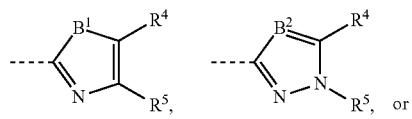

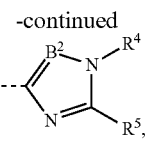

wherein $B^1$, $B^2$, $R^4$, and $R^5$ are defined herein elsewhere.

In one embodiment, $B^1$ is $NR^8$ and $B^2$ is $CR^9$ or N.
In one embodiment, $B^1$ is NH or $NCH_3$. In one embodiment, $B^2$ is CH or N.

In one embodiment, B is a bicyclic ring. In one embodiment, B is a tricyclic ring.

In one embodiment, B contains from 1 to 6, from 1 to 5, from 1 to 4, from 2 to 6, from 2 to 5, from 2 to 4, from 2 to 3, from 3 to 4, or from 3 to 5 nitrogen ring atoms. In one embodiment, B contains one nitrogen ring atom. In one embodiment, B contains two nitrogen ring atoms. In one embodiment, B contains three nitrogen ring atoms. In one embodiment, B contains four nitrogen ring atoms. In one embodiment, B contains five nitrogen ring atoms. In one embodiment, B contains six nitrogen ring atoms.

In one embodiment, B is optionally substituted with up to one, up to two, up to three, up to four, up to five, or up to six substituents. In one embodiment, B is optionally substituted with one or more halo, cyano, methyl, ethyl, $CF_3$, methoxyl, ethoxyl, $OCF_3$, or cyclopropyl.

In one embodiment, B is a bicyclic ring system.

In one embodiment, B is:

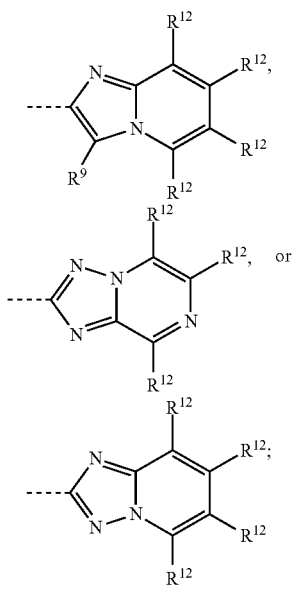

wherein $R^9$ is defined herein elsewhere; and each $R^{12}$ is independently hydrogen, halogen, cyano, =O, —$OR^{13}$, —$NR^{13}R^{14}$, —$N(R^{13})$, —$C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring. In other embodiments, $R^{12}$ is defined herein elsewhere.

In one embodiment, B is

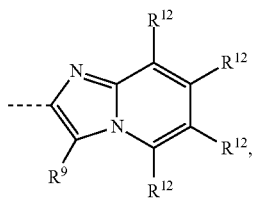

wherein $R^9$ and $R^{12}$ are defined herein elsewhere.

In one embodiment, B is

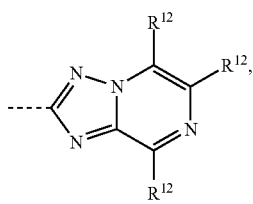

wherein $R^{12}$ is defined herein elsewhere.

In one embodiment, B is

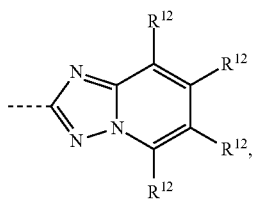

wherein $R^{12}$ is defined herein elsewhere.

In one embodiment, $R^9$ is hydrogen, halo, cyano, ($C_1$-$C_6$)alkyl, ($C_1$-$C_6$)alkoxyl, ($C_1$-$C_6$)aminoalkyl, ($C_1$-$C_6$)heteroalkyl, cycloalkyl, aryl, or heteroaryl. In one embodiment, $R^9$ is hydrogen, halo, cyano, ($C_1$-$C_6$)alkyl, ($C_1$-$C_6$)alkoxyl, or 3- to 6-membered cycloalkyl. In one embodiment, $R^9$ is hydrogen, halo (e.g., F, Cl, or Br), cyano, methyl, ethyl, methoxyl, ethoxyl, $CF_3$, $OCF_3$, or cyclopropyl. In one embodiment, $R^9$ is hydrogen, F, Cl, cyano, methyl, ethyl, methoxyl, ethoxyl, $CF_3$, $OCF_3$, or cyclopropyl. In one embodiment, $R^9$ is hydrogen, F, Cl, methyl, ethyl, $CF_3$, methoxyl, or cyclopropyl. In one embodiment, $R^9$ is hydrogen, methyl, ethyl, chloro, or $CF_3$. In one embodiment, $R^9$ is H, halo (e.g., F or Cl), cyano, methyl, $CF_3$, methoxyl, $OCF_3$, or cyclopropyl. In one embodiment, $R^9$ is hydrogen, F, Cl, methyl, or $CF_3$. In one embodiment, $R^9$ is hydrogen or methyl.

In one embodiment, each $R^{12}$ is independently hydrogen, halo, cyano, ($C_1$-$C_6$)alkyl, ($C_1$-$C_6$)alkoxyl, ($C_1$-$C_6$)aminoalkyl, ($C_1$-$C_6$)heteroalkyl, cycloalkyl, aryl, heteroaryl, or heterocyclyl. In one embodiment, each $R^{12}$ is independently hydrogen, halo, cyano, ($C_1$-$C_6$)alkyl, ($C_1$-$C_6$)alkoxyl, or 3- to 6-membered cycloalkyl. In one embodiment, each $R^{12}$ is independently hydrogen, halo (e.g., F, Cl, or Br), cyano, methyl, ethyl, methoxyl, ethoxyl, $CF_3$, $OCF_3$, or cyclopropyl. In one embodiment, each $R^{12}$ is independently hydrogen, F, Cl, cyano, methyl, ethyl, methoxyl, ethoxyl, $CF_3$, $OCF_3$, or cyclopropyl. In one embodiment, each $R^{12}$ is independently hydrogen, F, Cl, methyl, ethyl, $CF_3$, methoxyl, or cyclopropyl. In one embodiment, each $R^{12}$ is independently hydrogen, methyl, ethyl, chloro, or $CF_3$. In one embodiment, each $R^{12}$ is independently H, halo (e.g., F or Cl), cyano, methyl, $CF_3$, methoxyl, $OCF_3$, or cyclopropyl. In one embodiment, each $R^{12}$ is independently hydrogen, Cl, methyl, or $CF_3$. In one embodiment, each $R^{12}$ is independently hydrogen or methyl.

In one embodiment, B is a tricyclic ring system.
In one embodiment, B is:

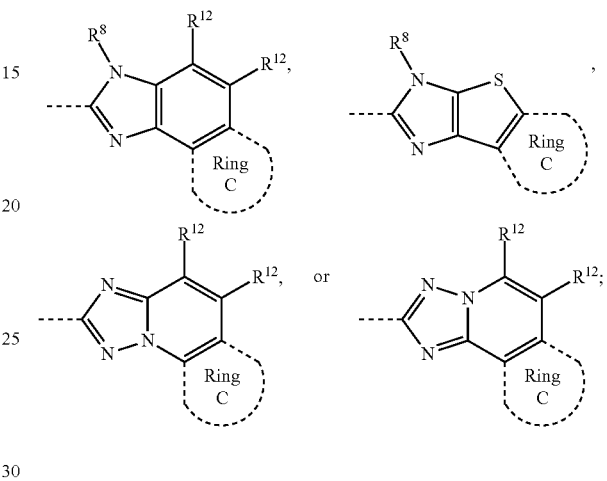

wherein $R^8$ is defined herein elsewhere; each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring; and Ring C is a 5- or 6-membered heteroaryl ring or a 5- to 7-membered cycloalkyl or heterocyclyl ring. In other embodiments, $R^{12}$ is defined herein elsewhere. In one embodiment, Ring C is a 5- or 6-membered heteroaryl ring (e.g., an optionally substituted pyridine, pyrimidine, pyrazine, pyridazine, thiophene, furan, pyrrole, imidazole, pyrazole, oxazole, isoxazole, thiazole, or isothiazole ring). In another embodiment, Ring C is a 5- to 7-membered cycloalkyl or heterocyclyl ring (e.g., an optionally substituted cyclohexene or dihydrofuran ring). In some embodiments, the heterocyclyl ring contains one to two heteroatom(s) independently selected from N, O, and S. In yet another embodiment, Ring C is a 6-membered aryl ring (e.g., an optionally substituted benzene ring). In one embodiment, Ring C is optionally substituted with one or more $R^{12}$, wherein $R^{12}$ is defined herein elsewhere. In specific embodiments, $R^8$ is hydrogen or methyl. In specific embodiments, $R^{12}$ is hydrogen.

In one embodiment, B is:

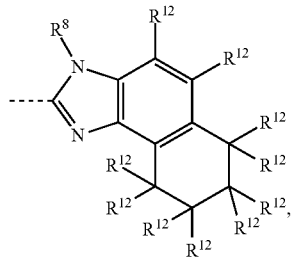

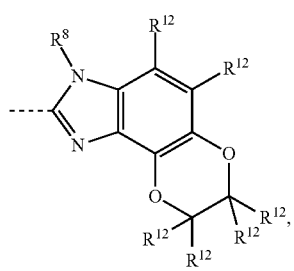

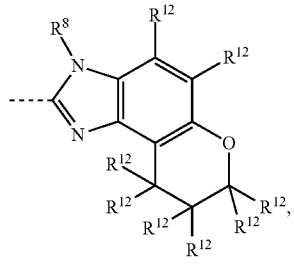

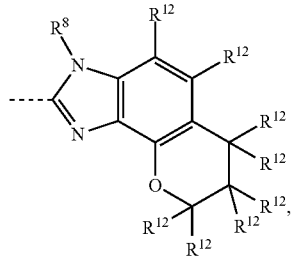

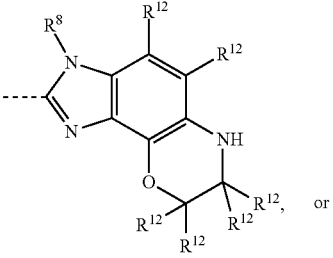

or

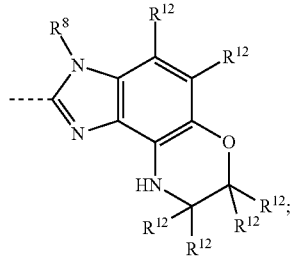

wherein R⁸ and R¹² are defined herein elsewhere.

In one embodiment, B is:

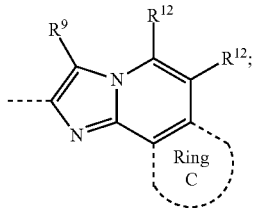

wherein $R^9$ is defined herein elsewhere; each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring; and Ring C is a 5- or 6-membered heteroaryl ring or a 5- to 7-membered cycloalkyl or heterocyclyl ring. In other embodiments, $R^{12}$ is defined herein elsewhere. In one embodiment, Ring C is a 5- or 6-membered heteroaryl ring (e.g., an optionally substituted pyridine, pyrimidine, pyrazine, pyridazine, thiophene, furan, pyrrole, imidazole, pyrazole, oxazole, isoxazole, thiazole, or isothiazole ring). In another embodiment, Ring C is a 5- to 7-membered cycloalkyl or heterocyclyl ring (e.g., an optionally substituted cyclohexene or dihydrofuran ring). In some embodiments, the heterocyclyl ring contains one to two heteroatom(s) independently selected from N, O, and S. In yet another embodiment, Ring C is a 6-membered aryl ring (e.g., an optionally substituted benzene ring). In one embodiment, Ring C is optionally substituted with one or more $R^{12}$, wherein $R^{12}$ is defined herein elsewhere. In specific embodiments, $R^9$ is hydrogen or methyl. In specific embodiments, $R^{12}$ is hydrogen.

In one embodiment, B is:

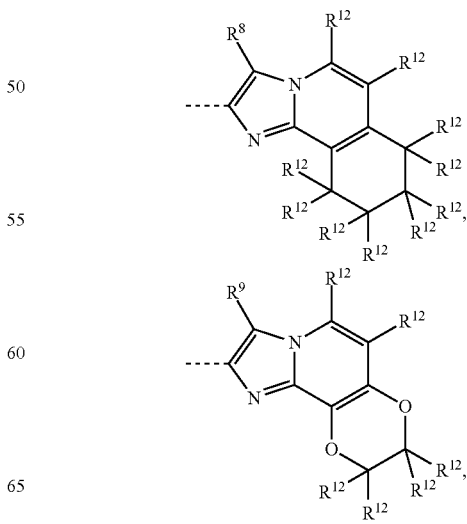

-continued

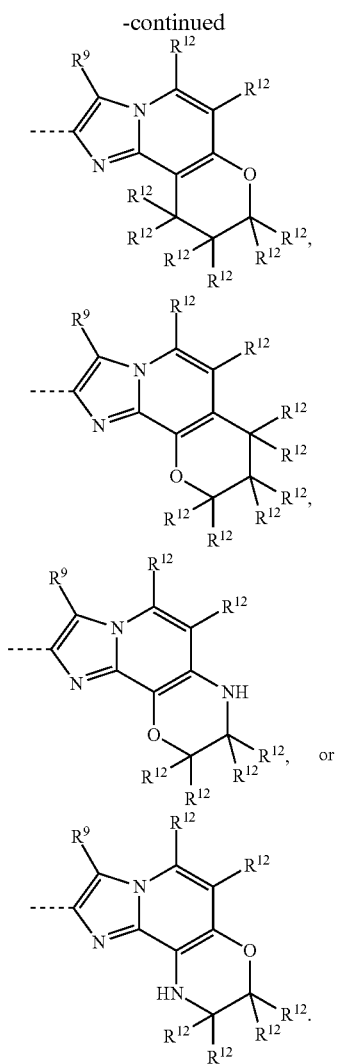

wherein $R^9$ and $R^{12}$ are defined herein elsewhere.

In one embodiment, B is:

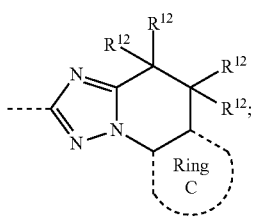

wherein each $R^{12}$ is independently hydrogen, halogen, cyano, =O, —$OR^{13}$, —$NR^{13}R^{14}$, —$N(R^{13})C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$, alkyl, heteroalkyl, cycloalkyl, aralkyl, heteroaralkyl, aryl, heteroaryl, or heterocyclyl; wherein each $R^{13}$ and $R^{14}$ is independently hydrogen, alkyl, heteroalkyl, cycloalkyl, aralkyl, heteroaralkyl, aryl, heteroaryl, or heterocyclyl; or when $R^{13}$ and $R^{14}$ are both attached to one nitrogen atom, $R^{13}$ and $R^{14}$ together with the nitrogen atom to which they are attached form a 3 to 10 membered ring; and Ring C is a 5- or 6-membered heteroaryl ring, a 5- to 7-membered cycloalkyl or heterocyclyl ring, or a 6-membered aryl ring. In other embodiments, $R^{12}$ is defined herein elsewhere. In one embodiment, Ring C is optionally substituted with one or more $R^{12}$, wherein $R^{12}$ is defined herein elsewhere.

In one embodiment, B is:

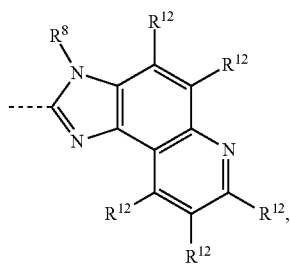

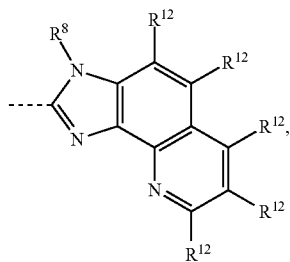

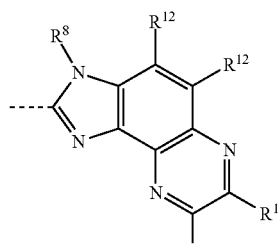 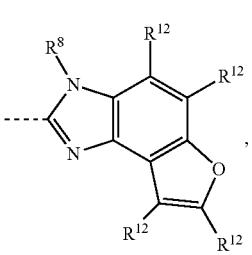

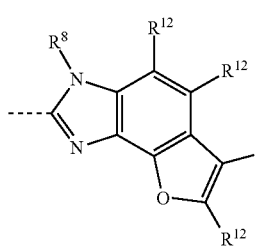 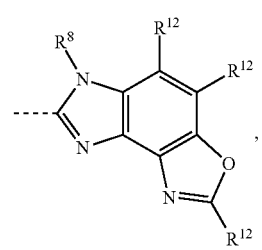

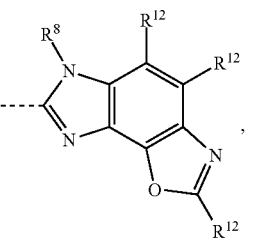 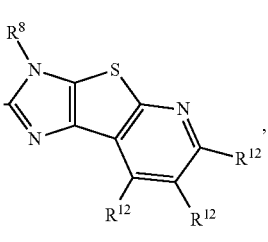

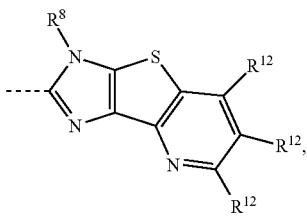

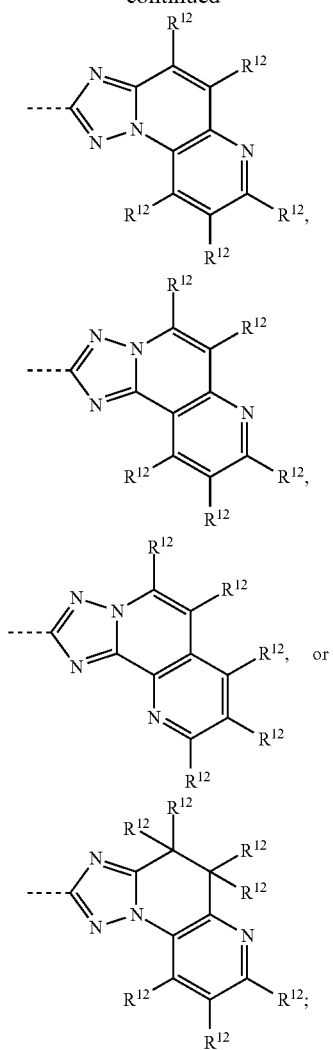
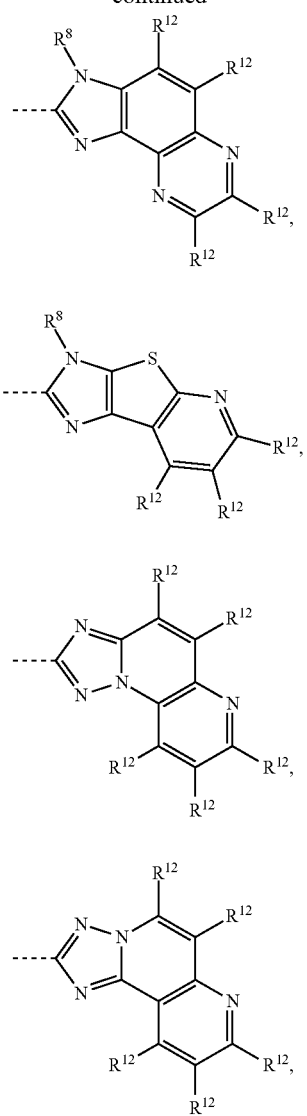
wherein R[8] and R[12] are defined herein elsewhere.
In one embodiment, B is:
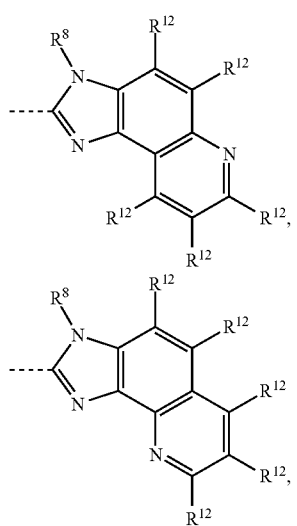
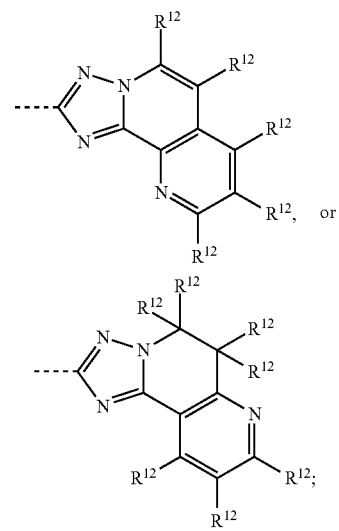
wherein R[8] and R[12] are defined herein elsewhere.

In one embodiment, B is:

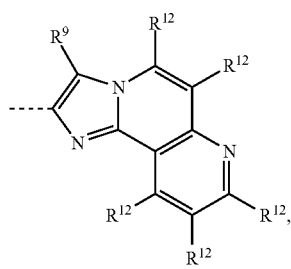

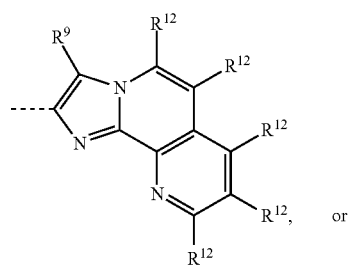

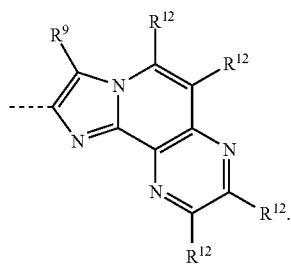

wherein $R^9$ and $R^{12}$ are defined herein elsewhere.

In one embodiment, $R^6$ is hydrogen, halo, cyano, or alkyl. In one embodiment, $R^6$ is hydrogen, halo, cyano, or $(C_1$-$C_4)$alkyl (e.g., methyl or ethyl). In one embodiment, $R^6$ is hydrogen, halo, or $(C_1$-$C_4)$alkyl (e.g., methyl or ethyl). In one embodiment, $R^6$ is hydrogen or $(C_1$-$C_4)$alkyl (e.g., methyl or ethyl). In one embodiment, $R^6$ is hydrogen or methyl.

In one embodiment, $R^7$ is hydrogen or alkyl. In one embodiment, $R^7$ is hydrogen or $(C_1$-$C_4)$alkyl (e.g., methyl or ethyl). In one embodiment, $R^7$ is hydrogen or methyl.

In one embodiment, $R^8$ is hydrogen or alkyl. In one embodiment, $R^8$ is hydrogen or $(C_1$-$C_4)$alkyl (e.g., methyl or ethyl). In one embodiment, $R^8$ is hydrogen or methyl.

In one embodiment, each $R^{12}$ is independently hydrogen, halo, cyano, alkyl, or alkoxyl (e.g., —$OR^{13}$). In one embodiment, each $R^{12}$ is independently hydrogen, halo (e.g., F or Cl), cyano, $(C_1$-$C_4)$alkyl (e.g., methyl or $CF_3$), or $(C_1$-$C_4)$ alkoxyl (e.g., methoxyl or $OCF_3$). In one embodiment, each $R^{12}$ is independently hydrogen or methyl.

In one embodiment, each $R^8$ and $R^{12}$ is independently hydrogen or methyl.

In one embodiment, each $R^9$ and $R^{12}$ is independently hydrogen, halo, cyano, alkyl, or alkoxyl. In one embodiment, each $R^9$ and $R^{12}$ is independently hydrogen, halo (e.g., F or Cl), cyano, $(C_1$-$C_4)$alkyl (e.g., methyl or $CF_3$), or $(C_1$-$C_4)$alkoxyl (e.g., methoxyl or $OCF_3$). In one embodiment, each $R^9$ and $R^{12}$ is independently hydrogen or methyl.

In one embodiment, provided herein is a compound of formula (II-A):

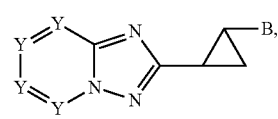

(II-A)

or a pharmaceutically acceptable salt or stereoisomer thereof, wherein Y and B are defined herein elsewhere.

In one embodiment, provided herein is a compound of the formula:

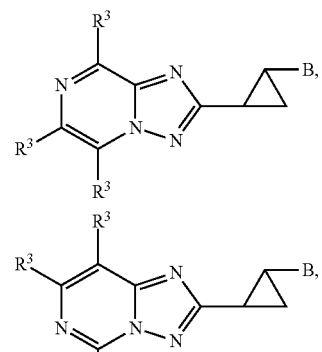

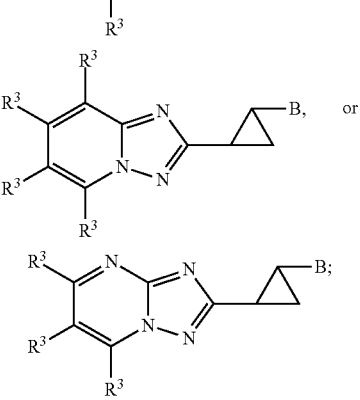

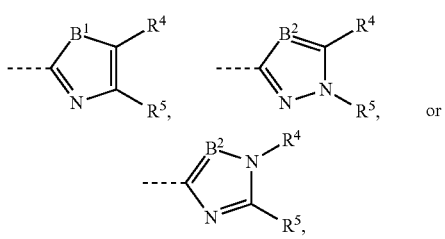

or a pharmaceutically acceptable salt or stereoisomer thereof, wherein $R^3$ and B are defined herein elsewhere.

In one embodiment, B is

wherein $B^1$, $B^2$, $R^4$, and $R^5$ are defined herein elsewhere.

In one embodiment, B is a bicyclic ring system. Examples include, but are not limited to:

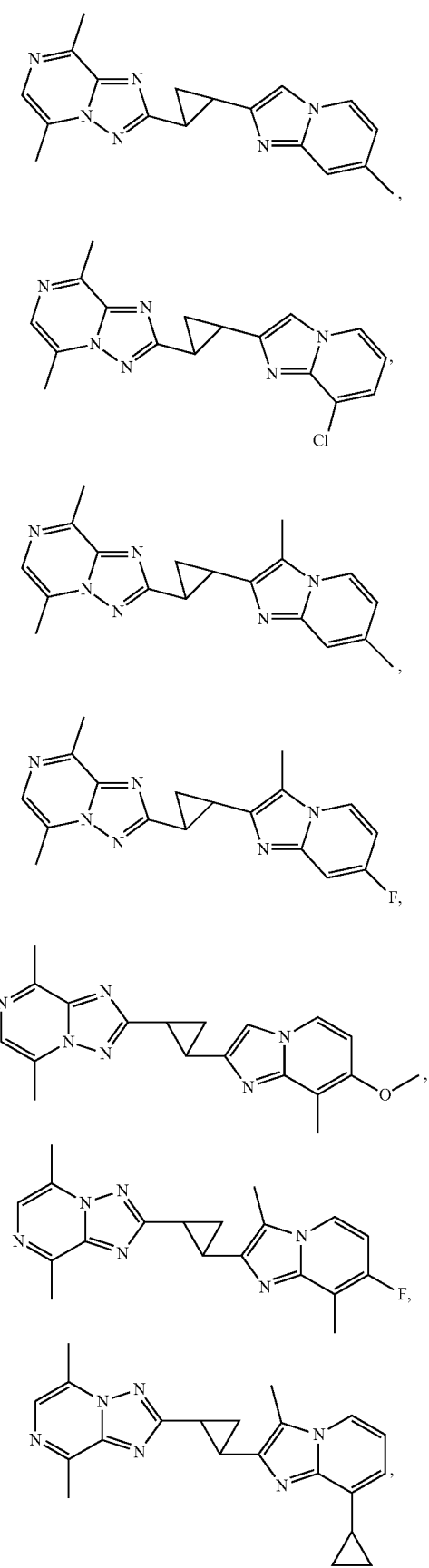
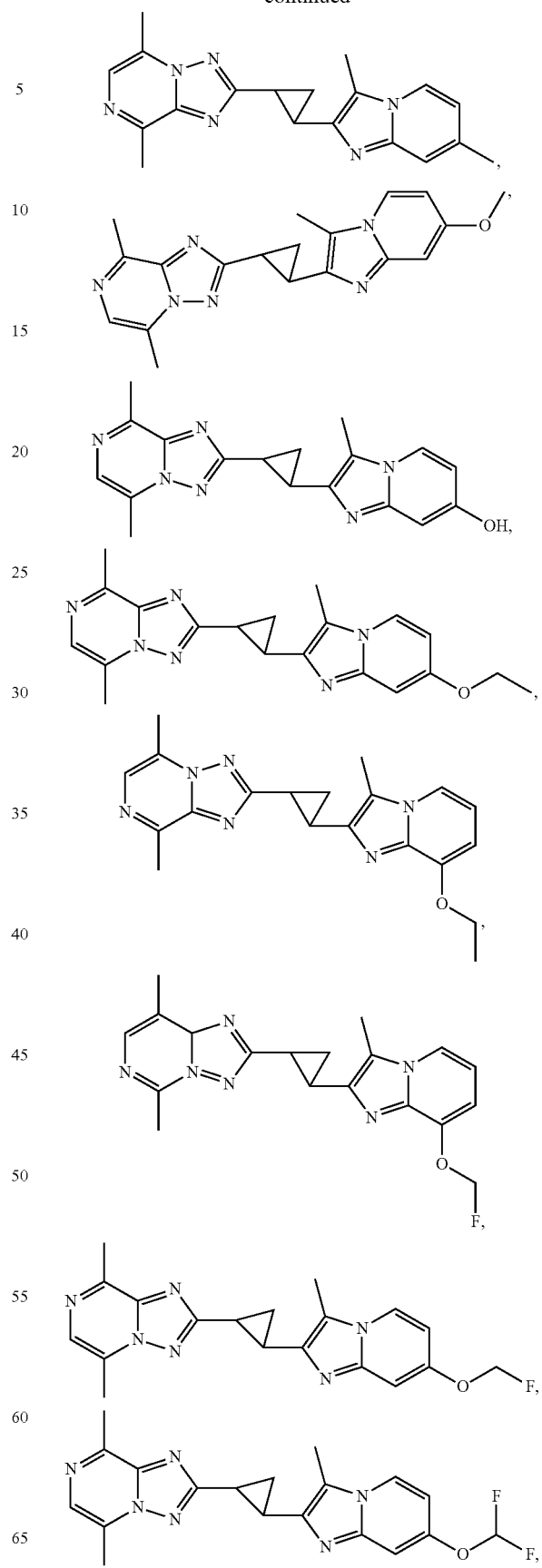

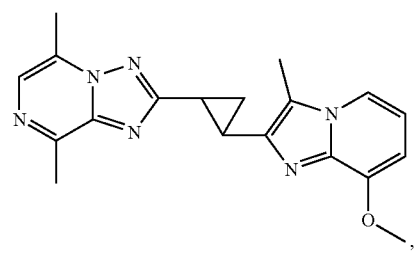
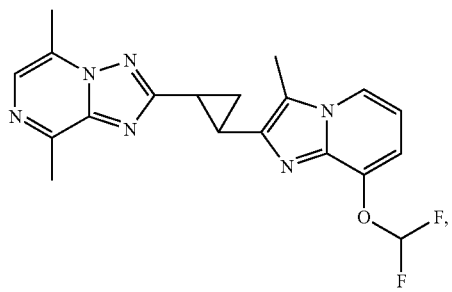
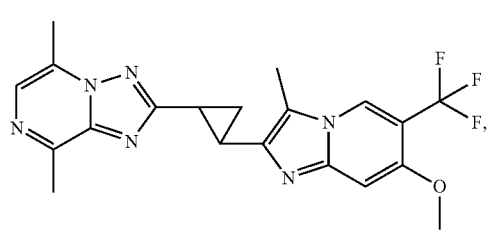
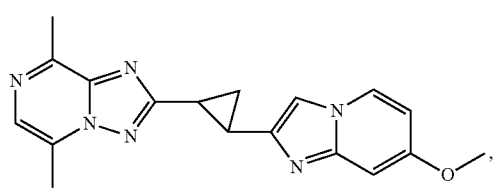
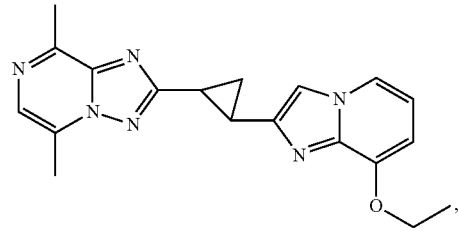 [SMILES: Cc1ncc(C)n2nc(C3CC3c3nc4c5c(ccn4c3C)OCCO5)nc12]
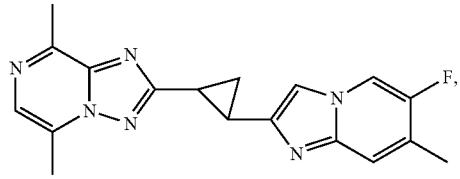
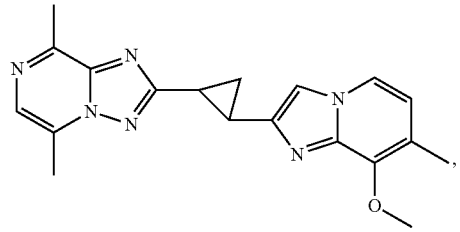

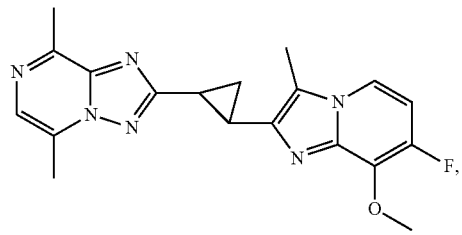
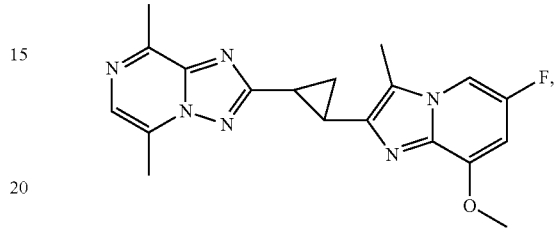
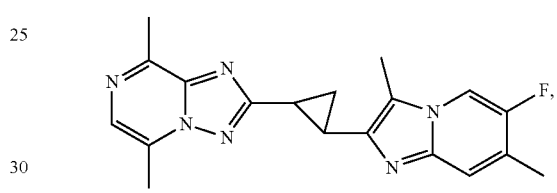
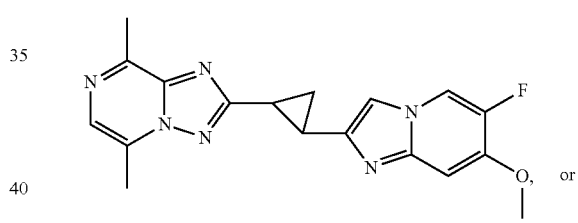

or

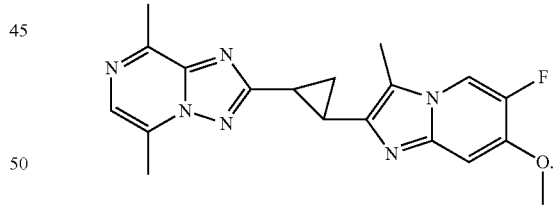

In specific embodiments, $B^2$ is CH or CMe. In specific embodiments, $B^1$ is NH or NMe. In specific embodiments, $R^4$ and $R^5$ together with the atoms to which they are attached form a pyridyl ring, which is optionally substituted with one or more substituents, such as, F, Cl, Br, CN, Me, Et, OMe, OEt, $CF_3$, $OCF_3$, $OCHF_2$, $OCH_2F$, OH, or cyclopropyl. In specific embodiments, $R^4$ and $R^5$ together with the atoms to which they are attached form a phenyl ring, which is optionally substituted with one or more substituents, such as, F, Cl, Br, CN, Me, Et, OMe, OEt, $CF_3$, $OCF_3$, $OCHF_2$, $OCH_2F$, OH, or cyclopropyl.

In one embodiment, B is a tricyclic ring system. Examples include, but are not limited to:

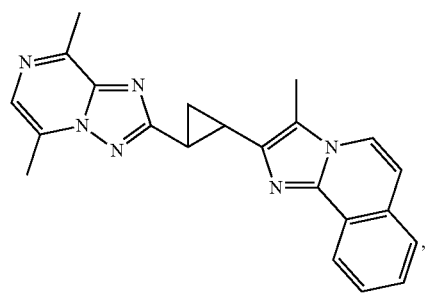

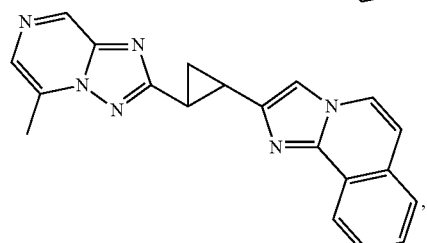

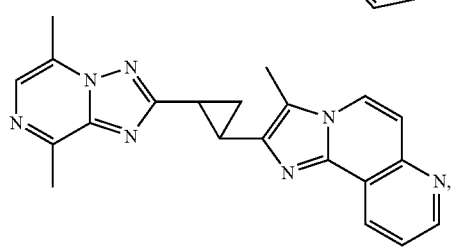

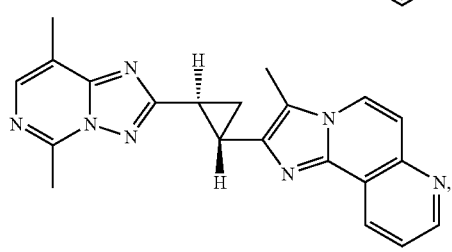

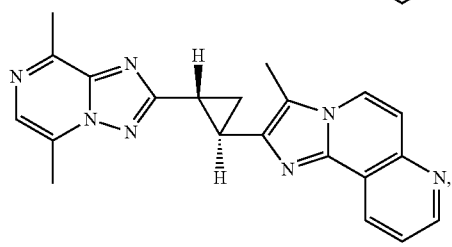

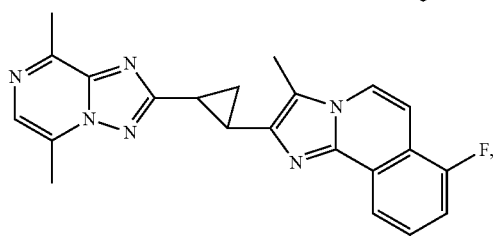

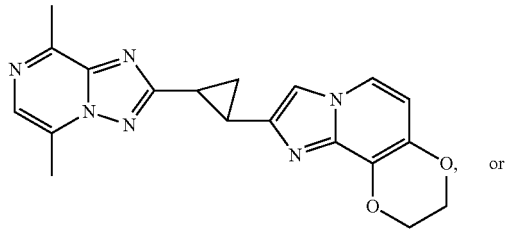

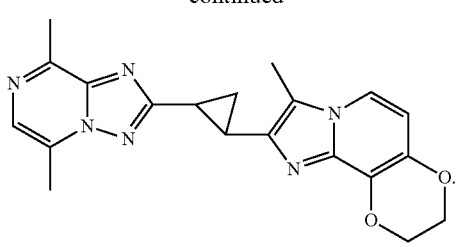

In specific embodiments, B is

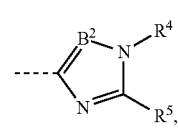

wherein $B^2$ is CH or CMe; and $R^4$ and $R^5$ are defined herein. In specific embodiments, $R^4$ and $R^5$ together with the atoms to which they are attached form an isoquinolinyl, a naphthyridinyl, or a 2,3-dihydro-[1,4]dioxino[2,3-c]pyridinyl ring, each of which is optionally substituted (e.g., with substituents such as halo).

In one embodiment, provided herein is a compound of formula (II-B):

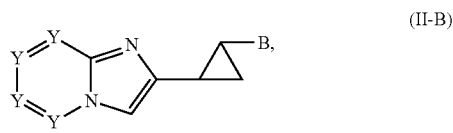

(II-B)

or a pharmaceutically acceptable salt or stereoisomer thereof, wherein Y and B are defined herein elsewhere.

In one embodiment, provided herein is a compound of the formula:

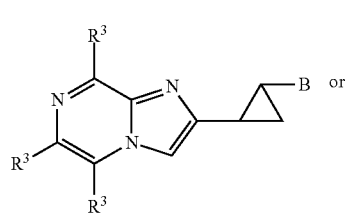

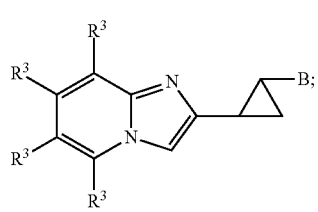

or a pharmaceutically acceptable salt or stereoisomer thereof, wherein $R^3$ and B are defined herein elsewhere.

In one embodiment, B is

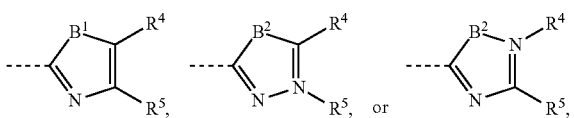

wherein $B^1$, $B^2$, $R^4$, and $R^5$ are defined herein elsewhere.

In one embodiment, B is a bicyclic ring system. Examples include, but are not limited to:

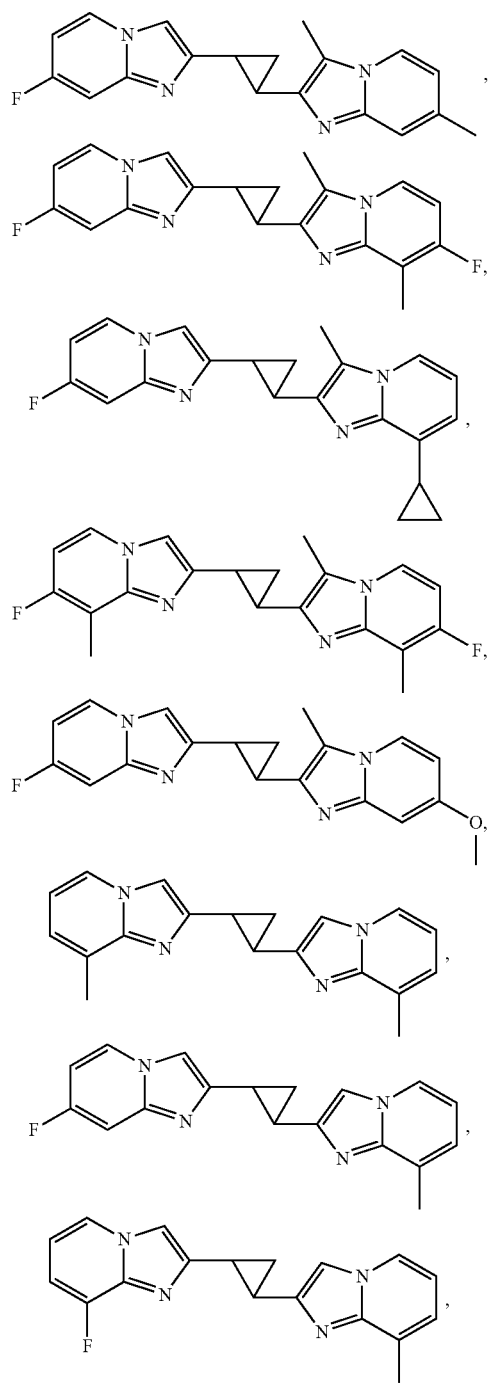

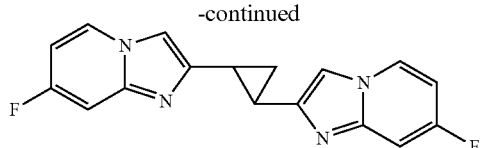
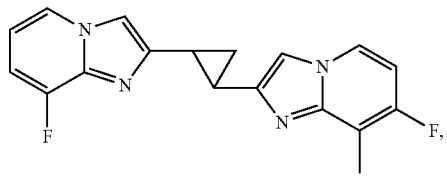
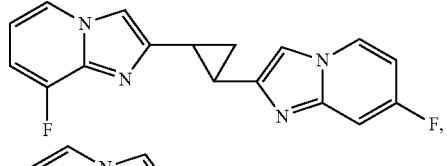
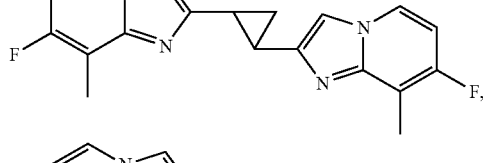
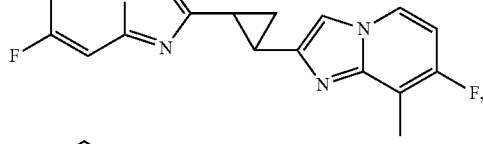
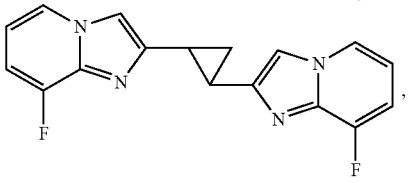
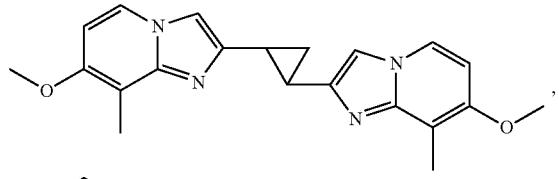
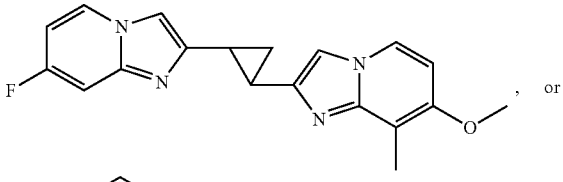
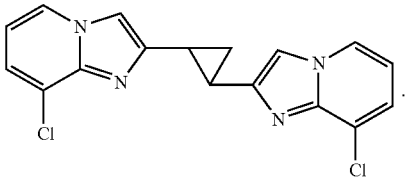

In specific embodiments, $B^2$ is CH or CMe. In specific embodiments, $B^1$ is NH or NMe. In specific embodiments, $R^4$ and $R^5$ together with the atoms to which they are attached form a pyridyl ring, which is optionally substituted with one or more substituents, such as, F, Cl, Br, CN, Me, Et, OMe, OEt, $CF_3$, $OCF_3$, $OCHF_2$, $OCH_2F$, OH, or cyclopropyl. In specific embodiments, $R^4$ and $R^5$ together with the atoms to which they are attached form a phenyl ring, which is optionally substituted with one or more substituents, such as, F, Cl, Br, CN, Me, Et, OMe, OEt, $CF_3$, $OCF_3$, $OCHF_2$, $OCH_2F$, OH, or cyclopropyl.

In one embodiment, B is a tricyclic ring system. Examples include, but are not limited to:

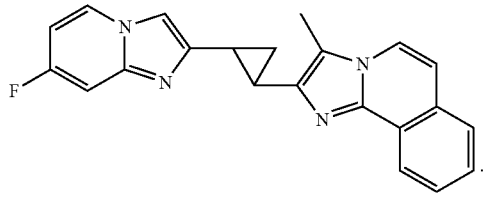 [SMILES: Cc1c(C2CC2c2cn3ccc(F)cc3n2)nc2c3ccccc3ccn12]

In specific embodiments, B is

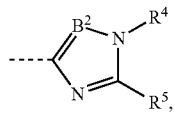

wherein $B^2$ is CH or CMe; and $R^4$ and $R^5$ are defined herein. In specific embodiments, $R^4$ and $R^5$ together with the atoms to which they are attached form an isoquinolinyl, a naphthyridinyl, or a 2,3-dihydro-[1,4]dioxino[2,3-c]pyridinyl ring, each of which is optionally substituted (e.g., with substituents such as halo).

In one embodiment, provided herein is a compound of formula (II-C):

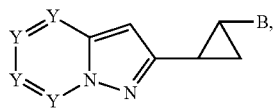
(II-C)

or a pharmaceutically acceptable salt or stereoisomer thereof, wherein Y and B are defined herein elsewhere.

In one embodiment, provided herein is a compound of the formula:

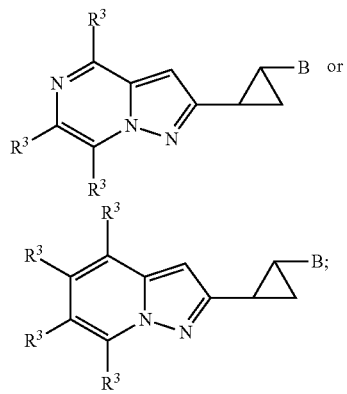

or a pharmaceutically acceptable salt or stereoisomer thereof, wherein $R^3$ and B are defined herein elsewhere.

In one embodiment, provided herein is a compound of formula (II-D):

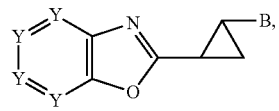
(II-D)

or a pharmaceutically acceptable salt or stereoisomer thereof, wherein Y and B are defined herein elsewhere.

In other embodiments, B is

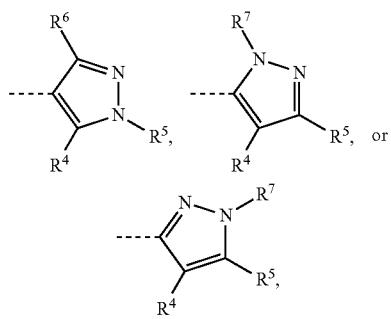

wherein $R^4$, $R^5$, $R^6$, and $R^7$ are defined herein elsewhere. Examples include, but are not limited to:

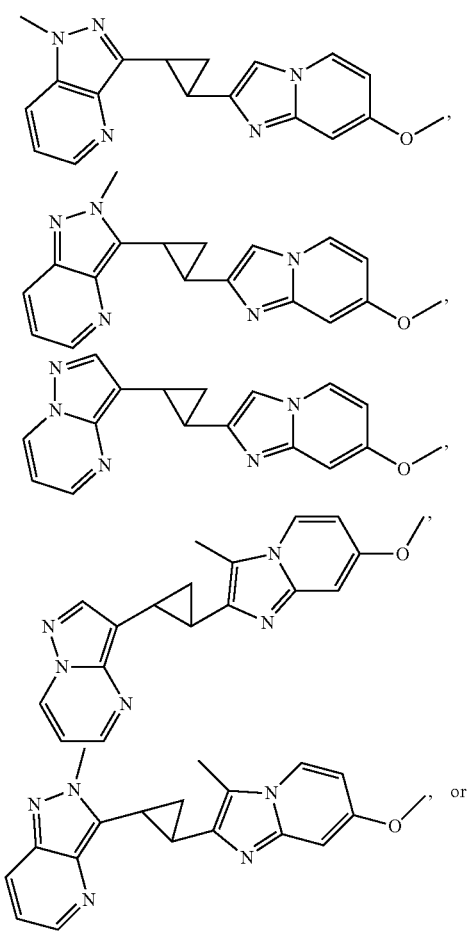

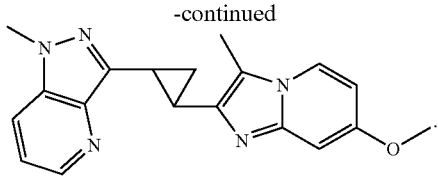

In specific embodiments, R⁶ is H. In specific embodiments, R⁷ is methyl. In specific embodiments, R⁴ and R⁵ together with the atoms to which they are attached form a pyridyl or pyrimidyl ring, each of which is optionally substituted.

In other embodiments, B is

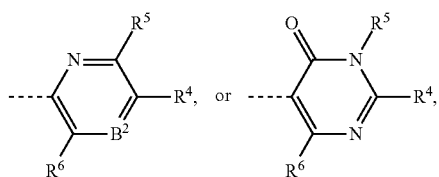

wherein B², R⁴, R⁵, and R⁶ are defined herein elsewhere. Examples include, but are not limited to:

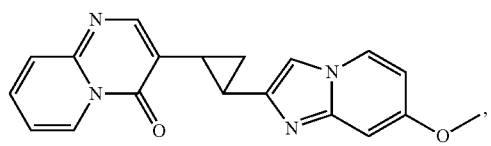

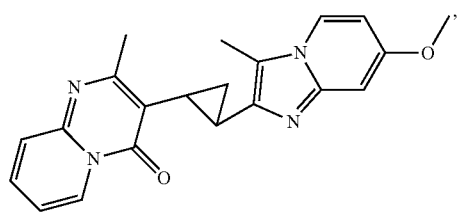

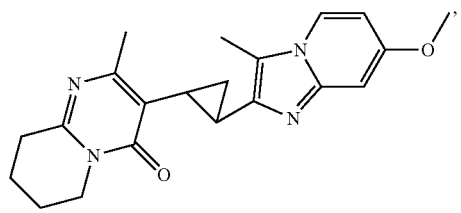

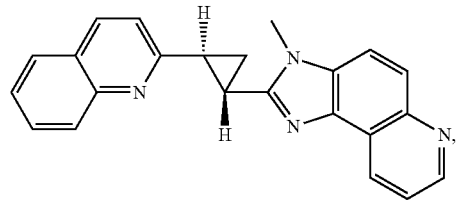

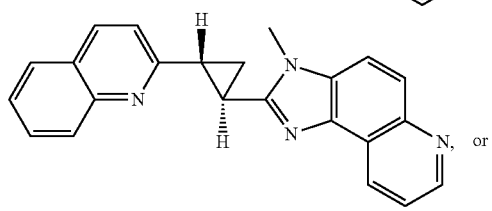

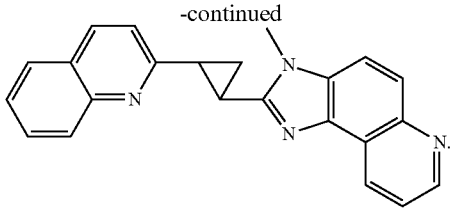

In specific embodiments, R⁶ is H or methyl. In specific embodiments, R⁴ and R⁵ together with the atoms to which they are attached form a phenyl, pyridyl, or tetrahydropyridyl ring; each of which is optionally substituted. In specific embodiments, B² is CH.

In one embodiment, B is

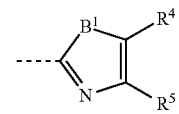

and R⁴ and R⁵ are each independently hydrogen, cyano, halo, alkyl, alkenyl, alkoxyl, aminoalkyl, heteroalkyl, cycloalkyl, aralkyl, heteroaralkyl, aryl, heteroaryl, heterocyclyl, hydroxyl, amino, imino, amido, carbonyl, thiol, sulfinyl, or sulfonyl. In one embodiment, one of R⁴ and R⁵ is hydrogen, and the other is not hydrogen. In one embodiment, one of R⁴ and R⁵ is hydrogen, and the other is an optionally substituted phenyl or an optionally substituted 5- or 6-membered heteroaryl. In specific embodiments, B¹ is NH or NMe. Specific example includes, but is not limited to,

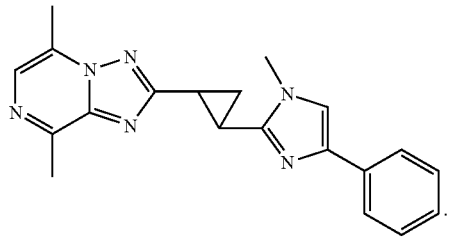 [SMILES: Cc1ncc(C)n2nc(C3CC3c3nc(-c4ccccc4)cn3C)nc12]

In other embodiments, provided herein is a compound of formula (I), wherein n is 2. Specific examples include, but are not limited to:

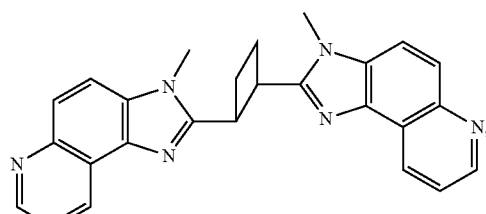

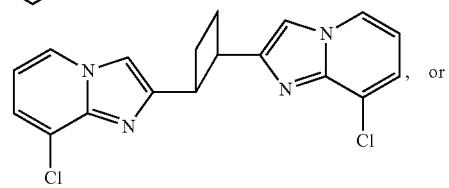

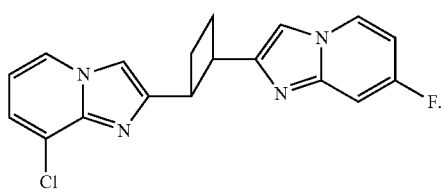

In one embodiment, provided herein is a compound having the structure:

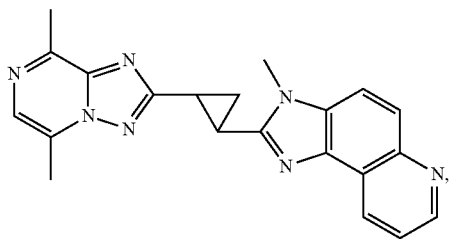 [SMILES: Cc1ncc(C)n2nc(C3CC3c3nc4c5cccnc5ccc4n3C)nc12]

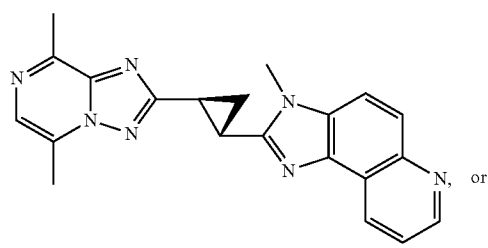

or a pharmaceutically acceptable salt or stereoisomer thereof.

In one embodiment, provided herein is a compound having the structure:

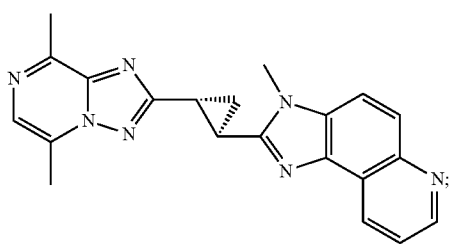

or a pharmaceutically acceptable salt or stereoisomer thereof.

In one embodiment, provided herein is a compound having the structure:

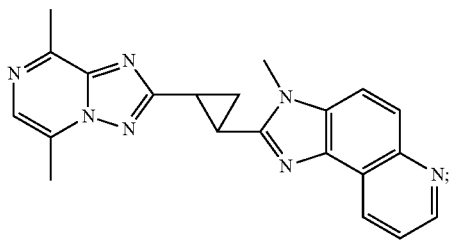

or a pharmaceutically acceptable salt or stereoisomer thereof.

In one embodiment, provided herein is a compound having the structure:

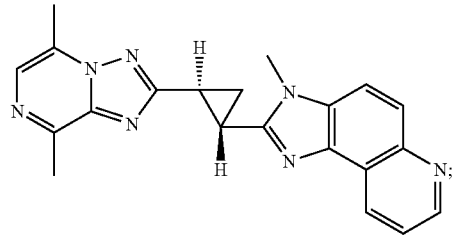 [SMILES: Cc1ncc(C)n2nc([C@H]3C[C@@H]3c3nc4c5cccnc5ccc4n3C)nc12]

or a pharmaceutically acceptable salt or stereoisomer thereof.

In one embodiment, provided herein is a compound having the structure:

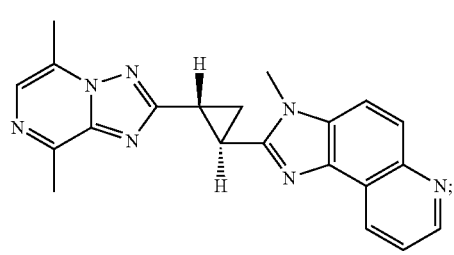 [SMILES: Cc1ncc(C)n2nc([C@@H]3C[C@H]3c3nc4c5cccnc5ccc4n3C)nc12]

or a pharmaceutically acceptable salt or stereoisomer thereof.

In one embodiment, a compound of formula (I) as provided herein is not:

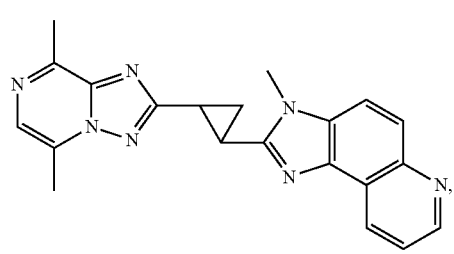

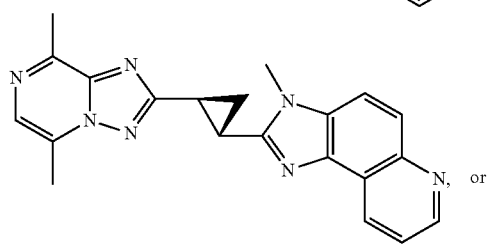

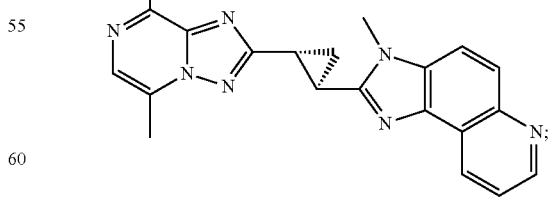

or a pharmaceutically acceptable salt or stereoisomer thereof.

In one embodiment, a compound of formula (I) as provided herein is not:

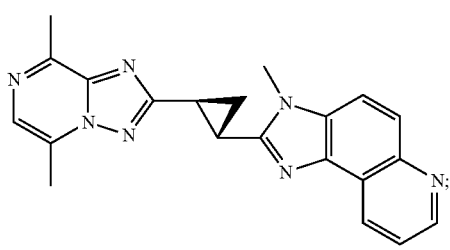 [SMILES: Cc1ncc(C)n2nc([C@H]3C[C@@H]3c3nc4c5cccnc5ccc4n3C)nc12]

or a pharmaceutically acceptable salt or stereoisomer thereof.

In one embodiment, a compound of formula (I) as provided herein is not:

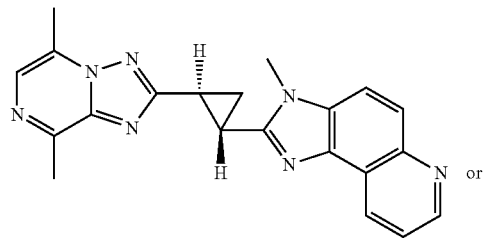

or

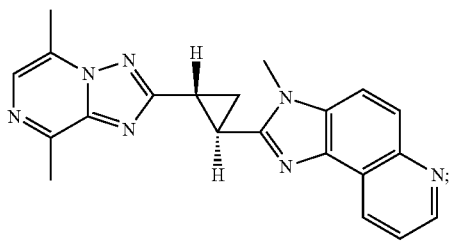

or a pharmaceutically acceptable salt or stereoisomer thereof.

In one embodiment, a compound of formula (I) as provided herein is not:

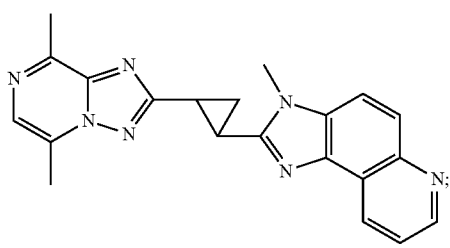 [SMILES: Cc1ncc(C)n2nc(C3CC3c3nc4c5cccnc5ccc4n3C)nc12]

or a pharmaceutically acceptable salt or stereoisomer thereof.

In one embodiment, when n is 1, m is 0, and

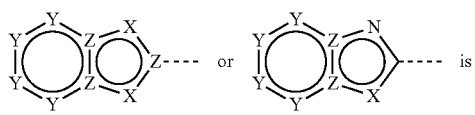 is

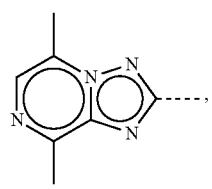

then B is not

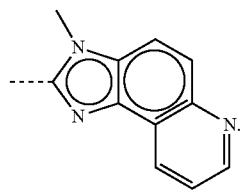

In one embodiment, when n is 1, m is 0, and

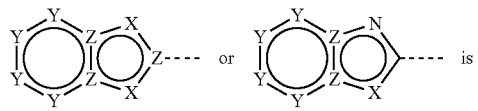 is

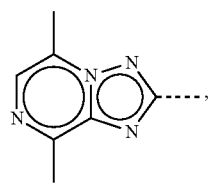

then B is a bicyclic ring system.

In one embodiment, when n is 1, m is 0, and

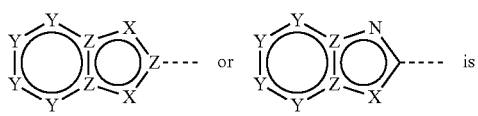 is

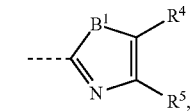

then B is not

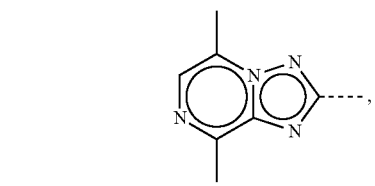

wherein $R^4$ and $R^5$ together with the atoms to which they are attached form a ring.

In one embodiment, when n is 1, m is 0, and

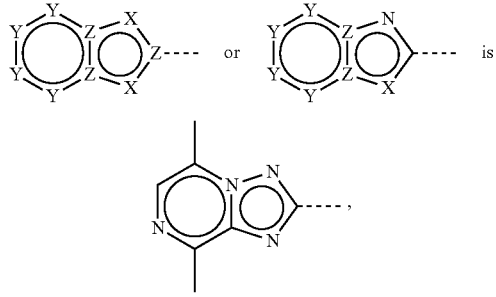

then B is not a tricyclic ring system.

In one embodiment, when n is 1, m is 0, and B is

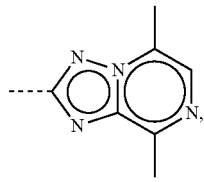

then

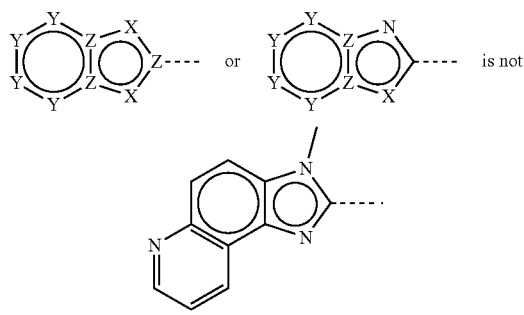

In one embodiment, when n is 1, m is 0, and B is

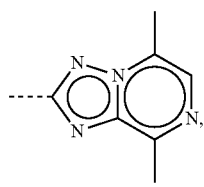

then

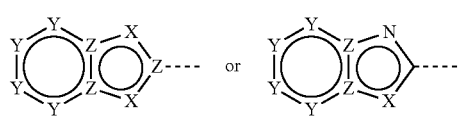

is a bicyclic ring system.

In one embodiment, when n is 1, m is 0, and B is

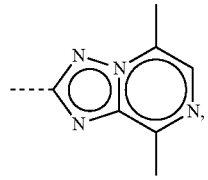

then

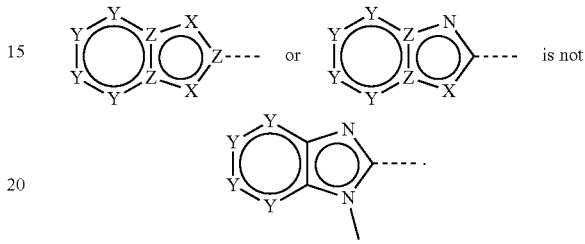

is not

In one embodiment, when n is 1, m is 0, and B is

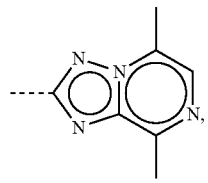

then

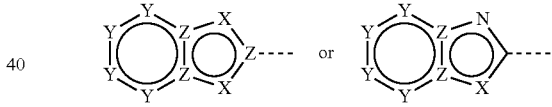

is not a tricyclic ring system.

In one embodiment, when n is 1, and m is 0, both B and

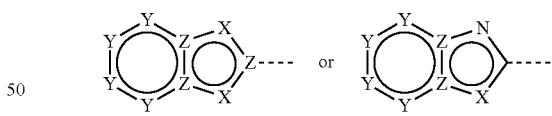

are bicyclic ring systems.

In one embodiment, $R^1$ is (i) hydrogen, halo, or cyano; or (ii) $(C_1-C_6)$alkyl, $(C_2-C_6)$alkenyl, $(C_1-C_6)$alkoxyl, $(C_1-C_6)$aminoalkyl, $(C_1-C_6)$heteroalkyl, $(C_3-C_6)$cycloalkyl, aryl, heteroaryl, heterocyclyl, amino, amido, carbonyl, thiol, sulfinyl, or sulfonyl, each of which is optionally substituted with one or more $R^{12}$, wherein $R^{12}$ is defined herein.

In one embodiment, $R^2$ is (i) hydrogen; or (ii) $(C_1-C_6)$alkyl, $(C_2-C_6)$alkenyl, $(C_1-C_6)$heteroalkyl, $(C_3-C_6)$cycloalkyl, aryl, heteroaryl, heterocyclyl, carbonyl, or sulfonyl, each of which is optionally substituted with one or more $R^{12}$, wherein $R^{12}$ is defined herein.

In one embodiment, each $R^3$ is independently (i) hydrogen, halo, or cyano; (ii) $(C_1-C_6)$alkyl, $(C_2-C_6)$alkenyl, $(C_1-C_6)$alkoxyl, $(C_1-C_6)$aminoalkyl, $(C_1-C_6)$heteroalkyl, $(C_3-$ $C_6$)cycloalkyl, aryl, heteroaryl, heterocyclyl, amino, amido, carbonyl, thiol, sulfinyl, or sulfonyl, each of which is optionally substituted with one or more $R^{12}$; or (iii) two adjacent occurrences of $R^3$ together with the atoms to which they are attached form an aryl, heteroaryl, cycloalkyl, or heterocyclyl ring, each of which is optionally substituted with one or more $R^{12}$; wherein $R^{12}$ is defined herein.

In one embodiment, $R^4$ and $R^5$ together with the atoms to which they are attached form a monocyclic or multicyclic aryl, heteroaryl, cycloalkyl, or heterocyclyl ring, each of which is optionally substituted with one or more $R^{12}$; wherein $R^{12}$ is defined herein.

In one embodiment, $R^4$ and $R^5$ are each independently (i) hydrogen, cyano, or halo; or (ii) $C_1$-$C_6$)alkyl, $(C_2$-$C_6$)alkenyl, $(C_1$-$C_6$)alkoxyl, $(C_1$-$C_6$)aminoalkyl, $(C_1$-$C_6$)heteroalkyl, $(C_3$-$C_6$)cycloalkyl, aralkyl, heteroaralkyl, aryl, heteroaryl, heterocyclyl, hydroxyl, amino, imino, amido, carbonyl, thiol, sulfinyl, or sulfonyl, each of which is optionally substituted with one or more $R^{12}$; wherein $R^{12}$ is defined herein.

In one embodiment, $R^6$ is (i) hydrogen, halo, or cyano; or (ii) $(C_1$-$C_6$)alkyl, $(C_2$-$C_6$)alkenyl, $(C_1$-$C_6$)alkoxyl, $(C_1$-$C_6)$ aminoalkyl, $(C_1$-$C_6$)heteroalkyl, $(C_3$-$C_6$)cycloalkyl, aralkyl, heteroaralkyl, aryl, heteroaryl, heterocyclyl, amino, amido, carbonyl, thiol, sulfinyl, or sulfonyl, each of which is optionally substituted with one or more $R^{12}$; wherein $R^{12}$ is defined herein.

In one embodiment, $R^7$ is (i) hydrogen; or (ii) $(C_1$-$C_6)$ alkyl, $(C_2$-$C_6$)alkenyl, $(C_1$-$C_6$)heteroalkyl, $(C_3$-$C_6)$ cycloalkyl, aryl, heteroaryl, heterocyclyl, carbonyl, or sulfonyl, each of which is optionally substituted with one or more $R^{12}$; wherein $R^{12}$ is defined herein.

In one embodiment, $R^8$ is (i) hydrogen; or (ii) $(C_1$-$C_6)$ alkyl, $(C_2$-$C_6$)alkenyl, $(C_1$-$C_6$)heteroalkyl, $(C_3$-$C_6)$ cycloalkyl, aryl, heteroaryl, heterocyclyl, carbonyl, or sulfonyl, each of which is optionally substituted with one or more $R^{12}$; wherein $R^{12}$ is defined herein.

In one embodiment, $R^9$ is (i) hydrogen, halo, or cyano; or (ii) $(C_1$-$C_6$)alkyl, $(C_2$-$C_6$)alkenyl, $(C_1$-$C_6$)alkoxyl, $(C_1$-$C_6)$ aminoalkyl, $(C_1$-$C_6$)heteroalkyl, $(C_3$-$C_6$)cycloalkyl, aralkyl, heteroaralkyl, aryl, heteroaryl, heterocyclyl, amino, amido, carbonyl, thiol, sulfinyl, or sulfonyl, each of which is optionally substituted with one or more $R^{12}$; wherein $R^{12}$ is defined herein.

In one embodiment, each $R^{12}$ is independently (i) hydrogen, halogen, cyano, =O, —$OR^{13}$, —$NR^{13}R^{14}$, —$N(R^{13})$ $C(O)R^{14}$, —$C(O)NR^{13}R^{14}$, —$C(O)R^{13}$, —$C(O)OR^{13}$, —$OC(O)R^{13}$, —$SR^{13}$, —$S(O)R^{13}$, —$S(O)_2R^{13}$, —$S(O)_2NR^{13}R^{14}$; or (ii) $(C_1$-$C_{10}$)alkyl optionally substituted with one or more $R^{15}$, $(C_1$-$C_{10})$ heteroalkyl optionally substituted with one or more $R^{15}$, $(C_3$-$C_{10}$)cycloalkyl optionally substituted with one or more $R^{15}$, $(C_7$-$C_{12}$)aralkyl optionally substituted with one or more $R^{15}$, $(C_3$-$C_{12}$)heteroaralkyl optionally substituted with one or more $R^{15}$, (6 to 10 membered)aryl optionally substituted with one or more $R^{15}$, (5 to 10 membered)heteroaryl optionally substituted with one or more $R^{15}$, or (3 to 12 membered)heterocyclyl optionally substituted with one or more $R^{15}$; wherein $R^{13}$, $R^{14}$, and $R^{15}$ are defined herein.

In one embodiment, each occurrence of $R^{15}$ is independently hydrogen, $(C_1$-$C_6$)alkyl optionally substituted with one or more $R^{13}$, $(C_3$-$C_6$)cycloalkyl optionally substituted with one or more $R^{13}$, halogen, cyano, =O, —$OR^{13}$, —$NR^{13}R^{14}$, —$N(R^{13})C(O)R^{14}$, —$C(O)NR^{13}R^{14}$, —$C(O)$ $R^{13}$, —$C(O)OR^{13}$, —$OC(O)R^{13}$, —$SR^{13}$, —$S(O)R^{13}$, —$S(O)_2R^{13}$, or —$S(O)_2NR^{13}R^{14}$; wherein $R^{13}$ and $R^{14}$ are defined herein.

In one embodiment, each $R^{13}$ and $R^{14}$ is independently hydrogen, $(C_1$-$C_6$)alkyl, $(C_1$-$C_6$)heteroalkyl, $(C_3$-$C_6$)cycloalkyl, $(C_7$-$C_{10}$)aralkyl; $(C_3$-$C_{12}$)heteroaralkyl, (6 to 10 membered) aryl, (5 to 10 membered)heteroaryl, or (3 to 12 membered)heterocyclyl; or when $R^{13}$ and $R^{14}$ are both attached to one nitrogen atom, $R^{13}$ and $R^{14}$ together with the nitrogen atom to which they are attached form a 3 to 10 membered ring.

Any of the combinations of B, m, n, X, Y, Z, $B^1$, $B^2$, R, $R^1$, $R^2$, $R^3$, $R^4$, $R^5$, $R^6$, $R^7$, $R^8$, $R^9$, $R^{12}$, $R^{13}$, $R^{14}$, $R^{15}$, and Ring C, are encompassed by this disclosure and specifically provided herein.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. Where the compound provided herein contains an alkenyl or alkenylene group, the compound may exist as one geometric (i.e., cis/trans) isomer or a mixture of geometric (i.e., cis/trans) isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism.

Unless otherwise specified, the term "compound" referred to herein, such as, e.g., a compound of formula (I), (I-A), (II-A), (II-B), (II-C), or (II-D) is intended to encompass one or more of the following: a free base of the compound or a salt thereof, a stereoisomer or a mixture of two or more stereoisomers, a solid form (e.g., a crystal form or an amorphous form) or a mixture of two or more solid forms thereof, or a solvate (e.g., a hydrate) thereof. In certain embodiments, the term "compound" referred to herein is intended to encompass a pharmaceutical acceptable form of the compound, including but not limited to, a free base, a pharmaceutically acceptable salt, a stereoisomer or a mixture of two or more stereoisomers, a solid form (e.g., a crystal form or an amorphous form) or a mixture of two or more solid forms, a solvate (e.g., a hydrate), or a cocrystal thereof. In one embodiment, the term "compound" referred to herein, such as, e.g., a compound of formula (I), (I-A), (II-A), (II-B), (II-C), or (II-D) is intended to encompass a solvate (e.g., a hydrate) thereof.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. In some instances, for compounds that undergo epimerization in vivo, one of skill in the art will recognize that administration of a compound in its (R) form is equivalent to administration of the compound in its (S) form, and vice versa. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In one embodiment, a compound provided herein has improved properties, such as, for example, solubility, metabolic stability, permeability, and/or bioavailability. In one embodiment, a compound provided herein has improved solubility. In one embodiment, a compound provided herein has decreased PGP efflux as compared to a reference compound. In one embodiment, a compound provided herein has increases brain to plasma ratio as compared to a reference compound.

In one embodiment, the compounds provided herein are modulators of a PDE enzyme. In one embodiment, the compounds provided herein are inhibitors of a PDE enzyme. In one embodiment, the compounds provided herein are inhibitors of PDE-10. In one embodiment, the compounds provided herein are inhibitors of PDE-10A. In one embodiment, the compounds provided herein are selective inhibitors of PDE-10. In one embodiment, the compounds provided herein are selective inhibitors of PDE-10A. In one embodiment, the compounds provided herein are active in one or more animal models for a disorder provided herein elsewhere. In one embodiment, the compounds provided herein are active in one or more animal models for a CNS disorder provided herein elsewhere. In one embodiment, the compounds provided herein are active in one or more animal models for psychosis, schizophrenia, or antipsychotic activity, including without limitation, the conditioned avoidance response (CAR) assay, and any other animal models for psychosis, schizophrenia or antipsychotic activity that are known in the art. In one embodiment, the compounds provided herein are active in one or more animal models for psychosis, schizophrenia, or antipsychotic activity, including but not limited to, conditioned avoidance response (CAR), pre-pulse inhibition (PPI), PCP-induced hyperlocomotion, and other animal models provided herein elsewhere. In one embodiment, compounds that are active in in vitro assays (e.g., PDE-10A inhibition) or in vivo models for psychosis, schizophrenia or antipsychotic activity (e.g., CAR) are further optimized to improve the potency in in vitro and in vivo assays and drug-like properties such as, e.g., solubility and lipophilicity. In one embodiment, the compounds provided herein are useful for treating, preventing, or ameliorating one or more symptoms of schizophrenia, including, positive, negative, and cognitive symptoms. In one embodiment, the compounds provided herein induce fewer side effects, such as weight gain, in a subject treated with the compound. In one embodiment, the compounds provided herein induce fewer side effects, such as extrapyramidal side effects, in a subject treated with the compound. In one embodiment, the compounds provided herein are active in one or more animal models for obesity, undesirable weight retention or weight gain, metabolic syndrome, diabetes, non-insulin dependent diabetes, impaired glucose tolerance, or hyperglycemia, including without limitation, in vivo glucose tolerance test (GTT), diet-induced obesity model, obesity food intake model, and any other animal models known in the art or provided herein elsewhere. In one embodiment, compounds that are active in in vitro assays (e.g., PDE-10A inhibition) or in vivo models for obesity, undesirable weight retention or weight gain, metabolic syndrome, diabetes, non-insulin dependent diabetes, impaired glucose tolerance, or hyperglycemia are further optimized to improve the potency in in vitro and in vivo assays and drug-like properties such as, e.g., solubility and lipophilicity.

C. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, the compound of formula (I) may be prepared following Schemes, using suitable starting materials known in the art and/or available from a commercial source. In one embodiment, the starting materials may be prepared from commercially available compounds using procedures and conditions known in the art. Exemplary procedures and conditions are provided herein elsewhere.

In one embodiment, a suitable cyclopropane aldehyde (e.g., the cis or trans isomer) is reacted with an iminodiazinamine or iminopyridinamine salt (e.g., 2-imino-3,6-dimethylpyrazin-1(2H)-amine 2,4,6-trimethylbenzenesulfonate) in the presence of base and oxygen to form a fused heterocyclic compound, which can be further converted to one or more embodiments of a compound of formula (I). For example, a suitable cyclopropane carboxylic ester may be hydrolyzed using conditions known in the art. The resulting acid is treated with an appropriate activating reagent (e.g., oxalyl chloride, sulfonyl chloride, or isobutylchloroformate) and then treated with ethylmagnesium bromide to form a ketone intermediate. Installation of an alpha-halogen may be accomplished using conditions and reagents known in the art (e.g., NBS, $Br_2$, PTT). The resulting bromoethyl ketone is then reacted with an optionally substituted aminopyridine to form an imidazopyridine compound (e.g., Scheme 1).

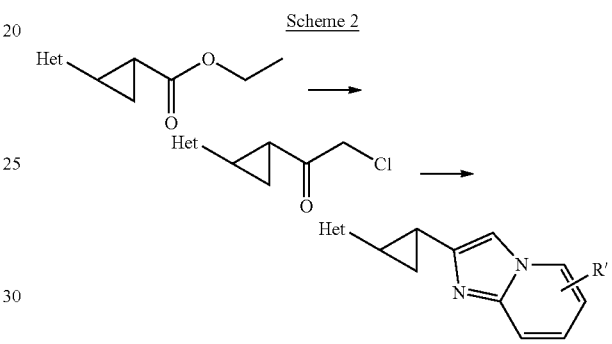

In one embodiment, a suitable cyclopropane carboxylic ester is hydrolyzed using conditions known in the art, and the resulting acid is treated with an appropriate activating reagent (e.g., oxalyl chloride, sulfonyl chloride, or isobutylchloroformate) and then treated with diazomethane in the presence of HCl. The resulting chloromethyl ketone is reacted with an optionally substituted aminopyridine to form an imidazopyridine compound (e.g., Scheme 2).

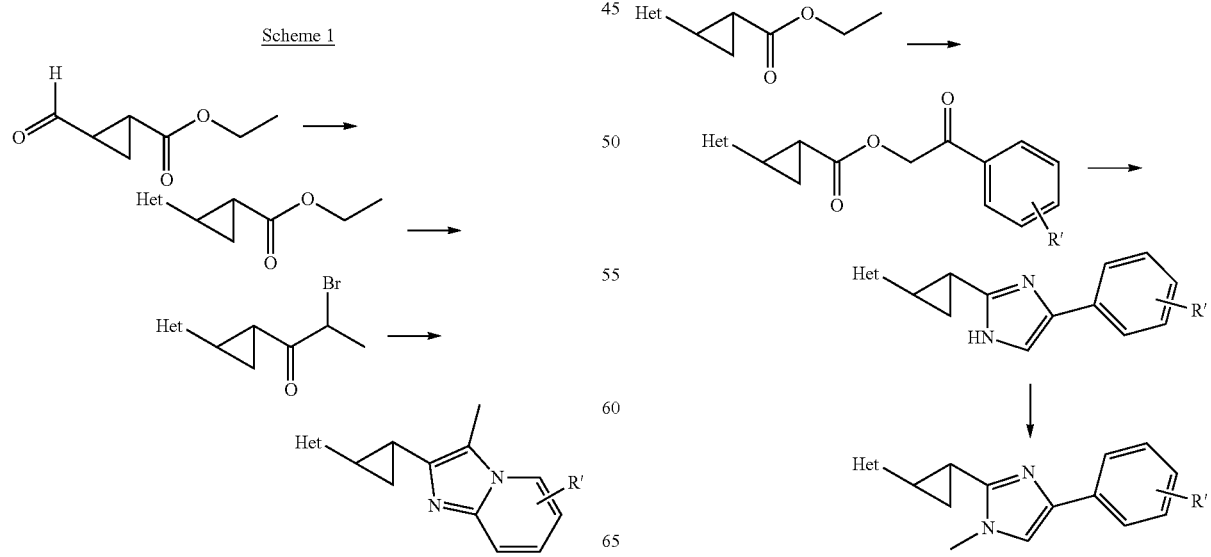

In one embodiment, a suitable cyclopropane carboxylic ester is hydrolyzed using conditions known in the art, and the resulting acid is treated with an appropriate bromoacetophenone starting material (e.g., in base aprotic solvent). The resulting ketoester is condensed in the presence of an appropriate ammonium salt (e.g., NH₄OAc, NH₄Cl, or NH₄O₂CH (ammonium formate)) under thermal dehydrating conditions to afford a phenylimidazole compound. In some embodiments, the imidazole compound is alkylated with an appropriate alkyl halide to form the alkyl derivative (e.g., Scheme 3).

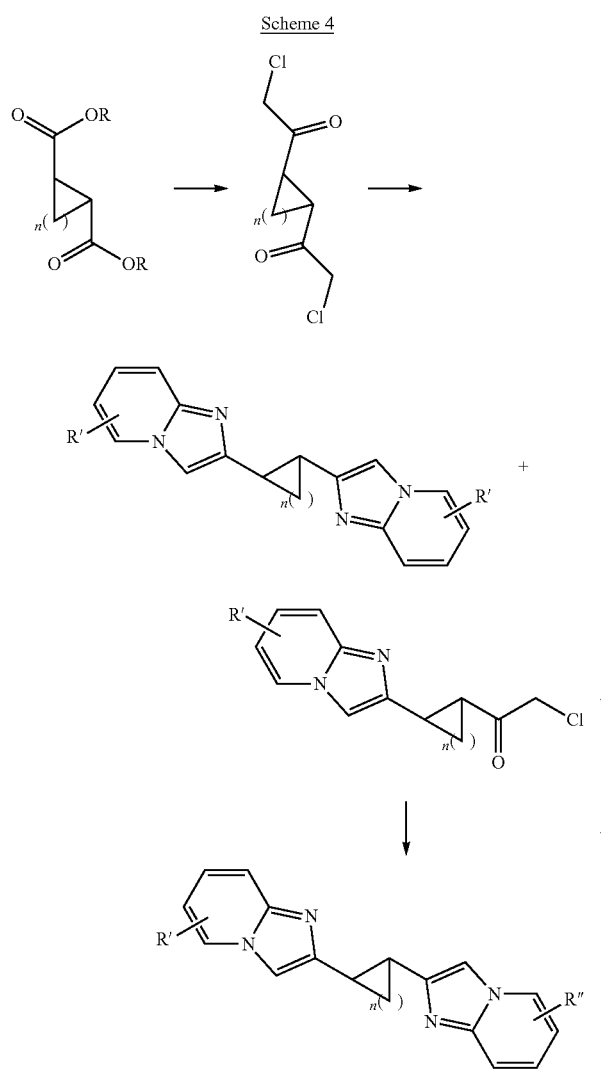

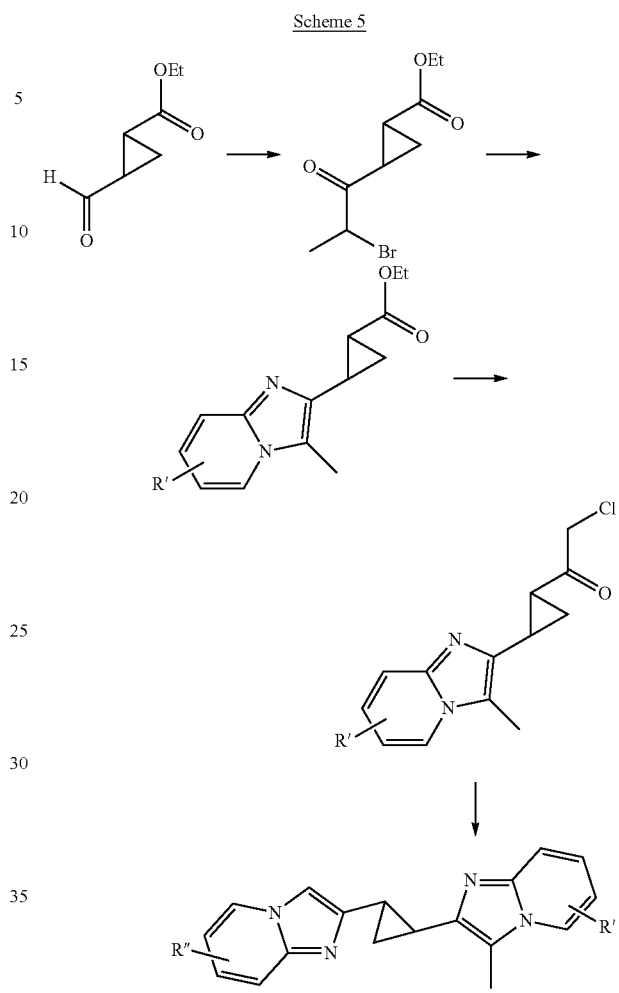

In one embodiment, a suitable cycloalkane dicarboxylic ester (e.g., the trans isomer) is hydrolyzed using conditions known in the art, and the resulting di-acid is treated with an appropriate activating reagent (e.g., oxalyl chloride, sulfonyl chloride, or isobutylchloroformate) and then treated with diazomethane in the presence of HCl. The resulting chloromethyl ketone may be reacted with an optionally substituted aminopyridine to give a symmetric dimmer product. In some embodiments, incomplete reaction allows for reaction of a second aminopyridine to form a mixed bis-imidazopyridine congener (e.g., Scheme 4).

In one embodiment, commercially available ethyl 2-formylcyclopropanecarboxylate is converted into an ethyl ketone by Grignard addition, followed by an appropriate oxidation protocol (e.g., Dess-Martin, PCC, or MnO₂) to afford a ketone product. Installation of an alpha-halogen may be accomplished using conditions and reagents known in the art (e.g., NBS, Br₂, or PTT). The resulting bromoethyl ketone may be reacted with an optionally substituted aminopyridine to give an imidazopyridine cyclopropane carboxylic ester (e.g., Scheme 5).

In one embodiment, the cyclopropane carboxylic ester is hydrolyzed using conditions known in the art, and the resulting acid is treated with an appropriate activating reagent (e.g., oxalyl chloride, sulfonyl chloride, or isobutylchloroformate) and then treated with diazomethane in the presence of HCl. The resulting chloromethyl ketone is reacted with an optionally substituted aminopyridine to form an imidazopyridine compound (e.g., Scheme 5).

Scheme 6

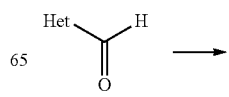

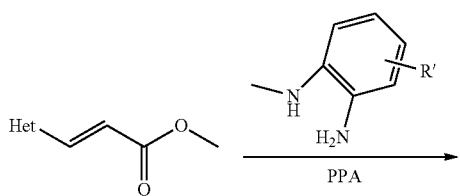

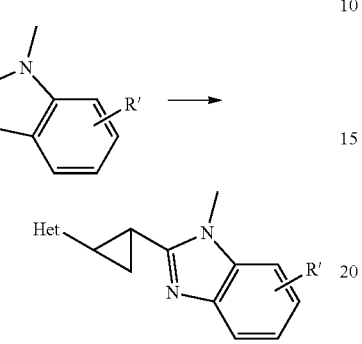

In one embodiment, a suitable heteroaryl aldehyde is treated under Horner-Wadsworth-Emmons conditions to render an α,β-unsaturated ester, which is cyclized under acidic conditions (e.g., PPA) with an appropriate 1,2-diaminobenzene, to afford a vinyl benzimidazole. The olefin can be converted into a cyclopropane moiety using conditions and reagents known in the art (e.g., Scheme 6).

Scheme 7

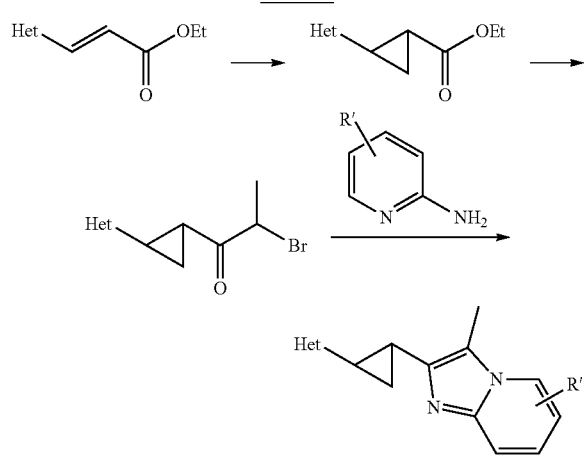

In one embodiment, a suitable 4-unsaturated ester is converted into a cyclopropane moiety using conditions and reagents known in the art to give a cyclopropane carboxylic ester. The cyclopropane carboxylic ester is hydrolyzed using conditions known in the art, and the resulting acid is treated with an appropriate activating reagent (e.g., oxalyl chloride, sulfonyl chloride, or isobutylchloroformate) and then treated with ethylmagnesium bromide to form a ketone intermediate. Installation of an alpha-halogen can be accomplished using conditions and reagents known in the art (e.g., NBS, Br$_2$, or PTT). The resulting bromoethyl ketone is reacted with an optionally substituted aminopyridine to form an imidazopyridine compound (e.g., Scheme 7).

Scheme 8

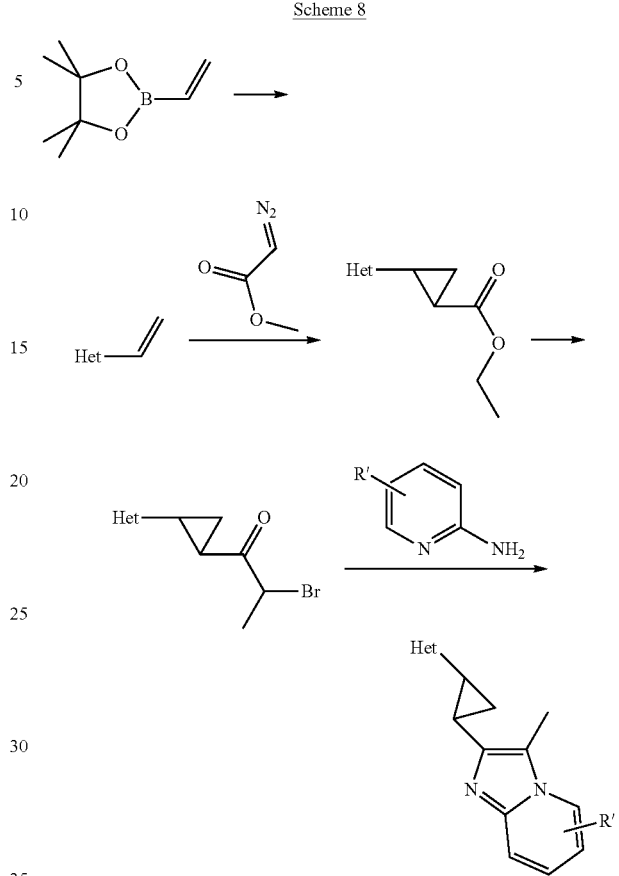

In one embodiment a suitable vinyl boronate is reacted with an appropriate heteroarylhalide under Suzuki coupling conditions. To the resulting vinyl heteroaryl compound is added methyl or ethyl-2-diazoacetate in the presence of Pd(II) (e.g., Pd(OAc)$_2$ or Pd$_2$(dba)$_3$) to afford a cyclopropane carboxylic ester. The cyclopropane carboxylic ester is hydrolyzed using conditions known in the art, and the resulting acid is treated with an appropriate activating reagent (e.g., oxalyl chloride, sulfonyl chloride, or isobutyl-chloroformate) and then treated with ethylmagnesium bromide to form a ketone intermediate. Installation of an alpha-halogen can be accomplished using conditions and reagents known in the art (e.g., NBS, Br$_2$, or PTT). The resulting bromoethyl ketone is reacted with an optionally substituted aminopyridine to form an imidazopyridine compound (e.g., Scheme 8).

Scheme 9

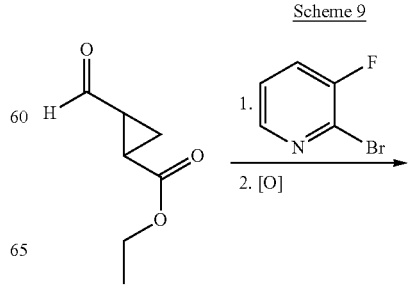

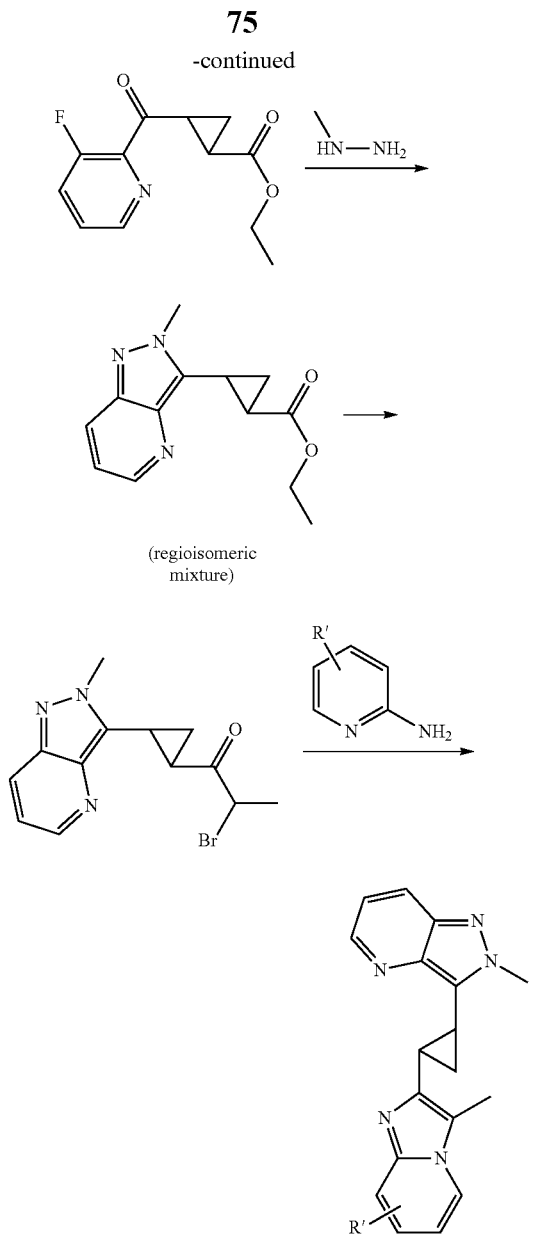

(regioisomeric mixture)

In one embodiment, a suitable aldehyde is reacted with 2-bromo-3-fluoropyridine in the presence of isopropyl magnesium bromide to afford a pyridyl methyl alcohol intermediate, which is subsequently oxidized using a suitable protocol (e.g., Swern, Dess-Martin, or MnO₂) and then treated with an appropriate derivative of hydrazine to afford a substituted pyrazopyridine as a mixture of regioisomers (e.g., Scheme 9).

In one embodiment, a pyrazopyridine is appended to a cyclopropane carboxylic ester, which can be hydrolyzed using conditions known in the art. The resulting acid is treated with an appropriate activating reagent (e.g., oxalyl chloride, sulfonyl chloride, or isobutylchloroformate) and then treated with ethylmagnesium bromide to form a ketone intermediate. Installation of an alpha-halogen can be accomplished using conditions and reagents known in the art (e.g., NBS, Br₂, or PTT). The resulting bromoethyl ketone is reacted with an optionally substituted aminopyridine to form an imidazopyridine compound (e.g., Scheme 9).

Scheme 10

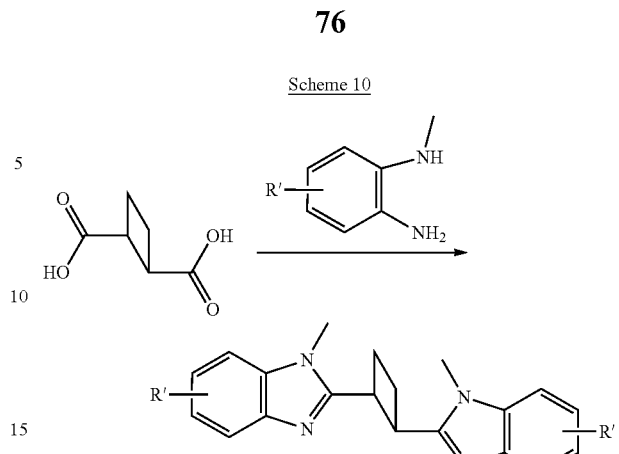

In one embodiment, a cyclobutane dicarboxylic acid (e.g., the cis or trans isomer) is cyclized under acidic conditions (e.g., PPA) with an appropriate 1,2-diaminobenzene, to afford a benzimidazole compound (e.g., Scheme 10).

In other embodiments, the compounds provided herein may be prepared using the general procedures described herein. In one embodiment, the compounds provided herein may be prepared following a synthetic scheme described herein.

In certain embodiments, the compounds provided herein are prepared as a mixture of two or more stereoisomers or diastereoisomers. In one embodiment, the stereoisomers or diastereoisomers are separated using techniques known to those skilled in the art, including but not limited to, chiral column chromatography and chiral resolution by forming a salt with a suitable chiral counterion. In certain embodiments, the compounds provided herein are prepared following one or more stereoselective reaction(s). In some embodiment, the compounds provided herein are prepared as a substantially pure stereoisomer.

D. Methods of Use

1. Modulation of PDE Enzyme Activity

In one embodiment, provided herein is a method of binding a compound provided herein to a PDE enzyme, such as, PDE-10, in one embodiment, PDE-10A. The method comprises contacting the PDE enzyme with a compound provided herein. In one embodiment, the binding to PDE enzyme is assessed using an in vitro binding assay, such as those known in the art.

In one embodiment, provided herein is a method of modulating (e.g., inhibiting or augmenting) the activity of a PDE enzyme, such as, PDE-10, in one embodiment, PDE-10A. In one embodiment, provided herein is a method of inhibiting the activity of a PDE enzyme, such as, PDE-10, in one embodiment, PDE-10A. In one embodiment, the method comprises contacting a PDE enzyme, such as PDE-10A, with a compound provided herein, in vitro or in vivo. In one embodiment, the PDE enzyme, such as PDE-10A, is contacted by a compound provided herein by administering to a subject a therapeutically effective amount of the compound provided herein, or a pharmaceutically acceptable salt or stereoisomer thereof. The subject may be a human. In one embodiment, the PDE enzyme is PDE-10. In one embodiment, the PDE enzyme is PDE-10A.

In other embodiments, the compound provided herein inhibits the activity of a PDE enzyme, such as PDE-10A Inhibition of PDE activity may be measured using assays known in the art. In some embodiments, the activity of the PDE enzyme is inhibited or reduced by about 1%, about 5%, about 10%, about 20%, about 30%, about 40%, about 50%, about 60%, about 70%, about 80%, about 90%, about 95%, about 99% or more than about 99%, as compared with activity without contacting the PDE enzyme with a compound provided herein (e.g., vehicle condition). In one embodiment, the inhibition of enzyme activity is dose dependent. Exemplary assay methods include, but are not limited to, in vitro binding assays and in vitro functional assays. In one embodiment, the functional assay utilizes an appropriate cell-line expressing a desired PDE enzyme, such as PDE-10A. In one embodiment, the functional assay utilizes a PDE enzyme purified following expression using an appropriate recombinant system. In one embodiment, inhibition of PDE enzyme activity may be assessed using a fluorescent assay, e.g., utilizing a Fluorescein-labeled cAMP/cGMP substrate. In one embodiment, the functional assay utilizes synaptosomes isolated from brain tissue of an appropriate organism. In one embodiment, the assay is carried out in vivo and involves treatment of a test subject (e.g., a rodent) with a compound provided herein. In one embodiment, a test subject is treated with a reference compound or vehicle, as positive or negative controls. In one embodiment, the assay is followed by isolation of brain tissue and ex vivo analysis of substrate concentration (e.g., cAMP or cGMP) in the brain tissue. In one embodiment, the assay is followed by isolation of brain microdialysates and ex vivo analysis of substrate concentration (e.g., cAMP or cGMP) in the microdialysates.

In certain embodiments, provided herein are methods of inhibiting the activity of a PDE enzyme, e.g., PDE-10A, in a subject (e.g., human) comprising administering to the subject an effective amount of a compound provided herein. In some embodiments, the activity of PDE enzyme is inhibited by about 1%, about 5%, about 10%, about 20%, about 30%, about 40%, about 50%, about 60%, about 70%, about 80%, about 90%, about 95%, about 99%, or more than about 99%, when measured using an assay described herein elsewhere.

In one embodiment, provided herein is a method of inhibiting a PDE enzyme to increase the concentration of a cyclic nucleotide substrate. In one embodiment, the method includes contacting the cell with a compound provided herein. In one embodiment, the cell is a brain cell, such as a medium spiny neuron. In one embodiment, the enzyme inhibition occurs in vitro. In one embodiment, the enzyme inhibition occurs in vivo. Thus, in certain embodiments, provided herein are methods of increasing the level of a cyclic nucleotide substrate (e.g., cAMP or cGMP) comprising administering to a subject (e.g., human) an effective amount of a compound provided herein.

Inhibition of PDE enzyme can be shown, for example, by performing various in vitro functional assays utilizing a cell type which expresses a certain type of PDE enzyme, such as PDE-10A, together with an appropriate labeled cyclic nucleotide substrate. In some embodiments, the compounds provided herein inhibit the PDE enzyme in a dose-dependent manner, with an $EC_{50}$ of, for example, between about 0.1 nM and about 10 μM, between about 1 nM and about 1 μM between about 1 nM and about 500 nM, and between about 1 nM and about 100 nM, in a functional PDE inhibition assay, such as those described herein. In one embodiment, the $EC_{50}$ is less than about 0.01 nM, less than about 0.1 nM, less than about 1 nM, less than about 3 nM, less than about 10 nM, less than about 30 nM, less than about 100 nM, less than about 300 nM, less than about 1000 nM, less than about 3000 nM, or less than about 10000 nM. In one embodiment, the $EC_{50}$ is about 0.01 nM, about 0.1 nM, about 1 nM, about 3 nM, about 10 nM, about 30 nM, about 100 nM, about 300 nM, about 1000 nM, about 3000 nM, or about 10000 nM.

2. Treatment, Prevention, and/or Management of Disorders

In one embodiment, provided herein is a method for the treatment, prevention, and/or management of various disorders, including a disorder of the central nervous system, comprising administering a compound or a composition provided herein. In one embodiment, provided herein is a method for the treatment, prevention, and/or amelioration of one or more symptoms of a disorder (e.g., a CNS disorder), comprising administering a compound or a composition provided herein. In one embodiment, the disorders provided herein include, but are not limited to, schizophrenia, psychosis, cognitive disorders, mood disorders, depression, attention deficit disorders, and neurodegenerative diseases. In one embodiment, the disorders include, but are not limited to, neurological disorder, schizophrenia, schizophrenia-related disorders, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesia, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, and hyperglycemia. In one embodiment, the disorder provided herein is a disorder known in the art that affects the central nervous system (i.e., a CNS disorder).

In one embodiment, provided herein is a method of administering a compound provided herein in a disease model that is known in the art. In one embodiment, the disease model is an animal model. In one embodiment, provided herein is a method of administering the compound provided herein in an animal model that is predictive of efficacy in the treatment of certain diseases in a human. The method comprises administering a compound provided herein in a subject. In one embodiment, the method comprises administering to a subject a therapeutically effective amount of a compound provided herein, or a pharmaceutically acceptable salt or stereoisomer thereof. In one embodiment, the method comprises treatment of a test subject (e.g., a mice or rat) with a compound provided herein. In one embodiment, the method comprises treatment of a test subject (e.g., a mice or rat) with a compound provided herein as well as a reference compound. In one embodiment, the in vivo activity of the compound provided herein is dose dependent. In one embodiment, without being limited to a particular theory, the method provided herein comprises administering an effective amount of a compound provided herein to inhibit PDE-10 activity in a subject. In one embodiment, without being limited to a particular theory, the method provided herein comprises administering an effective amount of a compound provided herein to inhibit PDE-10A activity in a subject.

In one embodiment, the compounds provided herein are active in one or more animal models of schizophrenia or psychosis, such as conditioned avoidance responding (CAR), auditory gating (e.g., amphetamine-induced deficit in auditory gating), phencyclidine (PCP)-induced hyperlocomotion, stimulant-induced hyperlocomotion/hyperactivity, PCP-induced hyperactivity, and amphetamine-induced hyperactivity. In one embodiment, the compounds provided herein inhibit exploratory locomotor activity and/or hyperactivity caused by a dopamine releasing agent, such as amphetamine, and/or a NMDA receptor antagonist, such as phencyclidine (PCP). In one embodiment, the compounds provided herein inhibit conditioned avoidance responding. In one embodiment, the compounds provided herein are active in pre-pulse inhibition (PPI) of acoustic startle response model. In one embodiment, the compounds provided herein inhibit spontaneous locomotor activity. In one embodiment, the compounds provided herein improve cognitive function in a treated subject. In one embodiment, the compounds provided herein improve social interaction in a treated subject. In one embodiment, the compounds provided herein improve social cognition in a treated subject. In one embodiment, the compounds provided herein improve executive function in a treated subject. In one embodiment, the compounds provided herein caused reduced Parkinsonian side effects in a treated subject. In one embodiment, the compounds provided herein produce relatively low levels of catalepsy, as compared to other therapeutic agents. In one embodiment, the compounds provided herein provide a neuron-protective effect on neurons, such as medium spiny neurons, in a treated subject. In one embodiment, the compounds provided herein are active in a striatal quinolinic acid lesion model for Huntington's disease. In one embodiment, the compounds provided herein are active in dizocilpine-induced hyperactivity and stereotyped sniffing model for psychosis. In one embodiment, the compounds provided herein inhibit apomorphine-induced climbing. In one embodiment, the compounds provided herein inhibit N-methyl-D-aspartate antagonist-induced deficits in prepulse inhibition of acoustic startle response. In one embodiment, the compounds provided herein improve baseline sensory gating. In one embodiment, the compounds provided herein increase sociality in a social approach/social avoidance assay. In one embodiment, the compounds provided herein enhance social odor recognition. In one embodiment, the compounds provided herein improve novel object recognition. In one embodiment, the compounds provided herein are active in a disease model for a disorder provided herein elsewhere, which is known in the art. See, e.g., Grauer et al., Phosphodiesterase 10A Inhibitor Activity in Preclinical Models of the Positive, Cognitive, and Negative Symptoms of Schizophrenia, *Journal of Pharmacology and Experimental Therapeutics,* 2009, 331(2), 574-90; Threlfell et al., Inhibition of Phosphodiesterase 10A Increases the Responsiveness of Striatal Projection Neurons to Cortical Stimulation, *Journal of Pharmacology and Experimental Therapeutics,* 2009, 328(3), 785-95; Schmidt et al., Preclinical Characterization of Selective Phosphodiesterase 10A Inhibitors: A New Therapeutic Approach to the Treatment of Schizophrenia, *Journal of Pharmacology and Experimental Therapeutics,* 2008, 325(2), 681-90.

In one embodiment, provided herein is a method of treating, preventing, and/or managing various disorders, including, but not limited to, a disorder of the central nervous system. In one embodiment, the method comprises administering to a subject (e.g., human) a therapeutically or prophylactically effective amount of a composition or a compound provided herein. In one embodiment, the subject is a human. In one embodiment, the subject is an animal. In one embodiment, the compounds provided herein are highly brain penetrable in the subject. In certain embodiments, the efficacious concentration of the compounds provided herein is less than 10 nM, less than 100 nM, less than 1 μM, less than 10 μM, less than 100 μM, or less than 1 mM. In one embodiment, the compound's activity may be assessed in various art-recognized animal models as described herein elsewhere or known in the literature.

In one embodiment, without being limited by a particular theory, the treatment, prevention, and/or management is done by administering a compound provided herein that has shown in vivo efficacy in an animal model predictive of efficacy in humans.

In one embodiment, provided herein is a method of treating, preventing, and/or managing a disorder related to a CNS disorder, a neurological disorder, schizophrenia, a schizophrenia-related disorder, schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, psychosis, a disease having a psychosis component, psychotic disorder, brief psychotic disorder, Alzheimer's psychosis, Parkinson's psychosis, shared psychotic disorder, substance-induced psychotic disorder (e.g., cocaine, alcohol, amphetamine), psychotic disorder due to a general medical condition, psychoaffective disorder, aggression, delirium, excitative psychosis, Tourette's syndrome, manic disorder, organic psychosis, NOS psychosis, convulsion, seizure, agitation, posttraumatic stress disorder, behavior disorder, neurodegenerative disease, Huntington's disease, Alzheimer's disease, Parkinson's disease, dyskinesias, dementia, mood disorder, bipolar disorder, anxiety, depression, major depressive disorder, unipolar depression, treatment resistant depression, dysthymia, affective disorder, seasonal affective disorder, obsessive-compulsive disorder, attention deficit disorder (ADD), attention deficit hyperactivity disorder (ADHD), vertigo, pain, neuropathic pain, sensitization accompanying neuropathic pain, inflammatory pain, fibromyalgia, migraine, cognitive impairment, cognitive impairment associated with schizophrenia, cognitive deficit in Alzheimer's disease, cognitive deficit in Parkinson's disease, movement disorder, restless leg syndrome (RLS), multiple sclerosis, sleep disorder, substance abuse or dependency (e.g., nicotine, cocaine), addiction, eating disorder, autism, obesity, undesirable weight retention or weight gain, metabolic syndrome, diabetes, non-insulin dependent diabetes, impaired glucose tolerance, or hyperglycemia, comprising administering to a subject an effective amount of a compound provided herein. In one embodiment, provided herein is a method of treating, preventing, and/or managing a disorder selected from schizophrenia, cognitive impairment associated with schizophrenia, cognitive impairment, psychosis, depression, and Huntington's disease, comprising administering to a subject an effective amount of a compound provided herein.

In one embodiment, provided herein is a method of treating, preventing, and/or managing a neurological disorder as provided herein elsewhere, such as schizophrenia, psychosis, cognitive impairment, depression, Alzheimer's disease, Parkinson's disease, and attention deficit hyperactivity disorder (ADHD), and the like, comprising administering to a subject an effective amount of a compound provided herein.

In one embodiment, provided herein is a method of treating, preventing, and/or managing schizophrenia or a schizophrenia-related disorder, including but not limited to schizophrenia spectrum disorder, acute schizophrenia, chronic schizophrenia, NOS schizophrenia, schizoaffective disorder, schizophreniform disorder, paraphrenia, paranoid personality disorder, schizoid personality disorder, schizotypal personality disorder, delusional disorder, and psychosis, comprising administering to a subject an effective amount of a compound provided herein. In one embodiment, the compounds provided herein treat, prevent, and/or ameliorate one or more positive symptoms of schizophrenia. In one embodiment, the compounds provided herein treat, prevent, and/or ameliorate one or more negative symptoms of schizophrenia. In one embodiment, the compounds provided herein treat, prevent, and/or ameliorate one or more cognitive symptoms of schizophrenia.

In one embodiment, provided herein is a method of treating, preventing, and/or managing a disease having a psychosis component, including but not limited to psychotic disorder, brief psychotic disorder, Alzheimer's psychosis, Parkinson's psychosis, shared psychotic disorder, substance-induced psychotic disorder (e.g., cocaine, alcohol, or amphetamine), psychotic disorder due to a general medical condition, psychoaffective disorder, aggression, delirium, excitative psychosis, Tourette's syndrome, manic disorder, organic psychosis, and NOS psychosis, comprising administering to a subject an effective amount of a compound provided herein.

In one embodiment, provided herein is a method of treating, preventing, and/or managing cognitive impairment, including but not limited to cognitive impairment associated with schizophrenia, cognitive deficit in Alzheimer's disease, cognitive deficit in Parkinson's disease, comprising administering to a subject an effective amount of a compound provided herein.

In one embodiment, provided herein is a method of treating, preventing, and/or managing mood disorder, bipolar disorder, anxiety, depression, major depressive disorder, unipolar depression, treatment resistant depression, dysthymia, affective disorder, seasonal affective disorder, or obsessive-compulsive disorder, comprising administering to a subject an effective amount of a compound provided herein.

In one embodiment, provided herein is a method of treating, preventing, and/or managing attention deficit disorder (ADD) or attention deficit hyperactivity disorder (ADHD), comprising administering to a subject an effective amount of a compound provided herein.

In one embodiment, provided herein is a method of treating, preventing, and/or managing a neurodegenerative disease, including but not limited to Huntington's disease, Alzheimer's disease, and Parkinson's disease, comprising administering to a subject an effective amount of a compound provided herein. In one embodiment, provided herein is a method of treating, preventing, and/or managing Huntington's disease, comprising administering to a subject an effective amount of a compound provided herein.

In one embodiment, provided herein is a method of treating, preventing, and/or managing agitation, posttraumatic stress disorder, or behavior disorder, comprising administering to a subject an effective amount of a compound provided herein.

In one embodiment, provided herein is a method of treating, preventing, and/or managing dementia, comprising administering to a subject an effective amount of a compound provided herein.

In one embodiment, provided herein is a method of treating, preventing, and/or managing vertigo, comprising administering to a subject an effective amount of a compound provided herein.

In one embodiment, provided herein is a method of treating, preventing, and/or managing pain, neuropathic pain, sensitization accompanying neuropathic pain, inflammatory pain, migraine or fibromyalgia, comprising administering to a subject an effective amount of a compound provided herein.

In one embodiment, provided herein is a method of treating, preventing, and/or managing movement disorder or restless leg syndrome (RLS), comprising administering to a subject an effective amount of a compound provided herein.

In one embodiment, provided herein is a method of treating, preventing, and/or managing multiple sclerosis, sleep disorder, substance abuse or dependency (e.g., nicotine, cocaine), addiction, eating disorder, or autism, comprising administering to a subject an effective amount of a compound provided herein.

In one embodiment, provided herein is a method of treating, preventing, and/or managing a disorder related to cognitive impairments, such as those associated with Alzheimer's disease, Parkinson's disease, schizophrenia, and attention deficit hyperactivity disorder (ADHD), and the like, comprising administering to a subject an effective amount of a compound provided herein. For example, without being limited by a particular theory, the compounds provided herein may have pro-cognitive effects, such as passive avoidance, novel object recognition, social recognition, and attention-set shifting. Further, without being limited by a particular theory, the compounds provided herein may improve social memory, increase the acquisition of an environment, and reverse scopolamine-induced deficits. The compounds provided herein may also reverse scopolamine-induced deficits in a passive avoidance memory test.

In one embodiment, provided herein is a method of treating, preventing, and/or managing a psychotic disorder or psychotic condition, including but not limited to, schizophrenia, delusional disorders and drug induced psychosis, comprising administering to a subject an effective amount of a compound provided herein.

In one embodiment, provided herein is a method of treating, preventing, and/or managing an anxiety disorder, including but not limited to, panic and obsessive-compulsive disorder, comprising administering to a subject an effective amount of a compound provided herein.

In one embodiment, provided herein is a method of treating, preventing, and/or managing a movement disorder, including but not limited to, Parkinson's disease and Huntington's disease, comprising administering to a subject an effective amount of a compound provided herein.

In one embodiment, the psychotic disorders provided herein that can be treated, prevented, and/or managed using a compound or a pharmaceutical composition provided herein include, but are not limited to, schizophrenia, e.g., of the paranoid, disorganized, catatonic, undifferentiated, and/or residual type; schizophreniform disorder; schizoaffective disorder, e.g., of the delusional and/or depressive type; delusional disorder; substance-induced psychotic disorder, e.g., psychosis induced by alcohol, amphetamine, *cannabis*, cocaine, hallucinogens, inhalants, opioids, and/or phencyclidine; personality disorder of the paranoid type; and personality disorder of the schizoid type.

In one embodiment, the movement disorders provided herein that can be treated, prevented, and/or managed using a compound or a pharmaceutical composition provided herein include, but are not limited to, Huntington's disease, dyskinesia associated with dopamine agonist therapy, Parkinson's disease, restless leg syndrome, and essential tremor.

In one embodiment, other disorders provided herein that can be treated, prevented, and/or managed using a compound or a pharmaceutical composition provided herein include, but are not limited to, obsessive-compulsive disorder, Tourette's syndrome, and tic disorders.

In one embodiment, provided herein is a method of treating, preventing, and/or managing an anxiety disorder, including but not limited to, panic disorder, agoraphobia, specific phobia, social phobia, obsessive-compulsive disorder, post-traumatic stress disorder, acute stress disorder, and generalized anxiety disorder, comprising administering to a subject an effective amount of a compound provided herein.

In one embodiment, provided herein is a method of treating, preventing, and/or managing a drug addiction, including but not limited to, an alcohol, amphetamine, cocaine, and/or opiate addiction, comprising administering to a subject an effective amount of a compound provided herein. In one embodiment, the drug addiction provided herein represents an abnormal desire for a drug and is generally characterized by motivational disturbances such a compulsion to take the desired drug and episodes of intense drug craving.

In one embodiment, provided herein is a method of treating, preventing, and/or managing a disorder comprising a symptom of deficiency in attention and/or cognition, comprising administering to a subject an effective amount of a compound provided herein. In one embodiment, deficiency in attention and/or cognition provided herein may represent a subnormal functioning in one or more cognitive aspects, such as, e.g., memory, intellect, learning ability, and/or logic ability, in a particular subject relative to other subjects within the same general population and/or age group. In one embodiment, deficiency in attention and/or cognition provided herein may represent a reduction in a particular sub-population's functioning in one or more cognitive aspects, such as, e.g., in age-related cognitive decline.

In one embodiment, the disorders comprising a symptom of deficiency in attention and/or cognition provided herein that can be treated, prevented, and/or managed with a compound or a pharmaceutical composition provided herein, include, but are not limited to, dementia, e.g., dementia in Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, or AIDS-related dementia; delirium; amnestic disorder; post-traumatic stress disorder; mental retardation; learning disorder, e.g., reading disorder, mathematics disorder, or a disorder of written expression; attention-deficit/hyperactivity disorder; and age-related cognitive decline.

In one embodiment, provided herein is a method of treating, preventing, and/or managing a mood disorder or a mood episode, comprising administering to a subject an effective amount of a compound provided herein. In one embodiment, the mood disorders or mood episodes provided herein that can be treated, prevented, and/or managed with a compound or a pharmaceutical composition provided herein include, but are not limited to, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; treatment resistant depression; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, e.g., bipolar I disorder, bipolar II disorder, and cyclothymic disorder.

In one embodiment, provided herein is a method of treating, preventing, and/or managing a neurodegenerative disorder or neurodegenerative condition, comprising administering to a subject an effective amount of a compound provided herein. In one embodiment, the neurodegenerative disorder or neurodegenerative condition provided herein that can be treated, prevented, and/or managed with a compound or a pharmaceutical composition provided herein represents a disorder or condition that is caused by the dysfunction and/or death of neurons in the central nervous system. The treatment of these disorders and conditions can be facilitated by administration of an agent which prevents the dysfunction or death of neurons at risk and/or enhances the function of damaged or healthy neurons to compensate for the loss of function caused by the dysfunction or death of at-risk neurons. In one embodiment, the neurodegenerative disorders or neurodegenerative conditions provided herein that can be treated, prevented, and/or managed with a compound or a pharmaceutical composition provided herein include, but are not limited to, Parkinson's disease; Huntington's disease; dementia, e.g., Alzheimer's disease, multi-infarct dementia, AIDS-related dementia, and Fronto temperal dementia; neurodegeneration associated with cerebral trauma; neurodegeneration associated with stroke; neurodegeneration associated with cerebral infarct; hypoglycemia-induced neurodegeneration; neurodegeneration associated with neurotoxin poisoning; and multi-system atrophy. In one embodiment, the neurodegenerative disorders or neurodegenerative conditions provided herein comprise neurodegeneration of striatal medium spiny neurons in a subject. In one embodiment, the neurodegenerative disorder or neurodegenerative condition is Huntington's disease.

In one embodiment, provided herein is a method of treating, preventing, and/or managing psychotic disorder, delusional disorder, drug induced psychosis, anxiety disorder, movement disorder, mood disorder, neurodegenerative disorder, or drug addiction, comprising administering to a subject an effective amount of a compound provided herein.

In one embodiment, provided herein is a method of treating, preventing, and/or managing a neurologic disorder, including but not limited to, dementia, Alzheimer's disease, multi-infarct dementia, alcoholic dementia, drug-related dementia, dementia associated with intracranial tumors, dementia associated with cerebral trauma, dementia associated with Huntington's disease, dementia associated with Parkinson's disease, AIDS-related dementia, delirium, amnestic disorder, post-traumatic stress disorder, mental retardation, learning disorder, reading disorder, mathematics disorder, disorder of written expression, attention-deficit-hyperactivity disorder, age-related cognitive decline, major depressive episode of the mild, moderate or severe type, manic or mixed mood episode, hypomanic mood episode, depressive episode with atypical features, depressive episode with melancholic features, depressive episode with catatonic features, mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder comprising a delusional disorder or schizophrenia, bipolar disorder, bipolar I disorder, bipolar II disorder, cyclothymic disorder, Parkinson's disease, Huntington's disease, dementia, Alzheimer's disease, multi-infarct dementia, AIDS-related dementia, Fronto temperal dementia, neurodegeneration associated with cerebral trauma, neurodegeneration associated with stroke, neurodegeneration associated with cerebral infarct, hypoglycemia-induced neurodegeneration, neurodegeneration associated with neurotoxin poisoning, multi-system atrophy, schizophrenia of a paranoid, disorganized, catatonic, undifferentiated or residual type, schizophreniform disorder; schizoaffective disorder of the delusional type or the depressive type, delusional disorder, substance-induced psychotic disorder, psychosis induced by alcohol, amphetamine, *cannabis*, cocaine, hallucinogens, inhalants, opioids, or phencyclidine, personality disorder of the paranoid type, and personality disorder of the schizoid type, comprising administering to a subject an effective amount of a compound provided herein.

In one embodiment, provided herein is a method of treating, preventing, and/or managing a neurologic disorder, including but not limited to, psychotic disorders, delusional disorders, drug induced psychosis, anxiety disorders, movement disorders, mood disorders, neurodegenerative disorders, and drug addiction, comprising administering to a subject an effective amount of a compound provided herein.

In one embodiment, provided herein is a method of treating, preventing, and/or managing substance abuse, comprising administering to a subject an effective amount of a compound provided herein. For example, without being limited by a particular theory, the compounds provided herein may alter methamphetamine self-administration in rats, and therefore the compounds provided herein may ameliorate the craving for addictive drugs.

In one embodiment, provided herein is a method of using the compounds provided herein as psycho-stimulants, which may lack the abuse liabilities generally associated with other classes of psycho-stimulants.

In one embodiment, provided herein is a method of treating, preventing, and/or managing movement disorders, such as Parkinson's disease, L-dopa induced dyskineasias, peak dose dyskinesas, restless leg syndrome (RLS), and Huntington's disease, comprising administering to a subject an effective amount of a compound provided herein.

In some embodiments, the compounds provided herein are active in at least one model, which can be used to measure the activity of the compounds and estimate their efficacy in treating a CNS disorder. For example, the compounds provided herein are active in at least one model for schizophrenia, such as, e.g., conditioned avoidance responding, amphetamine-induced deficit in auditory gating, phencyclidine-induced hyperlocomotion or hyperactivity, and amphetamine-induced hyperactivity models. The compounds are active when they induce a desired response in the animal (e.g., mice) by a statistically significant amount compared to vehicle-treated animals.

In other embodiments, provided herein is a method of effecting a therapeutic effect as described herein elsewhere. The method comprises administering to a subject (e.g., a mammal) a therapeutically effective amount of a compound or a composition provided herein. The particular therapeutic effects may be measured using any model system known in the art and described herein, such as those involving an animal model of a disease.

In some embodiments, the neurological disorder provided herein is: depression (e.g., major depressive disorder, bipolar disorder, unipolar disorder, treatment resistant depression, dysthymia, and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; and substance abuse or dependency (e.g., cocaine addiction, nicotine addiction). In another embodiment, the compounds provided herein are useful to treat, prevent, and/or manage two or more conditions/disorders, which are co-morbid, such as psychosis and depression.

Neurological disorders may also include cerebral function disorders, including without limitation, senile dementia, Alzheimer's type dementia, cognition, memory loss, amnesia/amnestic syndrome, lowering of attention, speech disorders, autism, and hyperkinetic syndrome.

Neuropathic pain includes, without limitation, post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity, overweight, metabolic syndrome, diabetes, non-insulin dependent diabetes, impaired glucose tolerance, and hyperglycemia.

In one embodiment, the neurological disorder is excessive daytime sleepiness. In another embodiment, the neurological disorder is cognitive impairment. In another embodiment, the neurological disorder is mood disorders. In another embodiment, the neurological disorder is movement disorders. In another embodiment, the neurological disorder is schizophrenia. In another embodiment, the neurological disorder is attention disorders. In another embodiment, the neurological disorder is anxiety disorder. In another embodiment, the neurological disorder is seizure. In another embodiment, the neurological disorder is psychosis. In another embodiment, the neurological disorder is vertigo. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. The dosage may be formulated as a single or multiple unit dosage formulation. In one embodiment, the compound is given in single or divided doses per day.

In some embodiments, the compounds disclosed herein may be used in combination with one or more second active agents to treat, prevent, and/or manage disorders described herein (e.g., administered to a subject need thereof). In certain embodiments, the second active agent is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is an antidepressant agent. In certain embodiments, the second active agent is selected from an SSRI, SNRI, and tricyclic antidepressants. In certain embodiments, the second active agent is lurasidone, olanzapine, risperidone, aripiprazole, amisulpride, asenapine, blonanserin, clozapine, clotiapine, illoperidone, mosapramine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, venlafaxine, duloxetine, or L-DOPA.

3. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients (e.g., a second active agent provided herein elsewhere). Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences*, 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising, active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In other embodiments, dosage forms comprise the second active ingredient. The specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy,* 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

A. General Procedures for Compound Synthesis

In the examples below, unless otherwise indicated, all temperatures are set forth in degrees Celsius and all parts and percentages are by weight. Reagents may be purchased from commercial suppliers, such as Sigma-Aldrich® Chemical Company, and may be used without further purification unless otherwise indicated. Reagents may also be prepared following standard literature procedures known to those skilled in the art. Solvents may be purchased from Aldrich in Sure-Seal® bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates and eluted with appropriate solvent ratios (v/v). Reactions were assayed by TLC or liquid chromatography mass spectroscopy (LCMS), and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (see, e.g., Still et al., *J. Org. Chem.,* 43: 2923 (1978)) was performed using silica gel 60 or various medium-pressure liquid chromatography (MPLC) systems (such as Biotage® or ISCO® separation systems).

The compound structures in the examples below were confirmed by one or more of the following methods: proton magnetic resonance spectroscopy, mass spectroscopy, elemental microanalysis, and melting point. Proton nuclear magnetic resonance ($^1H$ NMR) spectra were determined using a NMR spectrometer operating at a certain field strength. Chemical shifts are reported in parts per million (ppm, δ) downfield from an internal standard, such as tetramethylsilane (TMS). Alternatively, $^1H$ NMR spectra were referenced to signals from residual protons in deuterated solvents as follows: $CDCl_3$=7.25 ppm; $DMSO\text{-}d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

1. General Procedure A

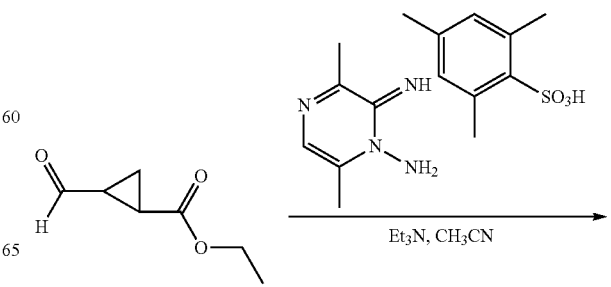

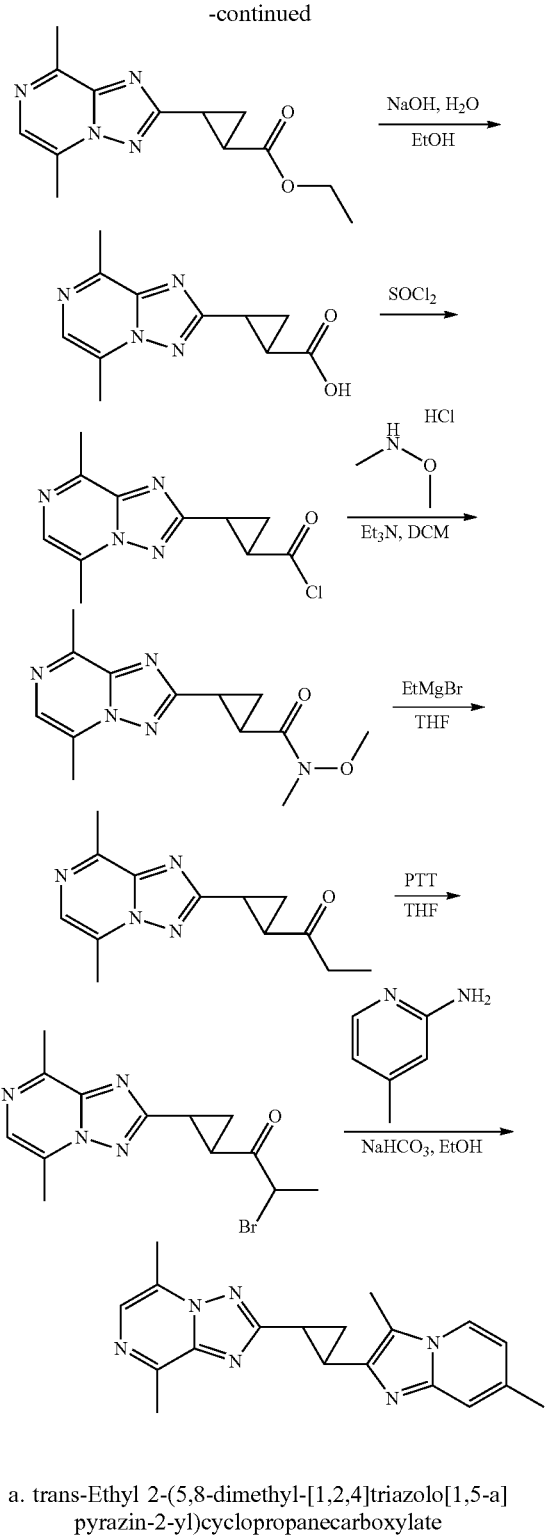

a. trans-Ethyl 2-(5,8-dimethyl-[1,2,4]triazolo[1,5-a]pyrazin-2-yl)cyclopropanecarboxylate A mixture of 2-imino-3,6-dimethylpyrazin-1(2H)-amine 2,4,6-trimethylbenzenesulfonate (10.1 g, 30 mmol) and TEA (8.08 g, 80 mmol) in CH$_3$CN (100 mL) was heated to 70° C., trans-ethyl 2-formylcyclopropanecarboxylate (2.84 g, 20 mmol) was added. The resulting mixture was stirred at 70° C. for 2 hours. The solvent was removed and water was added. The aqueous was extracted with EtOAc (50 mL×3), the combined organic phase was washed with brine, dried with sodium sulfate and concentrated in vacuo. The crude product was purified by chromatography (PE:EtOAc=5:1) to give ethyl 2-(5,8-dimethyl-[1,2,4]triazolo[1,5-a]pyrazin-2-yl) cyclopropane carboxylate (3.0 g, 58%) as a yellow solid. MS (ESI): m/z 261 [M+1]$^+$. $^1$H NMR (400 MHz, CDCl$_3$) δ 7.82 (d, J=2.0H, 1H), 4.18 (q, J=7.6, 14.4 Hz, 2H), 2.86-2.89 (m, 1H), 2.84 (s, 3H), 2.69 (s, 3H), 2.35-2.37 (m, 1H), 1.73 (t, J=7.2 Hz, 2H), 1.28 (t, J=7.2 Hz, 3H).

b. 2-(5,8-Dimethyl-[1,2,4]triazolo[1,5-a]pyrazin-2-yl)cyclopropanecarboxylic acid A mixture of ethyl 2-(5,8-dimethyl-[1,2,4]triazolo[1,5-a]pyrazin-2-yl)cyclopropane carboxylate (3.0 g, 11.5 mmol) in EtOH (40 mL) was stirred at room temperature, a solution of sodium hydroxide (920 mg, 23 mmol) in water (10 mL) was added. The resulting mixture was stirred at room temperature overnight. The solvent was removed, the aqueous was adjusted pH=5 with concentrated hydrochloride. The solid was filtered and dried to give 2-(5,8-dimethyl-[1,2,4]triazolo[1,5-a]pyrazin-2-yl)cyclopropanecarboxylic acid (2.58 g, 97%) as a yellow solid. MS (ESI): m/z 233 [M+1]$^+$. $^1$H NMR (400 MHz, DMSO) δ 7.94 (s, 1H), 2.69 (s, 3H), 2.63-2.67 (m, 1H), 2.62 (s, 3H), 2.09-2.14 (m, 1H), 1.54-1.58 (m, 2H).

c. 2-(5,8-Dimethyl-[1,2,4]triazolo[1,5-a]pyrazin-2-yl)cyclopropanecarbonyl chloride A mixture of 2-(5,8-dimethyl-[1,2,4]triazolo[1,5-a]pyrazin-2-yl) cyclopropanecarboxylic acid (1.95 g, 8.4 mmol) in sulfurous dichloride (10 mL) was stirred at room temperature for 1 hour. The reaction mixture was concentrated in vacuum to give crude 2-(5,8-dimethyl-[1,2,4]triazolo[1,5-a]pyrazin-2-yl) cyclopropanecarbonyl chloride (2.1 g, 100%) for the next step immediately.

d. 2-(5,8-Dimethyl-[1,2,4]triazolo[1,5-a]pyrazin-2-yl)-N-methoxy-N-methylcyclopropanecarboxamide A mixture of N,O-dimethylhydroxylamine hydrochloride (815 mg, 8.4 mmol) and TEA (1.7 g, 16.8 mmol) in DCM (50 mL) was stirred at 0° C., a solution of 2-(5,8-dimethyl-[1,2,4]triazolo[1,5-a]pyrazin-2-yl) cyclopropane carbonyl chloride (2.1 g, 8.4 mmol) in DCM was added. The resulting mixture was stirred at room temperature for 2 hours. Water was added and the aqueous was extracted with DCM (50 mL×3), the combined organic phase was washed with brine, dried with sodium sulfate and concentrated. The crude product was purified by chromatography (PE:EtOAc=1:1) to give 2-(5,8-dimethyl-[1,2,4]triazolo[1,5-a]pyrazin-2-yl)-N-methoxy-N-methylcyclopropanecarboxamide (1.55 g, 67%) as a yellow solid. MS (ESI): m/z 276 [M+1]$^+$. $^1$H NMR (400 MHz, CDCl$_3$) δ 7.81 (d, J=0.4 Hz, 1H), 3.74 (s, 3H), 3.25 (s, 3H), 2.85-2.87 (m, 2H), 2.70 (s, 3H), 1.65-1.82 (m, 2H).

e. 1-(2-(5,8-Dimethyl-[1,2,4]triazolo[1,5-a]pyrazin-2-yl)cyclopropyl)propan-1-one A mixture of 2-(5,8-dimethyl-[1,2,4]triazolo[1,5-a]pyrazin-2-yl)-N-methoxy-N-methylcyclopropanecarboxamide (1.55 g, 5.6 mmol) in THF (30 mL) was stirred at 0° C., a solution of ethylmagnesium bromide in THF (1.0 M, 8.4 mL, 8.4 mmol) was added slowly. The resulting mixture was stirred at room temperature for 2 hours. A saturated solution of ammoniumchloride and the aqueous layer was extracted with EtOAc (50 mL×3), the combined organic phase was washed with brine, dried with sodium sulfate and concentrated. The crude product was purified by chromatography (PE:EtOAc=1:1) to give 1-(2-(5,8-dimethyl-[1,2,4]triazolo[1,5-a]pyrazin-2-yl)cyclopropyl)propan-1-one (1.0 g, 73%) as a yellow solid. MS (ESI): m/z 245 [M+1]+. 1H NMR (400 MHz, CDCl3) δ 7.85 (s, 1H), 2.86-2.91 (m, 1H), 2.85 (s, 3H), 2.70 (s, 3H), 2.63-2.68 (m, 3H), 1.72-1.76 (m, 2H), 1.12 (t, J=7.2 Hz, 3H).

f. 2-Bromo-1-(2-(5,8-dimethyl-[1,2,4]triazolo[1,5-a]pyrazin-2-yl)cyclopropyl) propan-1-one A mixture of 1-(2-(5,8-dimethyl-[1,2,4]triazolo[1,5-a]pyrazin-2-yl)cyclopropyl)propan-1-one (530 mg, 2.2 mmol) in THF (20 mL) was heated 40° C., PTT (1.24 g, 3.3 mmol) was added. The resulting mixture was stirred overnight. Water was added and the aqueous was extracted with EtOAc (20 mL×3), the combined organic phase was washed with brine, dried with sodium sulfate and concentrated. The crude product was purified by chromatography (PE:EtOAc=2:1) to give 2-bromo-1-(2-(5,8-dimethyl-[1,2,4]triazolo[1,5-a]pyrazin-2-yl)cyclopropyl) propan-1-one (438 mg, 62%) as a yellow solid. MS (ESI): m/z 323 [M+1]+.

g. 2-(2-(3,7-Dimethylimidazo[1,2-a]pyridin-2-yl)cyclopropyl)-5,8-dimethyl-[1,2,4]triazolo[1,5-a]pyrazine A mixture of 2-bromo-1-(2-(5,8-dimethyl-[1,2,4]triazolo[1,5-a]pyrazin-2-yl)cyclopropyl)propan-1-one (64 mg, 0.2 mmol), 4-methylpyridin-2-amine (32 mg, 0.3 mmol) and sodium bicarbonate (17 mg, 0.2 mmol) in EtOH (1 mL) was heated 80° C. and stirred overnight. The solvent was removed, water was added and the aqueous was extracted with EtOAc (10 mL×3). The combined organic phase was washed with brine, dried with sodium and concentrated. The crude product was purified by Prep-TLC (DCM:MeOH=20:1) to give the title compound (20 mg, 30%) as a yellow solid.

2. General Procedure B

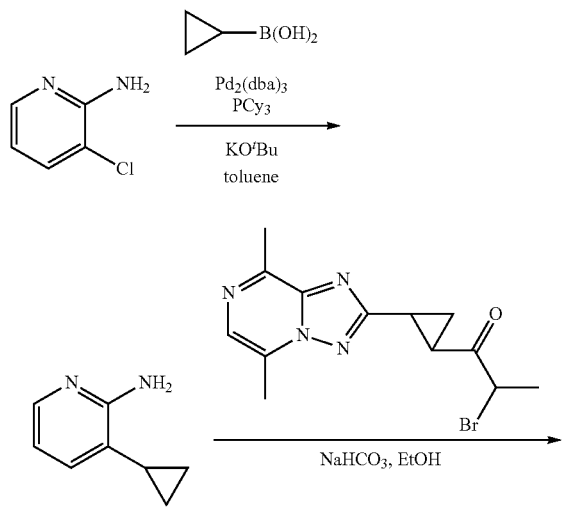

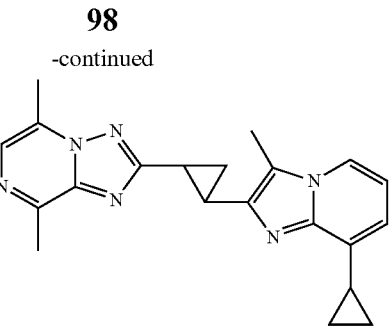

a. 3-Cyclopropylpyridin-2-amine

A mixture of 3-chloropyridin-2-amine (384 mg, 3 mmol), cyclopropylboronic acid (516 mg, 6 mmol), tris(dibenzylideneacetone)dipalladium(0) (275 mg, 0.3 mmol), tricyclohexylphosphine (168 mg, 0.6 mmol) and potassium tert-butoxide (672 mg, 6 mmol) in toluene (10 mL) was heated to 120° C. and stirred for 2 days. The solvent was removed, water was added and the aqueous was extracted with EtOAc (20 mL×3), the combined organic phase was washed with brine, dried with sodium sulfate and concentrated. The crude product was purified by reverse phase chromatography (30% CH3CN in water with 1% ammonium hydroxide) to give 3-cyclopropylpyridin-2-amine (50 mg, 12%) as a yellow oil. MS (ESI): m/z 135 [M+1]+.

b. 2-(2-(8-Cyclopropyl-3-methylimidazo[1,2-a]pyridin-2-yl)cyclopropyl)-5,8-dimethyl-[1,2,4]triazolo[1,5-a]pyrazine A mixture of 2-bromo-1-(2-(5,8-dimethyl-[1,2,4]triazolo[1,5-a]pyrazin-2-yl)cyclopropyl)propan-1-one (General procedure 1f, 48 mg, 0.15 mmol), 3-cyclopropylpyridin-2-amine (24 mg, 0.18 mmol) and sodium bicarbonate (13 mg, 0.15 mmol) in EtOH (1 mL) was heated 80° C. and stirred overnight. The solvent was removed, water was added and the aqueous was extracted with EtOAc (10 mL×3). The combined organic phase was washed with brine, dried with sodium and concentrated. The crude product was purified by Prep-TLC (DCM:MeOH=20:1) to give the title compound (10 mg, 19%) as a yellow solid.

3. General Procedure C

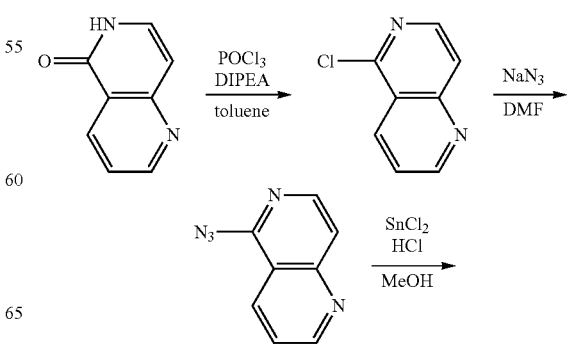

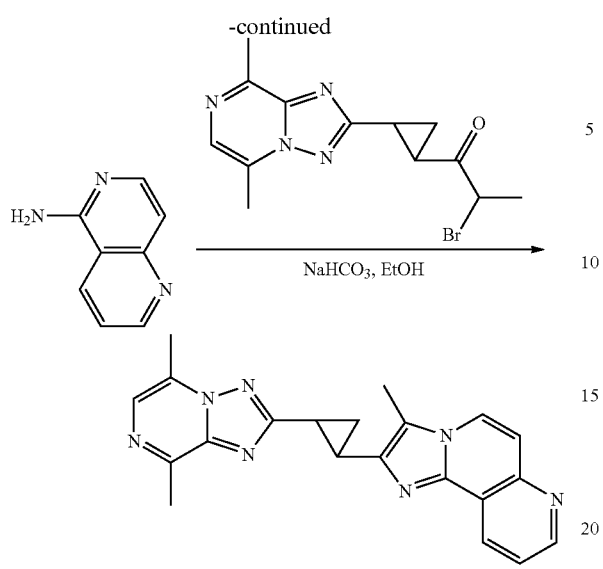

a. 5-Chloro-1,6-naphthyridine

A mixture of 1,6-naphthyridin-5(6H)-one (1.46 g, 10 mmol) in toluene (50 mL) was stirred at 0° C., phosphoryl trichloride (16 g, 100 mmol) was added, then N,N-diisopropylethylamine (6.45 g, 50 mmol) was added. The resulting mixture was heated to 100° C. and stirred overnight. The solvent was removed and the residue was diluted with DCM, the mixture was adjusted pH=8 with a saturated solution of sodium bicarbonate. The separated organic phase was washed with brine, dried with sodium sulfate and concentrated. The crude product was purified by chromatography (PE:EtOAc=2:1) to give 5-chloro-1,6-naphthyridine (400 mg, 24%) as a yellow solid. MS (ESI): m/z 165 [M+1]$^+$.

b. 5-Azido-1,6-naphthyridine

A mixture of 5-chloro-1,6-naphthyridine (378 mg, 2.3 mmol) in DMF (10 mL) was stirred at room temperature, sodium azide (299 mg, 4.6 mmol) was added. The resulting mixture was heated to 80° C. and stirred overnight. Water was added and the aqueous was extracted with EtOAc (20 mL×3), the combined organic phase was washed with brine, dried with sodium sulfate and concentrated to give 5-azido-1,6-naphthyridine (282 mg, 72%) as a yellow solid. MS (ESI): m/z 172 [M+1]$^+$.

c. 1,6-Naphthyridin-5-amine

A mixture of 5-azido-1,6-naphthyridine (282 mg, 1.65 mmol) and concentrated hydrochloride (2 mL) in MeOH (10 mL) was stirred at room temperature, Stannous chloride dehydrate (1.56 g, 8.25 mmol) was added. The resulting mixture was heated to 60° C. and stirred for 4 hours. The solvent was removed, water was added and the aqueous was adjusted pH=8 with a saturated solution of sodium bicarbonate, The aqueous was extracted with DCM (20 mL×3), the combined organic phase was washed with brine, dried with sodium and concentrated to give 1,6-naphthyridin-5-amine (120 mg, 50%) as a yellow solid. MS (ESI): m/z 146 [M+1]$^+$. $^1$H NMR (400 MHz, CDCl$_3$) δ 9.07 (d, J=6.8 Hz, 1H), 8.20 (d, J=8.4 Hz, 1H), 8.14 (d, J=6.4 Hz, 1H), 7.44 (q, J=4.0, 8.0 Hz, 2H), 7.31 (d, J=6.0 Hz, 1H).

d. 2-(2-(5,8-Dimethyl-[1,2,4]triazolo[1,5-a]pyrazin-2-yl)cyclopropyl)-3-methylimidazo[2,1-f][1,6]naphthyridine A mixture of 2-bromo-1-(2-(5,8-dimethyl-[1,2,4]triazolo[1,5-a]pyrazin-2-yl)cyclopropyl)propan-1-one (General Procedure 1f, 48 mg, 0.15 mmol), 1,6-naphthyridin-5-amine (33 mg, 0.23 mmol) and sodium bicarbonate (13 mg, 0.15 mmol) in EtOH (1 mL) was heated 80° C. and stirred overnight. The solvent was removed, water was added and the aqueous was extracted with EtOAc (10 mL×3). The combined organic phase was washed with brine, dried with sodium and concentrated. The crude product was purified by Prep-TLC (DCM:MeOH=20:1) to give the title compound (10 mg, 18%) as a yellow solid.

4. General Procedure D

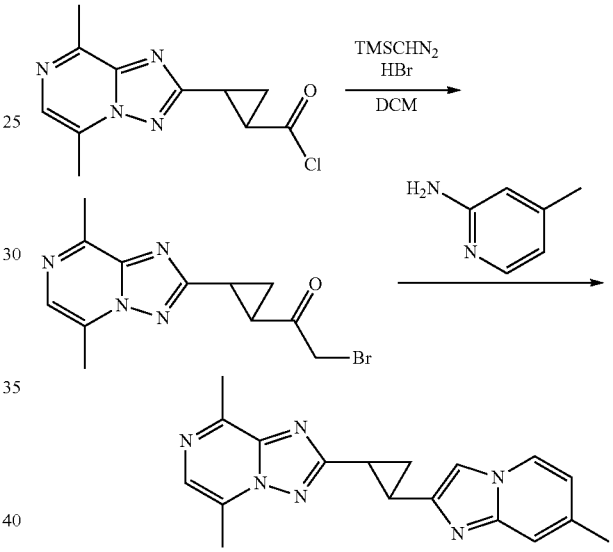

a. 2-(5,8-Dimethyl-[1,2,4]triazolo[1,5-a]pyrazin-2-yl)cyclopropanecarbonyl chloride The title compound was synthesized as described in General Procedure 1c.

b. 2-Bromo-1-(2-(5,8-dimethyl-[1,2,4]triazolo[1,5-a]pyrazin-2-yl)cyclopropyl)ethanone A mixture of 2-(5,8-dimethyl-[1,2,4]triazolo[1,5-a]pyrazin-2-yl)cyclopropanecarbonyl chloride (710 mg, 2.84 mmol) in DCM (10 mL) was stirred at 0° C., A solution of trimethylsilyldiazomethane in hexane (6 mL, 11.36 mmol) was added dropwise, The mixture was stirred at room temperature for 2 hours. The mixture was cooled to 0° C. and a 30% solution of hydrobromic acid in acetic acid (2 mL, 9.94 mmol) was added, the resulting mixture was stirred at room temperature for 1 hour. The reaction was adjusted pH=8 with the saturated solution of sodium bicarbonate and the aqueous was extracted with DCM (20 mL×3), the combined organic phase was washed with brine, dried with sodium sulfate and concentrated. The crude product was purified by chromatography (PE:EtOAc=5:1) to give 2-bromo-1-(2-(5,8-dimethyl-[1,2,4]triazolo[1,5-a]pyrazin- 2-yl)cyclopropyl) ethanone (400 mg, 40%) as a yellow solid. MS (ESI): m/z 349 [M+1]$^+$. $^1$H NMR (400 MHz, CDCl$_3$) δ 7.84 (d, J=1.2 Hz, 1H), 4.05-4.13 (m, 2H), 2.95-3.0 (m, 1H), 2.89-2.94 (m, 1H), 2.85 (s, 3H), 2.70 (s, 3H), 1.83-1.92 (m, 2H).

c. 5,8-Dimethyl-2-(2-(7-methylimidazo[1,2-a]pyridin-2-yl)cyclopropyl)-[1,2,4]triazolo[1,5-a]pyrazine A mixture of 2-bromo-1-(2-(5,8-dimethyl-[1,2,4]triazolo[1,5-a]pyrazin-2-yl)cyclopropyl)ethanone (61, 0.2 mmol), 4-methyl-pyridin-2-amine (33 mg, 0.31 mmol) and sodium bicarbonate (16 mg, 0.2 mmol) in EtOH (1 mL) was heated 80° C. and stirred overnight. The solvent was removed, water was added and the aqueous was extracted with EtOAc (10 mL×3). The combined organic phase was washed with brine, dried with sodium and concentrated. The crude product was purified by Prep-TLC (DCM:MeOH=30:1) to give the title compound (20 mg, 29%) as a yellow solid.

5. General Procedure E

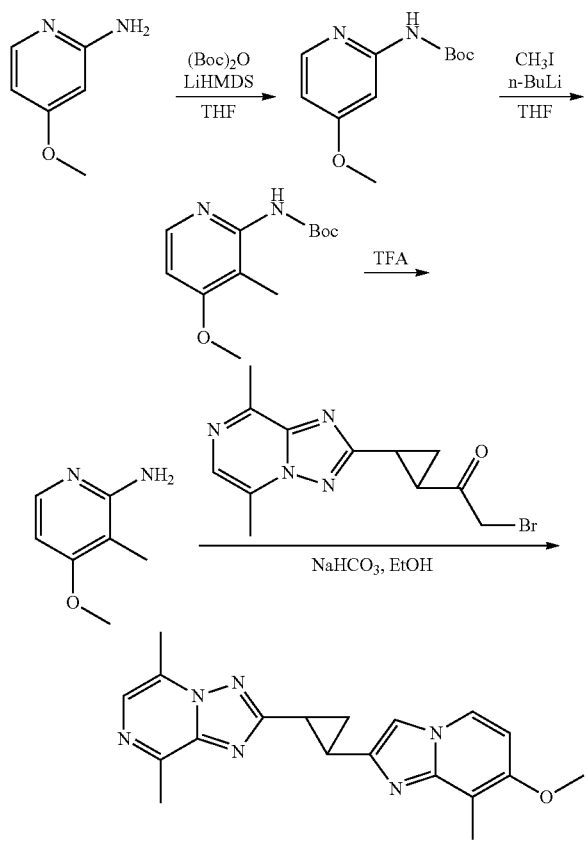

a. Tert-butyl 4-methoxypyridin-2-yl-carbamate

A mixture of 4-methoxypyridin-2-amine (1.24 g, 10 mmol) in THF (50 mL) was stirred at 0° C., a solution of lithium hexamethyldisilazide in THF (22 mL, 22 mmol, 1.0 M) was added slowly. The resulting mixture was stirred for 30 min. and then di-tert-butyl dicarbonate (2.26 g, 10.5 mmol) was added. The mixture was stirred at room temperature overnight. Water was added and the aqueous was extracted with EtOAc (50 mL×3), the combined organic phase was washed with brine, dried with sodium sulfate and concentrated. The crude product was purified by chromatography (PE:EtOAc=30:1) to give tert-butyl 4-methoxypyridin-2-ylcarbamate (1.8 g, 80%) as a white solid. MS (ESI): m/z 225 [M+1]$^+$. $^1$H NMR (400 MHz, CDCl$_3$) δ 9.77 (ds, 1H), 8.14 (q, J=2.8, 5.6 Hz, 1H), 7.62 (s, 1H), 6.50 (q, J=2.4, 6.0 Hz, 1H), 3.90 (s, 3H), 1.55 (s, 9H).

b. Tert-butyl 4-methoxy-3-methylpyridin-2-yl-carbamate

A mixture of tert-butyl 4-methoxypyridin-2-ylcarbamate (224 mg, 1 mmol) in THF (10 mL) was stirred at 0° C., a solution of n-butyllithium in hexane (1 mL, 2.5 mmol, 2.5 M) was added and the mixture was stirred for 1 hour. A solution of iodomethane in THF (170 mg, 1.2 mmol) was added, the resulting mixture was stirred at room temperature for 1 hour. A saturated solution of ammonium chloride was added and the aqueous was extracted with EtOAc (10 mL×3), the combined organic phase was washed with brine, dried over sodium sulfate and concentrated. The crude product was purified by Prep-TLC (PE:EtOAc=1:1) to give tert-butyl 4-methoxy-3-methylpyridin-2-ylcarbamate (120 mg, 50%) as a white solid. MS (ESI): m/z 239 [M+1]$^+$. $^1$H NMR (400 MHz, CDCl$_3$) δ 8.17 (d, J=5.6 Hz, 1H), 6.64 (d, J=5.6 Hz, 1H), 3.87 (s, 3H), 2.11 (s, 3H), 1.51 (s, 9H).

c. 4-Methoxy-3-methylpyridin-2-amine

A mixture of tert-butyl 4-methoxy-3-methylpyridin-2-ylcarbamate (120 mg, 0.5 mmol) and trifluoroacetic acid (1 mL) in DCM (5 mL) was stirred at room temperature for 2 hours. The reaction mixture was adjusted pH=8 with the saturated solution of sodium bicarbonate and the aqueous was extracted with DCM (20 mL×3), the combined organic phase was washed brine, dried with sodium sulfate and concentrated to give 4-methoxy-3-methylpyridin-2-amine (66 mg, 94%) as a yellow solid. MS (ESI): m/z 139 [M+1]$^+$.

d. 2-(2-(7-Methoxy-8-methylimidazo[1,2-a]pyridin-2-yl)cyclopropyl)-5,8-dimethyl-[1,2,4]triazolo[1,5-a]pyrazine A mixture of 2-bromo-1-(2-(5,8-dimethyl-[1,2,4]triazolo[1,5-a]pyrazin-2-yl)cyclopropyl)ethanone (General Procedure 4b, 61 mg, 0.2 mmol), 4-methoxy-3-methylpyridin-2-amine (33 mg, 0.24 mmol) and sodium bicarbonate (16 mg, 0.2 mmol) in EtOH (1 mL) was heated 80° C. and stirred overnight. The solvent was removed, water was added and the aqueous was extracted with EtOAc (10 mL×3). The combined organic phase was washed with brine, dried with sodium and concentrated. The crude product was purified by Prep-TLC (DCM:MeOH=30:1) to give the title compound (20 mg, 29%) as a yellow solid.

6. General Procedure F

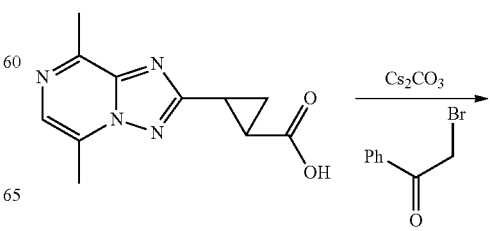

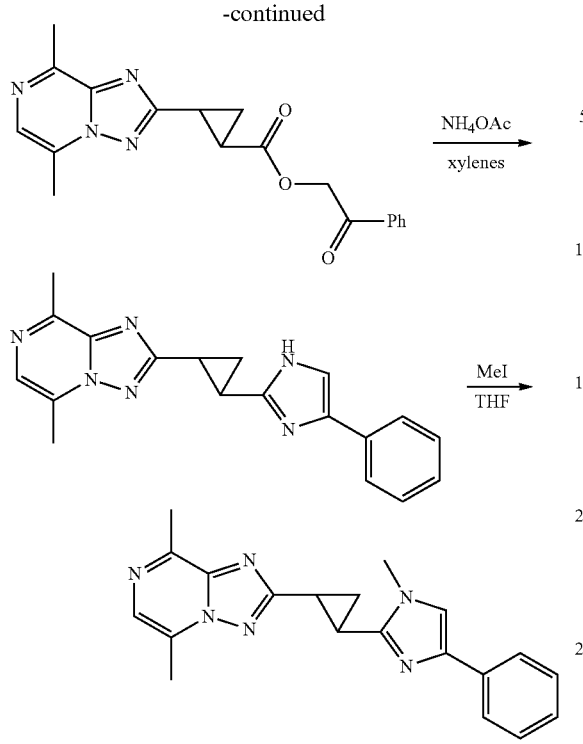

a. 2-Oxo-2-phenylethyl 2-(5,8-dimethyl-[1,2,4]triazolo[1,5-a]pyrazin-2-yl)cyclopropanecarboxylate To a solution of 2-(5,8-dimethyl-[1,2,4]triazolo[1,5-a]pyrazin-2-yl)cyclopropanecarboxylic acid (General Procedure 1b, 0.25 g, 1.1 mmol) in EtOH (11 mL) was added Cs$_2$CO$_3$ (0.35 g, 1.1 mmol) and the reaction mixture was allowed to stir for 1 h at 25° C. The volatiles were removed in vacuo and the resulting solid was suspended in DMF (11 ml) and treated with 2-bromoacetophenone (0.24 g, 1.2 mmol) and the yellow mixture was stirred at 25° C. for 16 h at which time the reaction mixture was poured into a separatory funnel, diluted with NaHCO$_3$ (sat. aq.) and extracted with EtOAc (3×50 mL). The resulting combined organics were washed with brine and dried over Na$_2$SO$_4$, filtered and the solvent removed in vacuo to afford 2-oxo-2-phenylethyl 2-(5,8-dimethyl-[1,2,4]triazolo[1,5-a]pyrazin-2-yl)cyclopropanecarboxylate which was used in the following step without further purification.

b. 5,8-Dimethyl-2-(2-(4-phenyl-1H-imidazol-2-yl)cyclopropyl)-[1,2,4]triazolo[1,5-a]pyrazine To 2-oxo-2-phenylethyl 2-(5,8-dimethyl-[1,2,4]triazolo[1,5-a]pyrazin-2-yl)cyclopropanecarboxylate (385 mg, 1.1 mmol) in a microwave reaction vial was added NH$_4$OAc (1 g) and 4 Å MS (2 g) and m-xylenes (15 mL) and the reaction vial was sealed with an aluminum crimped cap. The reaction mixture was heated to 150° C. for 30 minutes and after returning to room temperature the reaction mixture was placed directly on a silica gel column and eluted with 10% MeOH in EtOAc. The isolated compound was a mixture of regioisomeric phenyl imidazoles MS (ES+): m/z 331.31 [M+1]$^+$.

c. 5,8-Dimethyl-2-(2-(1-methyl-4-phenyl-1H-imidazol-2-yl)cyclopropyl)-[1,2,4]triazolo[1,5-a]pyrazine To the regioisomeric mixture of phenylimidazoles (112 mg, 0.34 mmol) in THF (3 ml) was added iodomethane (1 mL, 3 mmol) and the resulting reaction mixture was allowed to stir for 16 h. Upon reaction completion the volatiles were removed in vacuo and the resulting crude oil was taken up in MeOH (3 mL) and purified by RP-HPLC (10-50% gradient 0.1% formic acid/H$_2$O in acetonitrile). Lyophilization of the collected fractions afforded the title compound as the formate salt.

7. General Procedure G

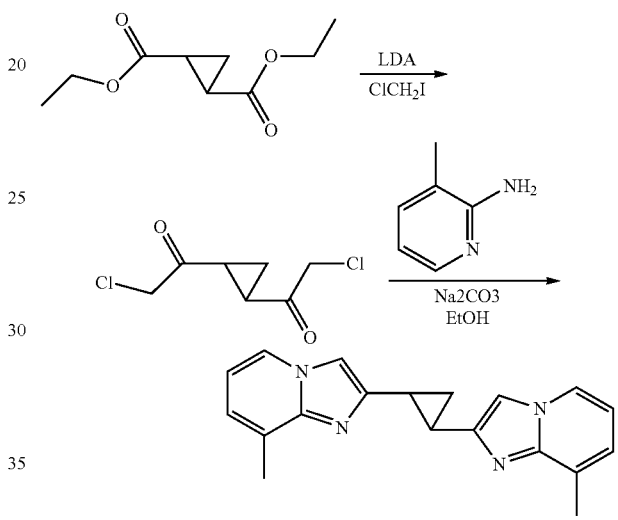

a. trans-1,1'-(Cyclopropane-1,2-di-yl)bis(2-chloroethanone)

To a solution of trans-diethyl cyclopropane-1,2-dicarboxylate (558 mg, 3 mmol) and chloroiodomethane (1.06 g, 6 mmol) in dry THF (20 mL) was added dropwise LDA (6 mL, 12 mmol) at −78° C. under nitrogen. After 2 h, the mixture was warmed to −30° C. AcOH (2.40 g, 40 mmol) was added dropwise to the reaction mixture. The mixture was stirred at 0° C. for additional 1 h. The mixture was diluted with water (100 mL) and extracted with EtOAc. The combined organic phase was concentrated in vacuum to give 1.2 g of the crude product, which was directly used for the next step without further purification.

b. 1,2-Bis(8-methylimidazo[1,2-a]pyridin-2-yl)cyclopropane

A solution of crude 1,1'-(cyclopropane-1,2-di-yl)bis(2-chloroethanone) (1.2 g, 3 mmol), Na$_2$CO$_3$ (106 mg, 1 mmol), and 3-methylpyridin-2-amine (216 mg, 2 mmol) in EtOH (20 mL) was stirred at reflux overnight. The mixture was diluted with water (30 mL) and extracted with EtOAc (20 mL×3). The combined organic phase was concentrated and purified by column chromatography on silica gel (DCM:CH$_3$OH=1:10) to obtain 25 mg of the desired product as a white colorless solid.

8. General Procedure H

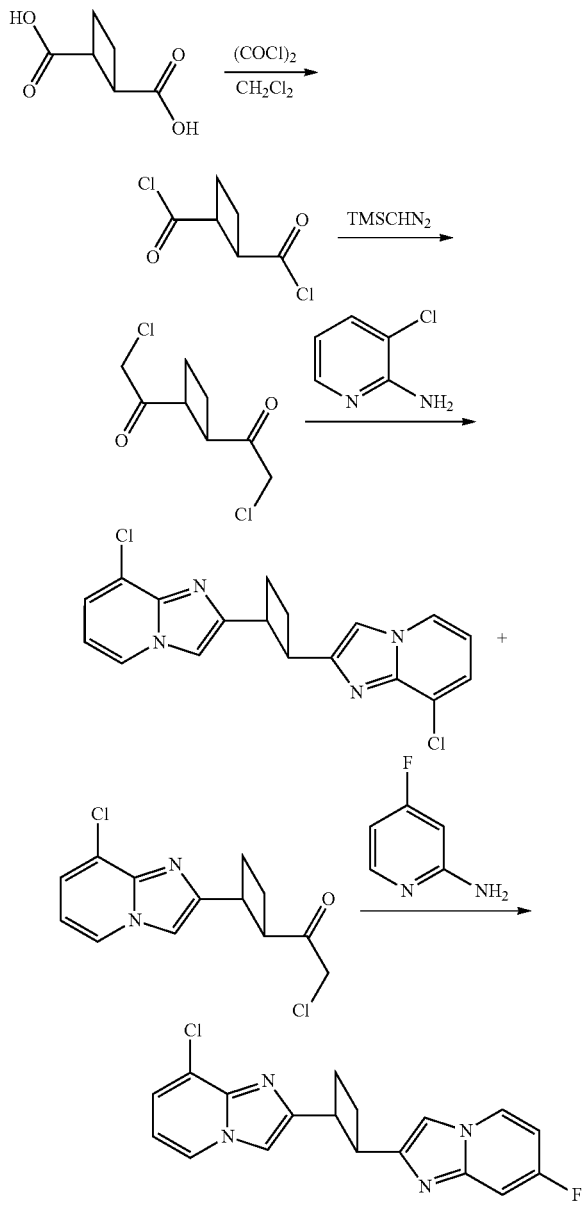

a. trans-Cyclobutane-1,2-dicarbonyl dichloride

To a solution of trans-cyclobutane-1,2-dicarboxylic acid (0.222 g, 1.54 mmol) in CH₂Cl₂ (10 mL) was added oxalyl chloride (1.7 mL, 3.39 mmol) and the resulting reaction mixture was stirred at 25° C. for 2 h at which time the volatiles were removed in vacuo and the resulting oil was used in the following step without further purification.

b. trans-1,1'-(Cyclobutane-1,2-di-yl)bis(2-chloroethanone)

To a solution of trans-cyclobutane-1,2-dicarbonyl dichloride (0.27 g, 1.54 mmol) in CH₃CN (4 mL) cooled to 0° C. in an ice bath was added TMSCHN₂ (2.0 M solution in Et₂O, 1.54 mL, 3.08 mmol). The resulting reaction mixture was allowed to warm to 25° C. and stirred for 2 h at which time the mixture was cooled to 0° C. with an ice bath and then 4 M HCl in dioxane (1.0 mL, 4 mmol) was added and the reaction mixture was allowed to warm to 25° C. with stirring for 16 h. After the reaction was complete, the volatiles were removed in vacuo and the oil was partitioned in EtOAc and NaHCO₃ (sat. aq.), extracted with EtOAc (3×50 mL), the combined organic fractions were washed with brine and dried over Na₂SO₄ filtered and the solvent removed in vacuo. The crude trans-1,1'-(cyclobutane-1,2-di-yl)bis(2-chloroethanone) was observed by GC-MS as m/z 156 (presumed fragmentation during chromatography) and was used without further purification.

c. 1,2-Bis(8-chloroimidazo[1,2-a]pyridin-2-yl)cyclobutane and 2-Chloro-1-(2-(8-chloroimidazo[1,2-a]pyridin-2-yl)cyclopropyl)ethanone To a solution of trans-1,1'-(cyclobutane-1,2-di-yl)bis(2-chloroethanone) (62 mg, 0.3 mmol) in EtOH (3 mL) added to a microwave reaction vial was added 3-chloropyridin-2-amine (84.5 mg, 0.66 mmol) and the reaction vial was sealed with an aluminum crimped cap. The reaction mixture was heated to 90° C. under microwave irradiation for 2 h at which time the crude reaction mixture was purified directly by RP-HPLC (10-50% gradient 0.1% formic acid/H₂O in acetonitrile). Lyophilization of the collected fractions afforded the title compound as the formate salt and the mono-adduct 2-chloro-1-(2-(8-chloroimidazo[1,2-a]pyridin-2-yl)cyclopropyl)ethanone which was used in the subsequent reaction.

d. 8-Chloro-2-(2-(7-fluoroimidazo[1,2-a]pyridin-2-yl)cyclobutyl)imidazo[1,2-a]pyridine To a solution of 2-chloro-1-(2-(8-chloroimidazo[1,2-a]pyridin-2-yl)cyclopropyl)ethanone (15 mg, 0.05 mmol) in EtOH (2 mL) added to a microwave reaction vial was added 3-chloropyridin-2-amine (15 mg, 0.13 mmol) and the reaction vial was sealed with an aluminum crimped cap. The reaction mixture was heated to 90° C. under microwave irradiation for 2 h at which time the crude reaction mixture was purified directly by RP-HPLC (10-50% gradient 0.1% formic acid/H₂O in acetonitrile). Lyophilization of the collected fractions afforded the title compound as the formate salt.

9. General Procedure I

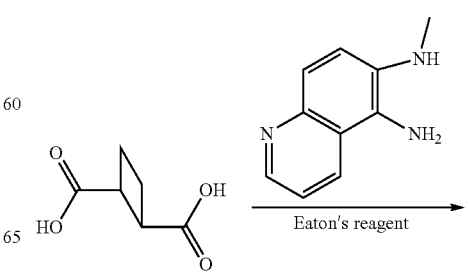

a. 1,2-Bis(3-methyl-3H-imidazo[4,5-f]quinolin-2-yl)cyclobutane

To a flask containing trans-cyclobutane-1,2-dicarboxylic acid (0.1 g, 0.7 mmol) and $N^6$-methylquinoline-5,6-diamine (WO2011150156A2, 0.132 g, 0.76 mmol) was added Eaton's reagent (9 mL) and the resulting reaction mixture was allowed to stir at 80° C. for 2 h. Disappearance of starting materials was observed by LC-MS and the reaction was quenched carefully with $K_2CO_3$ (sat. aq.) and partitioned between EtOAc and $H_2O$. The aqueous layers were extracted with EtOAc (3×50 mL) and the resulting organic layers were washed with brine, dried over $Na_2SO_4$, filtered and the solvent was removed in vacuo. The resulting crude oil was diluted in 3 ml MeOH and purified by RP-HPLC (10-50% gradient, 0.1% formic acid in $H_2O$ in $CH_3CN$) to afford the title compound as a white powder.

10. General Procedure J

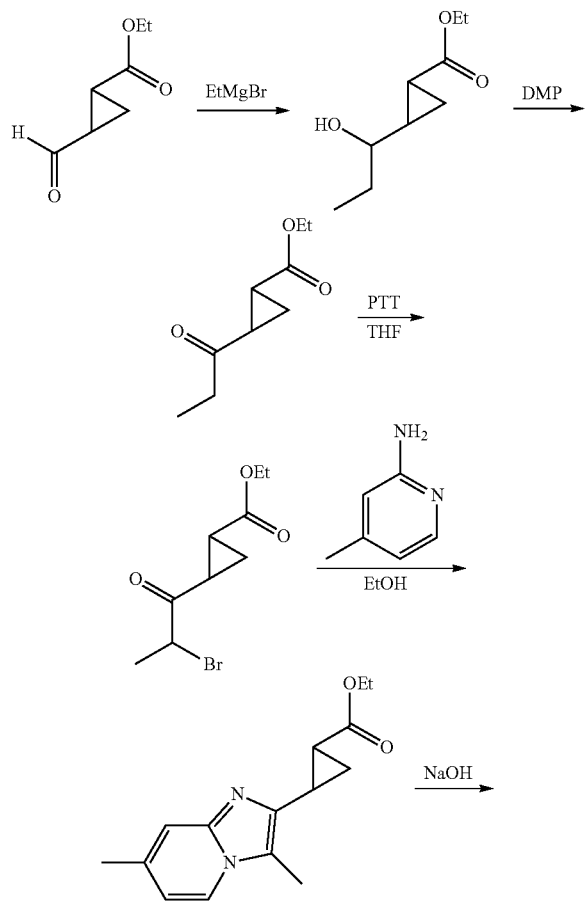

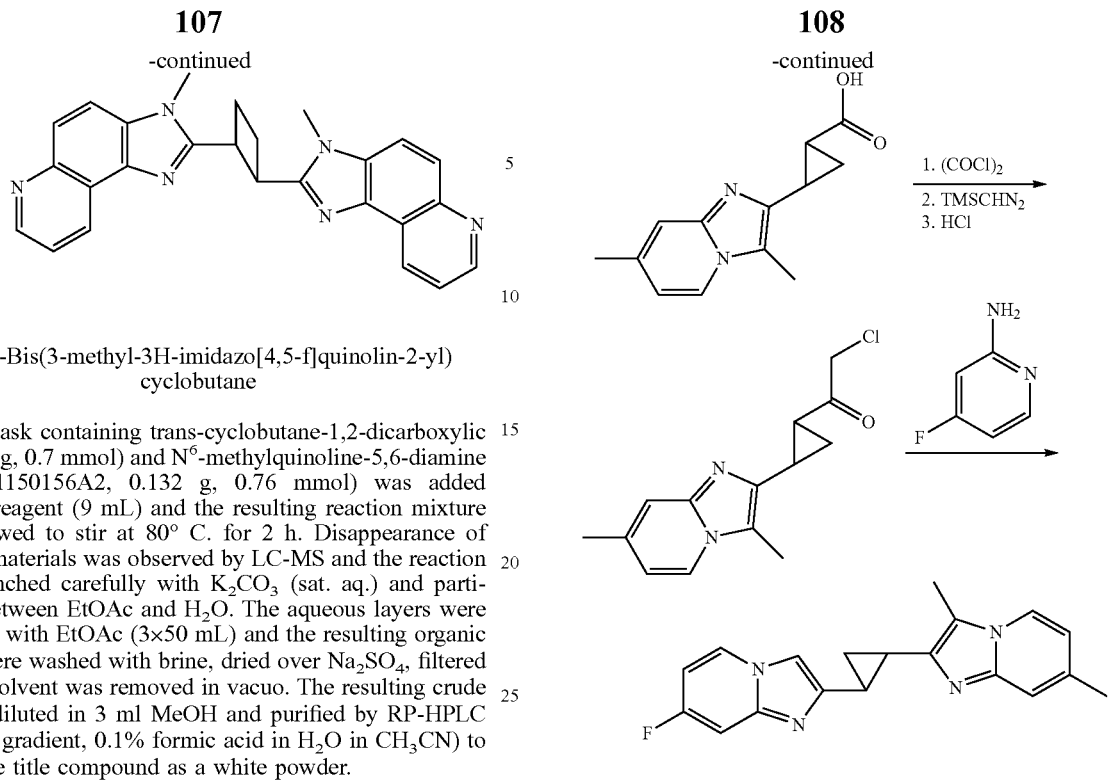

a. Ethyl 2-(1-hydroxypropyl)cyclopropanecarboxylate

A solution of ethyl 2-formylcyclopropanecarboxylate (Aldrich) (1 g, 7 mmol) in anhydrous THF (15 mL) was stirred at −78° C. under $N_2$. Then ethyl magnesium bromide (1.0 M in THF, 7 mL, 7 mmol) was added dropwise to the solution, and the mixture was stirred at −78° C. for 2 hours and allowed to warm to room temperature. Then TLC indicated that the reaction is completed, and the mixture was quenched with sat. ammonium chloride solution, separated, and the water was extracted with EtOAc (10 mL×3), the combined organic layers was dried with sodium sulfate, filter and the solvent was removed under reduced pressure and the residue was purified by silica gel chromatography using PE:EtOAc (V:V, 10:1) as the eluent. 1.0 g, colorless oil, yield: 83%. $^1$H NMR (400 MHz, $CDCl_3$) δ: 4.08-4.15 (m, 2H), 3.01-3.19 (m, 1H), 1.50-1.64 (m, 4H), 1.23-1.27 (m, 3H), 1.12-1.23 (m, 1H), 0.94-1.00 (m, 3H), 0.83-0.94 (m, 1H).

b. Ethyl 2-propionylcyclopropanecarboxylate

A solution of ethyl 2-(1-hydroxypropyl)cyclopropanecarboxylate (1 g, 5.81 mmol) in DCM (25 mL) was stirred at room temperature. Then Dess-Martin periodinane (5.2 g, 12.2 mmol) was added to the solution and the mixture was stirred at room temperature for 14 h. Then sodium hydroxide solution (2 N, 30 mL) was added to the mixture and the mixture was stirred at room temperature for 20 minutes, separate, the water layer was extracted with EtOAc (15 mL×3), the combined organic layers was dried with sodium sulfate, filter and the solvent was removed under reduced pressure and the residue was purified by silica gel chromatography using PE:EtOAc (V:V: 25:1) as the eluent. 0.80 g, colorless oil, yield: 80%. $^1$H NMR (400 MHz, $CDCl_3$) δ: 4.15 (q, J=7.2 Hz, 2H), 2.64 (q, J=7.2 Hz, 2H), 2.42-2.47 (m, 1H), 2.14-2.19 (m, 1H), 1.41 (t, J=7.2 Hz, 3H), 1.27 (t, J=7.2 Hz, 3H), 1.09 (t, J=7.2 Hz, 3H).

c. Ethyl 2-(2-bromopropanoyl)cyclopropanecarboxylate

A solution of ethyl 2-propionylcyclopropanecarboxylate (0.85 g, 5 mmol) in anhydrous THF (30 mL) was stirred at room temperature. Then trimethyl phenyl ammonium tribromide (1.68 g, 5 mmol) was added to the solution and the mixture was stirred at room temperature for 3 h. Then LCMS indicated that the reaction is completed. Then the mixture was diluted with EtOAc (30 mL), washed by sat. sodium bicarbonate (5 mL×5), the organic layer was dried with sodium sulfate, filtered and the solvent was removed under reduced pressure and the residue, 1.50 g, yellow oil, was used in next step without further purification. MS (ESI): m/z 249, 251 [M+H]$^+$.

d. Ethyl 2-(3,7-dimethylimidazo[1,2-a]pyridin-2-yl)cyclopropanecarboxylate

A solution of ethyl 2-(2-bromopropanoyl)cyclopropanecarboxylate (1.50 g, the above crude product) in EtOH (20 mL) was stirred room temperature, then 4-methylpyridin-2-amine (0.65 g, 6 mmol) was added to the solution and the mixture was refluxed for 14 hours. Then LCMS indicated that the reaction is completed, cooling the mixture to room temperature and EtOH was removed under reduce pressure and the residue was dissolved with EtOAc (40 mL), washed by sat. sodium bicarbonate (10 mL×4), the organic layer was dried with sodium sulfate, filtered and the solvent was removed under reduced pressure and the residue was purified by Prep-TLC using PE:EtOAc (V:V, 1:1) as the eluent. 0.39 g, white solid, yield: 30%. MS (ESI): m/z 259 [M+H]$^+$.

e. 2-(3,7-Dimethylimidazo[1,2-a]pyridin-2-yl)cyclopropanecarboxylic acid

A solution of ethyl 2-(3,7-dimethylimidazo[1,2-a]pyridin-2-yl)cyclopropane carboxylate (1-5) (0.39 g, 1.51 mmol) in THF (20 mL) was stirred at room temperature. Then sodium hydroxide solution (2 N in water, 3 mL, 6 mmol) was added dropwise to the solution and the mixture was refluxed for 14 hours. Then LCMS indicated that the reaction is completed, cooling the mixture to room temperature and THF was removed under reduce pressure, the solution was acidified with hydrochloric acid (2 N) to adjust the pH to 5-6, then the mixture was purified with reverse-phase column chromatography using CH$_3$CN as the eluent, and the acetonitrile was removed under reduced pressure to obtain the 2-(3,7-dimethylimidazo[1,2-a]pyridin-2-yl)cyclopropanecarboxylic acid as a white solid. 310 mg, yield: 90%. MS (ESI): m/z 231 [M+H]$^+$. $^1$H NMR (400 MHz, CDCl$_3$) δ: 8.57 (d, J=6.8 Hz, 1H), 7.64 (s, 1H), 7.35 (m, 1H), 3.49 (br, 1H), 2.61-2.66 (m, 1H), 2.54 (s, 3H), 2.52 (s, 3H), 2.11-2.15 (m, 1H), 1.54-1.58 (m, 2H).

f. 2-Chloro-1-(2-(3,7-dimethylimidazo[1,2-a]pyridin-2-yl)cyclopropyl)ethanone To a solution of 2-(3,7-dimethylimidazo[1,2-a]pyridin-2-yl)cyclopropanecarboxylic acid (0.09 g, 0.4 mmol)) in CH$_2$Cl$_2$ (2.5 mL) was added oxalyl chloride (1.7 mL, 3.39 mmol) followed by DMF (0.05 mL) and the resulting reaction mixture was stirred at 25° C. for 2 h at which time the volatiles were removed in vacuo and the resulting oil was taken up in CH$_3$CN (3 mL) cooled to 0° C. in an ice bath and TMSCHN$_2$ (2.0 M solution in Et$_2$O, 0.45 mL, 0.9 mmol) was added. The resulting reaction mixture was allowed to warm to 25° C. and stirred for 2 h at which time the mixture was cooled to 0° C. with an ice bath and then 4 M HCl in dioxane (0.4 mL, 0.8 mmol) was added and the reaction mixture was allowed to warm to 25° C. with stirring for 16 h. After the reaction was complete, the volatiles were removed in vacuo and the oil was partitioned in EtOAc and NaHCO$_3$ (sat. aq.), extracted with EtOAc (3×50 mL), the combined organic fractions were washed with brine and dried over Na$_2$SO$_4$ filtered and the solvent removed in vacuo. The resulting yellow oil was used in the next step without further purification.

g. 2-(2-(7-Fluoroimidazo[1,2-a]pyridin-2-yl)cyclopropyl)-3,7-dimethylimidazo[1,2-a]pyridine To a solution of 2-chloro-1-(2-(3,7-dimethylimidazo[1,2-a]pyridin-2-yl)cyclopropyl)ethanone (105 mg, 0.4 mmol) in EtOH (4 mL) added to a microwave reaction vial was added 4-fluoropyridin-2-amine (45 mg, 0.4 mmol) and the reaction vial was sealed with an aluminum crimped cap. The reaction mixture was heated to 90° C. under microwave irradiation for 2 h at which time the crude reaction mixture was purified directly by RP-HPLC (10-50% gradient 0.1% formic acid/H$_2$O in CH$_3$CN). Lyophilization of the collected fractions afforded the title compound as the formate salt.

11. General Procedure K

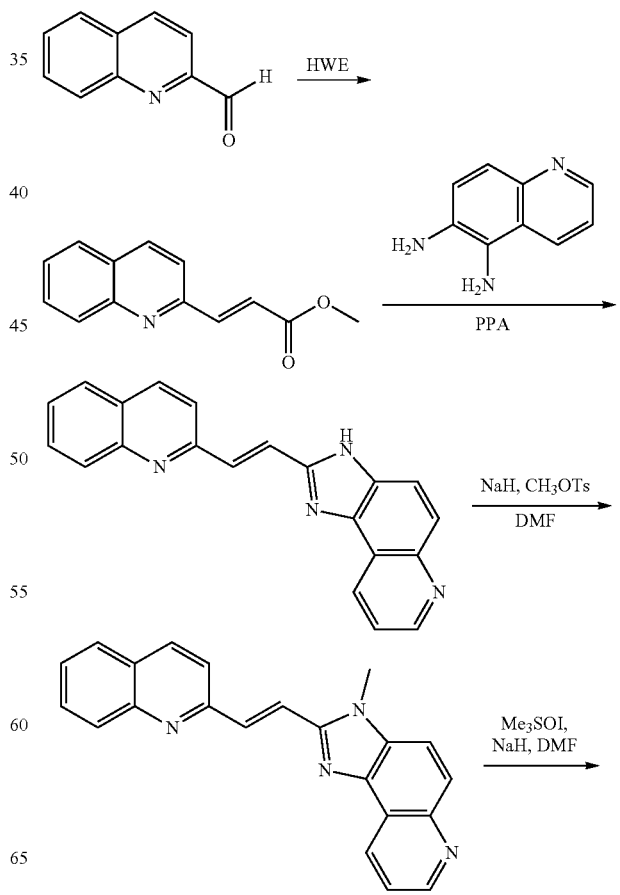

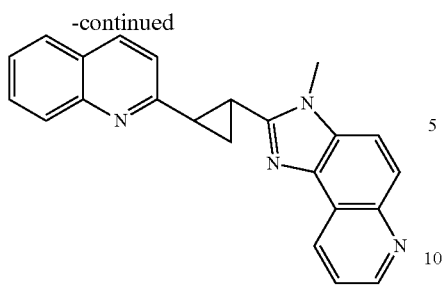

a. (E)-Methyl 3-(quinolin-2-yl)acrylate

To a dry 100 mL flask was added sodium hydride (60%, 360 mg) under $N_2$. The sodium hydride was washed with heptanes (10 mL×2), and then dry THF (25 mL) was added. To the mixture at 0° C. was added a solution of methyl 2-(diethoxyphosphoryl) acetate (2.08 g) in THF (2.0 mL) slowly. The mixture was stirred at 0° C. for 30 min. A solution of quinoline-2-carbaldehyde (470 mg) in THF (3.0 mL) was added to the mixture at 0° C. The mixture was stirred at room temperature for 30 min, and then poured into brine (50 mL). The mixture was extracted with EtOAc (30 mL×2). The combined organic phase was dried, concentrated and purified by flash column (PE:EtOAc=4:1) to give (E)-methyl 3-(quinolin-2-yl)acrylate (588 mg, 88%) as a pale purple solid. MS (ESI): m/z 214.1 [M+H]$^+$.

b. (E)-2-(2-(Quinolin-2-yl)vinyl)-3H-imidazo[4,5-f]quinoline

The mixture of (E)-methyl 3-(quinolin-2-yl)acrylate (197 mg), quinoline-5,6-diamine (WO2011150156A2, 197 mg) in polyphosphoric acid (5 mL) was heated to 170° C. for 1 h under $N_2$. Then the reaction was quenched by sat. potassium hydroxide (10 mL) at 90° C. dropwise. The solution was poured into aq. potassium hydroxide (30 mL) and extracted with EtOAc (30 mL×2). The combined organic phase was dried, concentrated and purified by flash column (DCM:MeOH=50:1) to give (E)-2-(2-(quinolin-2-yl)vinyl)-3H-imidazo[4,5-f]quinoline (270 mg, 91%) as a red solid. MS (ESI): m/z 323.1 [M+H]$^+$.

c. (E)-3-Methyl-2-(2-(quinolin-2-yl)vinyl)-3H-imidazo[4,5-f]quinoline

To the mixture of (E)-2-(2-(quinolin-2-yl)vinyl)-3H-imidazo[4,5-f]quinoline (50 mg) in DMF (2 mL) was added sodium hydride (60%, 80 mg). The mixture was stirred at room temperature for 30 min, and then methyl p-toluenesulfonate (400 mg) was added at 0° C. After stirring at 0° C. for 30 min, the reaction was quenched by aq. potassium hydroxide (1 mL). The mixture was diluted with aq. potassium hydroxide (30 mL) and extracted with DCM (30 mL×3). The combined organic phase was dried, concentrated and purified by flash column (EtOAc:MeOH=20:1) to give (E)-3-methyl-2-(2-(quinolin-2-yl)vinyl)-3H-imidazo[4,5-f]quinoline (40 mg, 74%) as a yellow solid. MS (ESI): m/z 337.0 [M+H]$^+$.

d. 3-Methyl-2-(2-(quinolin-2-yl)cyclopropyl)-3H-imidazo[4,5-f]quinoline

To the mixture of trimethylsulfoxonium iodide (580 mg) in DMF (2.0 mL) was added sodium hydride (60%, 144 mg). The mixture was stirred at room temperature for 30 min and then (E)-3-methyl-2-(2-(quinolin-2-yl)vinyl)-3H-imidazo[4,5-f]quinoline (35 mg) was added. The mixture was stirred at 50° C. for 2 h, then poured into ice-cooled aq. potassium hydroxide (30 mL), and extracted with EtOAc (30 mL×2). The combined organic phase was dried, concentrated and purified by flash column (PE:EtOAc=2:3) to give the title compound (15 mg, 35%) as a yellow solid.

12. General Procedure CS

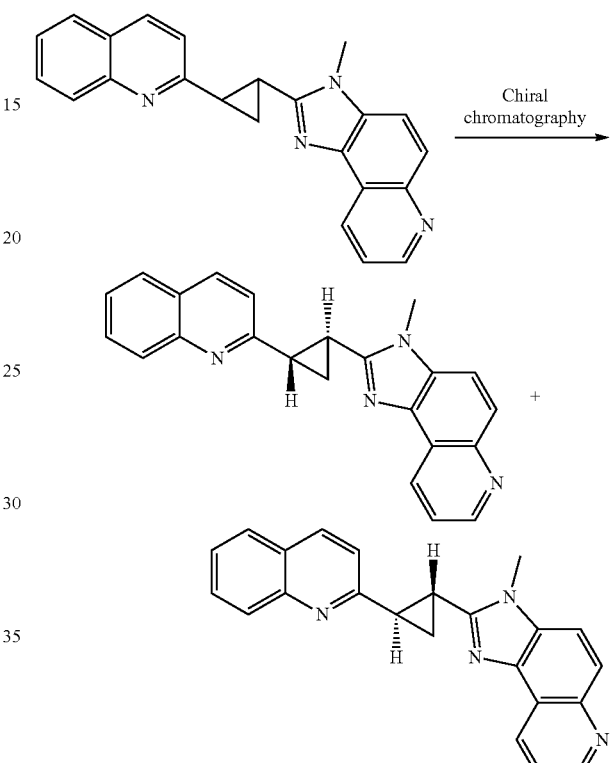

a. 3-Methyl-2-((1S,2S)-2-(quinolin-2-yl)cyclopropyl)-3H-imidazo[4,5-f]quinoline and 3-Methyl-2-((1R,2R)-2-(quinolin-2-yl)cyclopropyl)-3H-imidazo[4,5-f]quinoline Normal phase chiral separation of the racemic compounds disclosed herein was carried out using Chiral Technologies AS, AD, OJ and OD columns and the specified solvent system.

The following abbreviations were used:
IHD 5=5% isopropanol/95% hexanes/0.1% diethylamine
IHD 10=10% isopropanol/90% hexanes/0.1% diethylamine
MEHD 5=2.5% methanol/2.5% ethanol/95% hexanes/0.1% diethylamine
MEHD 2.5=1.25% methanol/1.25% ethanol/97.5% hexanes/0.1% diethylamine
The Faster Moving Enantiomer (FME) was the earlier eluting enantiomer and the Slower Moving Enantiomer was the later eluting enantiomer.
SFC (supercritical $CO_2$ fluid chromatography) chiral separation was done using an isocratic method using the specified column and co-solvent and $CO_2$ total flows between 60 to 80 g/minute.

B. Compounds

The following compounds were prepared using the above procedures.

| Cmpd. No. | Structure | Method of Prep. | Analytical Data |
|---|---|---|---|
| 1 | 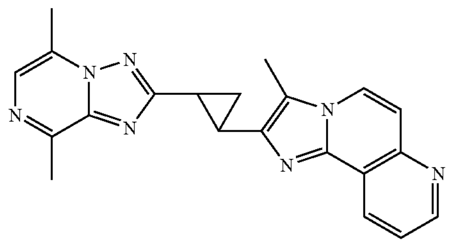 [SMILES: Cc1ncc(C)n2nc(C3CC3c3nc4c5cccnc5ccn4c3C)nc12] | C | MS (ESI): m/z 370 [M + 1]⁺. $^1$H NMR (400 MHz, CDCl$_3$) δ 8.85-8.89 (m, 2H), 7.79 (d, J = 7.6 Hz, 1H), 7.82 (s, 1H), 7.51 (q, J = 4.8, 8.4 Hz, 1H), 7.32 (d, J = 7.6 Hz, 1H), 2.99-3.03 (m, 1H), 2.88 (s, 3H), 2.73-2.78 (m, 1H), 2.72 (s, 3H), 2.55 (s, 3H), 1.91-1.98 (m, 2H). |
| 2 | 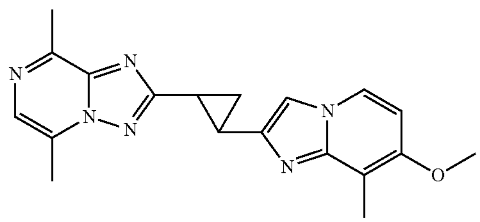 [SMILES: COc1ccn2cc(C3CC3c3nc4c(C)ncc(C)n4n3)nc2c1C] | E | MS (ESI): m/z 349 [M + 1]⁺. $^1$H NMR (400 MHz, CD$_3$OD) δ 8.12 (d, J = 7.6 Hz, 1H), 7.83 (s, 1H), 7.51 (s, 1H), 6.80 (d, J = 0.8 Hz, 1H), 3.90 (s, 3H), 2.87 (s, 3H), 2.70-2.76 (m, 1H), 2.68 (s, 3H), 2.32 (s, 3H), 1.73-1.84 (m, 2H). |
| 3 | 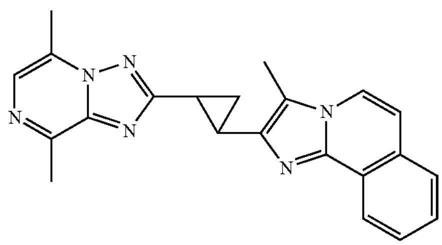 [SMILES: Cc1ncc(C)n2nc(C3CC3c3nc4c5ccccc5ccn4c3C)nc12] | A | MS (ESI): m/z 369 [M + 1]⁺. $^1$H NMR (400 MHz, CDCl$_3$) δ 8.60 (d, J = 8.0 Hz, 1H), 7.80 (d, J = 0.8 Hz, 1H), 7.65-7.70 (m, 2H), 7.58-7.62 (m, 1H), 7.50-7.54 (m, 1H), 7.04 (d, J = 7.2 Hz, 1H), 2.99-3.03 (m, 1H), 2.88 (s, 3H), 2.74-2.79 (m, 1H), 2.71 (s, 3H), 2.52 (s, 3H), 1.97-2.02 (m, 1H), 1.89-1.94 (m, 1H). |
| 4 | 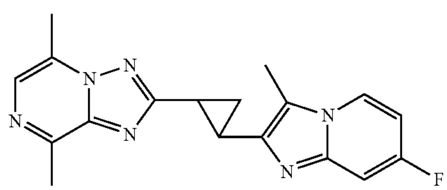 [SMILES: Cc1ncc(C)n2nc(C3CC3c3nc4cc(F)ccn4c3C)nc12] | A | MS (ESI): m/z 337 [M + 1]⁺. $^1$H NMR (400 MHz, CDCl$_3$) δ 7.81 (s, 1H), 7.75 (t, J = 5.6 Hz, 1H), 7.19 (d, J = 7.2 Hz, 1H), 6.69-6.73 (m, 1H), 2.92-2.96 (m, 1H), 2.87 (s, 3H), 2.71 (s, 3H), 2.66-2.69 (m, 1H), 2.48 (s, 3H), 1.90-1.98 (m, 2H). |
| 5 | 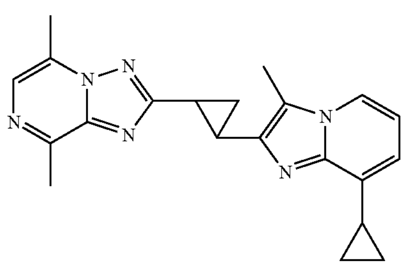 [SMILES: Cc1ncc(C)n2nc(C3CC3c3nc4c(C5CC5)cccn4c3C)nc12] | B | MS (ESI): m/z 359 [M + 1]⁺. $^1$H NMR (400 MHz, CDCl$_3$) δ 7.80 (s, 1H), 7.60 (d, J = 6.8 Hz, 1H), 6.69 (t, J = 6.4 Hz, 1H), 6.58 (d, J = 6.8 Hz, 1H), 2.97-3.01 (m, 1H), 2.88 (s, 3H), 2.73-2.78 (m, 1H), 2.71 (s, 3H), 2.56-2.60 (m, 1H), 2.47 (s, 3H), 1.94-1.98 (m, 1H), 1.86-1.91 (m, 1H), 1.07-1.11 (m, 2H), 0.96-1.0 (m, 2H). |
| 6 | 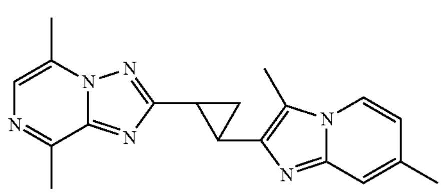 [SMILES: Cc1ccn2c(C)c(C3CC3c3nc4c(C)ncc(C)n4n3)nc2c1] | A | MS (ESI): m/z 333 [M + 1]⁺. $^1$H NMR (400 MHz, CDCl$_3$) δ 7.78 (s, 1H), 7.65 (d, J = 6.8 Hz, 1H), 7.27 (s, 1H), 6.60 (d, J = 5.6 Hz, 1H), 2.89-2.94 (m, 1H), 2.85 (s, 3H), 2.66-2.71 (m, 4H), 2.43 (s, 3H), 2.37 (s, 3H), 1.86-1.96 (m, 2H). |
| 7 | 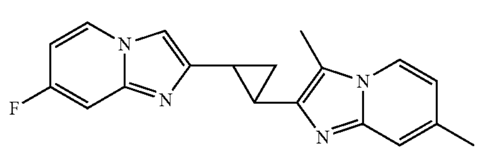 [SMILES: Cc1ccn2c(C)c(C3CC3c3cn4ccc(F)cc4n3)nc2c1] | J | $^1$H NMR (400 MHz, CD$_3$OD) δ 8.36 (dd, J = 6.5, 6.0 Hz, 1H), 7.99 (d, J = 7.0 Hz, 1H), 7.69 (s, 1H), 7.22 (s, 1H), 7.11 (dd, J = 9.5, 2.5 Hz, 1H), 6.84-6.79 (m, 2H), 2.55-2.42 (m, 2H), 2.47 (s, 3H), 2.41 (s, 3H), 1.66-1.58 (m, 2H). |

-continued

| Cmpd. No. | Structure | Method of Prep. | Analytical Data |
|---|---|---|---|
| 8 | 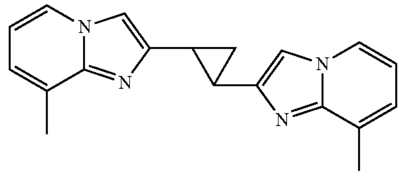 [SMILES: Cc1cccn2cc(C3CC3c3cn4cccc(C)c4n3)nc12] | G | MS (ESI+): m/z 303 (MH+); 1H NMR (300 MHz, CDCl3): δ 7.90-7.87 (d, J = 6.6 Hz, 2H), 7.36 (s, 2H), 6.90-6.87 (d, J = 6.9 Hz, 2H), 6.63-6.58 (t, J = 6.9 Hz, 2H), 2.64-2.58 (m, 8H), 1.65-1.62 (m, 2H). |
| 9 | 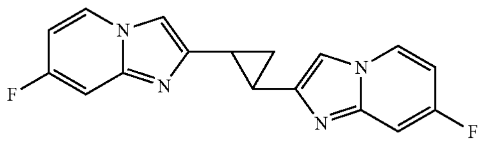 [SMILES: Fc1ccn2cc(C3CC3c3cn4ccc(F)cc4n3)nc2c1] | G | MS (ESI+): m/z 311 (MH+); 1H NMR (300 MHz, CDCl3): δ 7.98-7.96 (t, J = 6.9 Hz, 2H), 7.44 (s, 2H). 7.19-7.15 (dd, J = 9.6, 2.4 Hz, 2H), 6.66-6.60 (td, J = 7.2, 2.4 Hz, 2H), 2.65-2.59 (m, 2H), 1.75-1.65 (m, 2H). |
| 10 | 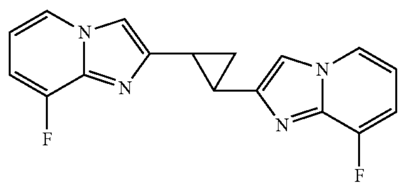 [SMILES: Fc1cccn2cc(C3CC3c3cn4cccc(F)c4n3)nc12] | G | MS (ESI+): m/z 311 (MH+); 1H NMR (300 MHz, CDCl3): δ 7.88-7.85 (d, J = 6.3 Hz, 2H), 7.55-7.54 (d, J = 3.0 Hz, 2H), 6.87-6.81 (m, 2H), 6.69-6.62 (m, 2H), 2.77-2.72 (m, 2H), 1.82-1.77 (m, 2H). |
| 11 | 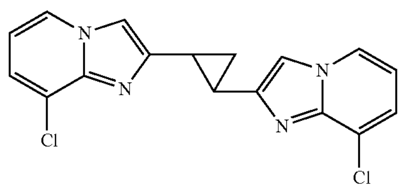 [SMILES: Clc1cccn2cc(C3CC3c3cn4cccc(Cl)c4n3)nc12] | G | MS (ESI+): m/z 343, 345 (MH+); 1H NMR (300 MHz, CDCl3): δ 7.99-7.97 (d, J = 6.0 Hz, 2H), 7.50 (s, 2H), 7.22-7.18 (dd, J = 7.5, 1.2 Hz, 2H), 6.70-6.65 (t, J = 6.9 Hz, 2H), 2.75-2.72 (m, 2H), 1.78-1.73 (m, 2H). |
| 12 | 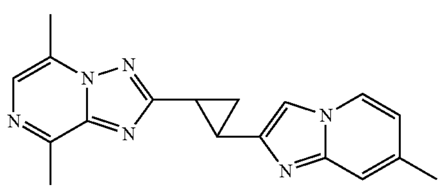 [SMILES: Cc1ccn2cc(C3CC3c3nc4c(C)ncc(C)n4n3)nc2c1] | D | 1H NMR (400 MHz, CD3OD) δ 8.27 (d, J = 6.5 Hz, 1H), 7.88 (s, 1H), 7.71 (s, 1H), 7.29 (s, 1H), 6.84 (d, J = 6.5 Hz, 1H), 2.80 (s, 3H), 2.79-2.70 (m, 2H), 2.71 (s, 3H), 2.43 (s, 3H), 1.88-1.81 (m, 1H), 1.79-1.76 (m, 1H). |
| 13 | 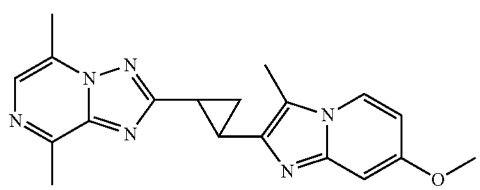 [SMILES: COc1ccn2c(C)c(C3CC3c3nc4c(C)ncc(C)n4n3)nc2c1] | A | MS (ESI): m/z 349 [M + 1]+. 1H NMR (400 MHz, CDCl3) δ 7.79 (s, 1H), 7.61 (d, J = 7.2 Hz, 1H), 6.83 (d, J = 2.4 Hz, 1H), 6.51 (d, J = 5.2 Hz, 1H), 3.84 (s, 3H), 2.89-2.93 (m, 1H), 2.86 (s, 3H), 2.69 (s, 3H), 2.63-2.68 (m, 1H), 2.42 (s, 3H), 1.88-1.95 (m, 2H). |
| 14 | 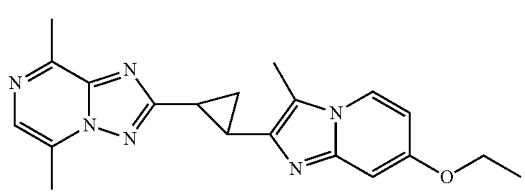 [SMILES: CCOc1ccn2c(C)c(C3CC3c3nc4c(C)ncc(C)n4n3)nc2c1] | A | MS (ESI): m/z 363.2 [M + 1]+. 1H NMR (400 MHz, CDCl3) δ 7.78 (d, J = 0.5 Hz, 1H), 7.60 (d, J = 7.0 Hz, 1H), 6.81 (d, J = 6.81 Hz, 1H), 6.50 (dd, J = 7.0, 2.5 Hz, 1H), 4.05 (q, J = 7.0 Hz, 2H), 2.94-2.88 (m, 1H), 2.86 (s, 3H), 2.69 (s, 3H), 2.69-2.63 (m, 1H), 2.42 (s, 3H), 1.96-1.86 (m, 2H), 1.45 (t, J = 7.0 Hz, 3H). |
| 15 | 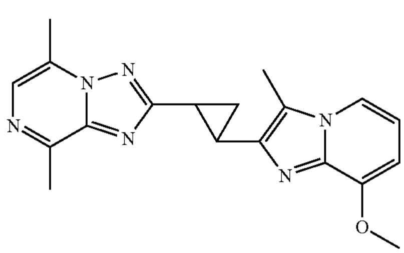 [SMILES: COc1cccn2c(C)c(C3CC3c3nc4c(C)ncc(C)n4n3)nc12] | A | MS (ESI): m/z 349.2 [M + 1]+. 1H NMR (400 MHz, CDCl3) δ 7.78 (s, 1H), 7.45 (dd, J = 7.0, 2.0 Hz, 1H), 6.70 (dd, J = 7.0, 3.0 Hz, 1H), 6.43 (dd, J = 7.0, 1.0 Hz, 1H), 4.01 (s, 3H), 3.02-2.97 (m, 1H), 2.86 (s, 3H), 2.73 (s, 3H), 2.72-2.68 (m, 1H), 2.46 (s, 3H), 2.10-2.04 (m, 1H), 1.91-1.85 (m, 1H). |

| Cmpd. No. | Structure | Method of Prep. | Analytical Data |
|---|---|---|---|
| 16 | 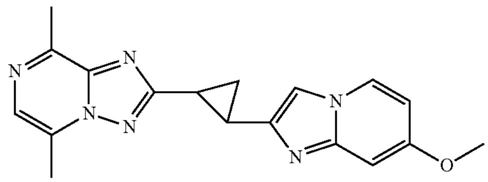 [SMILES: COc1ccn2cc(C3CC3c3nc4c(C)ncc(C)n4n3)nc2c1] | D | $^1$H NMR (400 MHz, CD$_3$OD) δ 8.27 (brs, 1H), 8.24 (d, J = 7.5 Hz, 1H), 7.88 (s, 1H), 7.63 (s, 1H), 6.88 (d, J = 2.0 Hz, 1H), 6.73 (dd, J = 7.5, 2.0 Hz, 1H), 3.91 (s, 3H), 2.80 (s, 3H), 2.80-2.70 (m, 2H), 2.70 (s, 3H), 1.89-1.84 (m, 1H), 1.79-1.74 (m, 1H). |
| 17 | 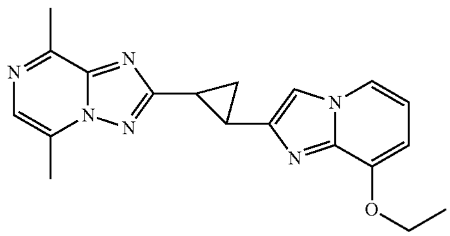 [SMILES: CCOc1cccn2cc(C3CC3c3nc4c(C)ncc(C)n4n3)nc12] | D | $^1$H NMR (400 MHz, CD$_3$OD) δ 8.18 (brs, 1H), 7.97 (d, J = 7.5 Hz, 1H), 7.88 (s, 1H), 7.75 (s, 1H), 6.85 (dd, J = 7.5, 7.0 Hz, 1H), 6.75 (d, J = 7.5 Hz, 1H), 4.25 (q, J = 7.0 Hz, 2H), 2.80 (s, 3H), 2.80-2.76 (m, 2H), 2.70 (s, 3H), 1.88-1.81 (m, 2H), 1.52 (t, J = 7.0 Hz, 3H). |
| 18 | 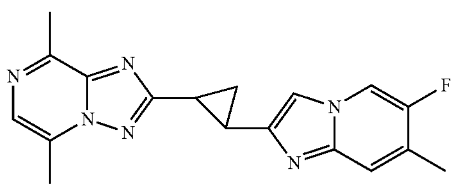 [SMILES: Cc1cc2nc(C3CC3c3nc4c(C)ncc(C)n4n3)cn2cc1F] | D | $^1$H NMR (400 MHz, CD$_3$OD) δ 8.38 (d, J = 5.0 Hz, 1H), 8.17 (s, 1H), 7.88 (s, 1H), 7.70 (s, 1H), 7.31 (d, J = 7.0 Hz, 1H), 2.80 (s, 3H), 2.80-2.70 (m, 2H), 2.70 (s, 3H), 2.38 (s, 3H), 1.88-1.82 (m, 1H), 1.79-1.74 (m, 1H). |
| 19 | 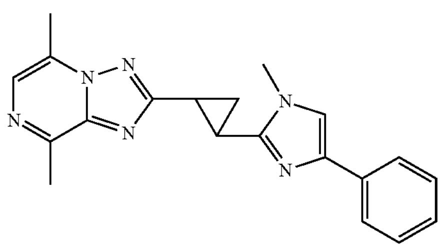 [SMILES: Cc1ncc(C)n2nc(C3CC3c3nc(-c4ccccc4)cn3C)nc12] | F | MS (ES+): m/z 345.32 [M + 1]$^+$. $^1$H NMR (400 MHz, CD$_3$OD) δ 8.20 (brs, 1H), 7.90 (s, 1H), 7.69 (dd, J = 8.0, 1.0 Hz, 2H), 7.41 (s, 1H), 7.36 (apt, J = 8.0 Hz, 2H), 7.24 (apt, J = 7.5 Hz, 1H), 3.77 (s, 3H), 2.89-2.81 (m, 1H), 2.82 (s, 3H), 2.81-2.71 (m, 1H), 2.73 (s, 3H), 1.98-1.87 (m, 2H). |
| 20 | 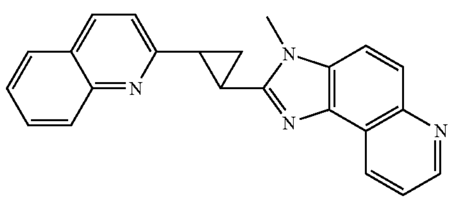 [SMILES: Cn1c(C2CC2c2ccc3ccccc3n2)nc2c3cccnc3ccc21] | K | MS (ESI): m/z 351.1 [M + 1]$^+$. $^1$H NMR (400 MHz, CDCl$_3$) δ 8.94 (d, J = 8.0 HZ, 1H), 8.90 (d, J = 2.5 Hz, 1H), 8.07 (d, J = 8.0 Hz, 1H), 8.01 (d, J = 8.0 Hz, 1H), 7.95 (d, J = 9.0 Hz, 1H), 7.79 (d, J = 8.5 Hz, 1H), 7.70-7.67 (m, 2H), 7.53-7.45 (m, 3H), 3.94 (s, 3H), 3.02-2.97 (m, 2H), 2.13-2.08 (m, 2H). |
| 21 | 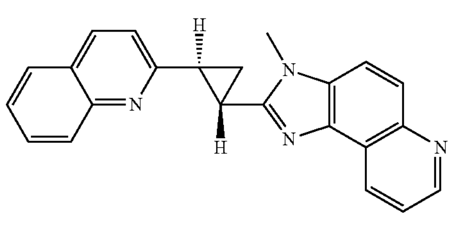 [SMILES: Cn1c([C@H]2C[C@@H]2c2ccc3ccccc3n2)nc2c3cccnc3ccc21] | CS (FME) LUX Cellulose 2 Hx: IPA (1:1) with 0.1% iso-propylamine | MS (ESI): m/z 351.1 [M + 1]$^+$. $^1$H NMR (400 MHz, CDCl$_3$) δ 8.94 (d, J = 8.0 HZ, 1H), 8.90 (d, J = 2.5 Hz, 1H), 8.07 (d, J = 8.0 Hz, 1H), 8.01 (d, J = 8.0 Hz, 1H), 7.95 (d, J = 9.0 Hz, 1H), 7.79 (d, J = 8.5 Hz, 1H), 7.70-7.67 (m, 2H), 7.53-7.45 (m, 3H), 3.94 (s, 3H), 3.02-2.97 (m, 2H), 2.13-2.08 (m, 2H). |
| 22 | 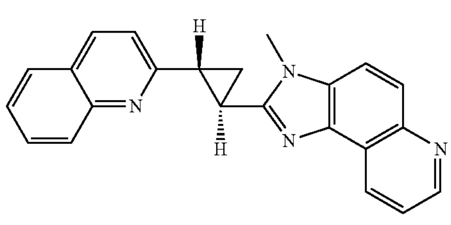 [SMILES: Cn1c([C@@H]2C[C@H]2c2ccc3ccccc3n2)nc2c3cccnc3ccc21] | CS (SME) LUX Cellulose 2 Hx: IPA (1:1) with 0.1% iso-propylamine | MS (ESI): m/z 351.1 [M + 1]$^+$. $^1$H NMR (400 MHz, CDCl$_3$) δ 8.94 (d, J = 8.0 HZ, 1H), 8.90 (d, J = 2.5 Hz, 1H), 8.07 (d, J = 8.0 Hz, 1H), 8.01 (d, J = 8.0 Hz, 1H), 7.95 (d, J = 9.0 Hz, 1H), 7.79 (d, J = 8.5 Hz, 1H), 7.70-7.67 (m, 2H), 7.53-7.45 (m, 3H), 3.94 (s, 3H), 3.02-2.97 (m, 2H), 2.13-2.08 (m, 2H). |

-continued

| Cmpd. No. | Structure | Method of Prep. | Analytical Data |
|---|---|---|---|
| 23 | 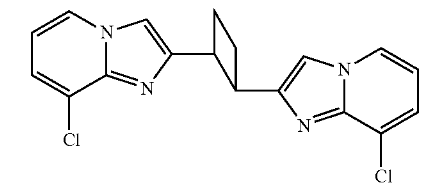 [SMILES: Clc1cccn2cc(C3CCC3c3cn4cccc(Cl)c4n3)nc12] | H | ¹H NMR (400 MHz, CD₃OD) δ 8.31 (dd, J = 6.5, 1.0 Hz, 1H), 8.15 (s, 1H), 7.84 (s, 1H), 7.35 (dd, J = 6.5, 1.0 Hz, 1H), 6.83 (t, J = 7.0 Hz, 1H), 3.94-3.90 (m, 1H), 2.44-2.39 (m, 2H). |
| 24 | 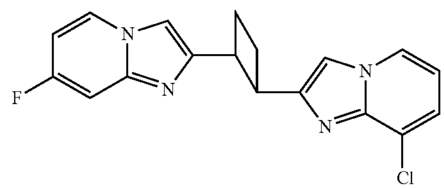 [SMILES: Fc1ccn2cc(C3CCC3c3cn4cccc(Cl)c4n3)nc2c1] | H | ¹H NMR (400 MHz, CD₃OD) δ 8.40 (dd, J = 7.0, 6.5 Hz, 1H), 8.31 (d, J = 7.0 Hz, 1H), 8.21 (brs, 1H), 7.81 (s, 1H), 7.70 (s, 1H), 7.36 (d. J = 6.5 Hz, 1H), 7.17 (d, J = 9.0, 2.0 Hz, 1H), 6.89-6.81 (m, 2H), 3.88-3.83 (m, 1H), 2.42-2.38 (m, 2H). |
| 25 | 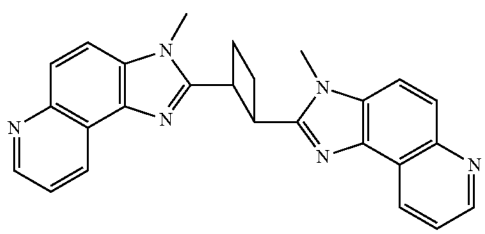 [SMILES: Cn1c(C2CCC2c2nc3c4cccnc4ccc3n2C)nc2c3cccnc3ccc21] | I | ¹H NMR (400 MHz, CD₃OD) δ 9.06 (d, J = 7.0 Hz, 2H), 8.81 (dd, J = 4.5 1.5 Hz, 2H), 8.80 (brs, 2H), 7.96 (d, J = 9.1 Hz, 2H), 7.90 (d, J = 9.1 Hz, 2H), 7.64 (dd, J = 8.5, 4.5 Hz, 2H), 4.79-4.74 (m, 2H), 3.99 (s, 6H), 2.72-2.59 (m, 4H). |
| 26 | 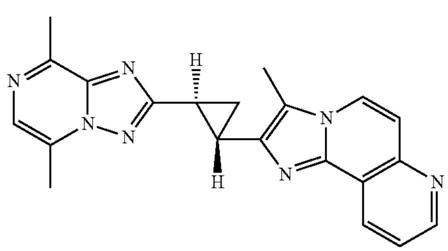 [SMILES: Cc1ncc(C)n2nc([C@H]3C[C@@H]3c3nc4c5cccnc5ccn4c3C)nc12] | CS (FME) ChiralPak OD-H CH₃CN: CH₃OH (3:1) with 0.1% iso-propylamine | MS (ESI): m/z 370 [M + 1]⁺. ¹H NMR (400 MHz, CDCl₃) δ 8.85-8.89 (m, 2H), 7.79 (d, J = 7.6 Hz, 1H), 7.82 (s, 1H), 7.51 (q, J = 4.8, 8.4 Hz, 1H), 7.32 (d, J = 7.6 Hz, 1H), 2.99-3.03 (m, 1H), 2.88 (s, 3H), 2.73-2.78 (m, 1H), 2.72 (s, 3H), 2.55 (s, 3H), 1.91-1.98 (m, 2H). |
| 27 | 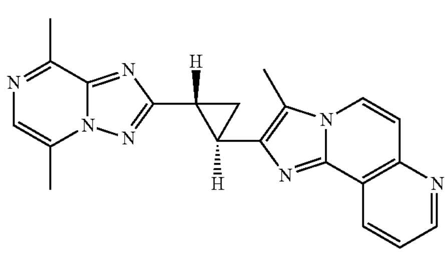 [SMILES: Cc1ncc(C)n2nc([C@@H]3C[C@H]3c3nc4c5cccnc5ccn4c3C)nc12] | CS (SME) ChiralPak OD-H CH₃CN: CH₃OH (3:1) with 0.1% iso-propylamine | MS (ESI): m/z 370 [M + 1]⁺. ¹H NMR (400 MHz, CDCl₃) δ 8.85-8.89 (m, 2H), 7.79 (d, J = 7.6 Hz, 1H), 7.82 (s, 1H), 7.51 (q, J = 4.8, 8.4 Hz, 1H), 7.32 (d, J = 7.6 Hz, 1H), 2.99-3.03 (m, 1H), 2.88 (s, 3H), 2.73-2.78 (m, 1H), 2.72 (s, 3H), 2.55 (s, 3H), 1.91-1.98 (m, 2H). |
| 28 | 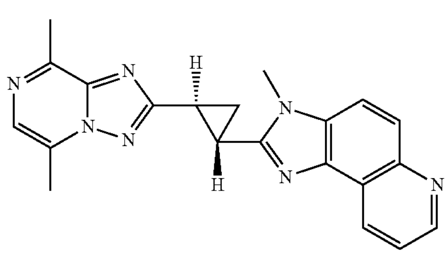 [SMILES: Cc1ncc(C)n2nc([C@H]3C[C@@H]3c3nc4c5cccnc5ccc4n3C)nc12] | CS (FME) Regis Cell, MeOH | MS (ESI): m/z 370 (M + 1)⁺. ¹HNMR (400 MHz, CDCl₃): δ 8.89-8.93 (m, 2H), 7.95 (d, 1H, J = 9.2 Hz), 7.84 (s, 1H), 7.68 (d, 1H, J = 9.2 Hz), 7.51 (dd, 1H, J = 4.4 Hz, 8.0 Hz), 3.95 (s, 3H), 3.07-3.11 (m, 1H), 2.87 (s, 3H), 2.85-2.89 (m, 1H), 2.72 (s, 3H), 2.17-2.22 (m, 1H), 2.02-2.07 (m, 1H). |

| Cmpd. No. | Structure | Method of Prep. | Analytical Data |
|---|---|---|---|
| 29 | 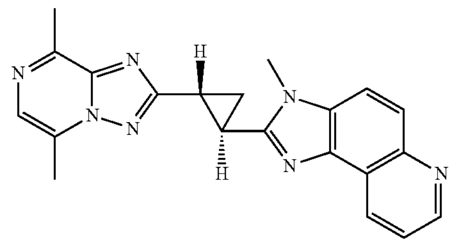 [SMILES: Cc1ncc(C)n2nc([C@@H]3C[C@H]3c3nc4c5cccnc5ccc4n3C)nc12] | CS (SME) Regis Cell, MeOH | MS (ESI): m/z 370 (M + 1)+. 1HNMR (400 MHz, CDCl3): δ 8.89-8.93 (m, 2H), 7.95 (d, 1H, J = 9.2 Hz), 7.84 (s, 1H), 7.68 (d, 1H, J = 9.2 Hz), 7.51 (dd, 1H, J = 4.4 Hz, 8.0 Hz), 3.95 (s, 3H), 3.07-3.11 (m, 1H), 2.87 (s, 3H), 2.85-2.89 (m, 1H), 2.72 (s, 3H), 2.17-2.22 (m, 1H), 2.02-2.07 (m, 1H). |

The following compounds were synthesized according to the methods described herein:

Compound 30: (±)-2-(2-(5,8-dimethyl-[1,2,4]triazolo[1,5-a]pyrazin-2-yl)cyclopropyl)-7-fluoro-3-methylimidazo[2,1-a]isoquinoline

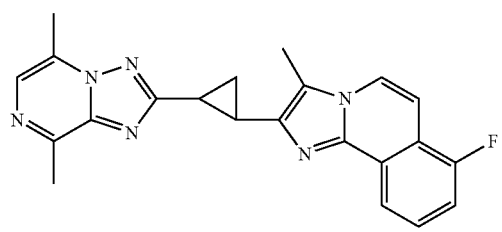 [SMILES: Cc1ncc(C)n2nc(C3CC3c3nc4c5cccc(F)c5ccn4c3C)nc12]

1H NMR (400 MHz, CDCl3): δ 8.36 (d, J=8.4 Hz, 1H), 7.80 (m, 1H), 7.70 (d, J=7.6 Hz, 1H), 7.52 (m, 1H), 7.29 (d, J=7.6 Hz, 1H), 7.21 (m, 1H), 3.00 (m, 1H), 2.87 (s, 3H), 2.75 (m, 1H), 2.70 (s, 3H), 2.53 (s, 3H), 1.99-1.89 (m, 2H), LC/MS: m/e=387 (M+H)+.

Compound 31: (±)-2-(2-(8-(difluoromethoxy)-3-methylimidazo[1,2-a]pyridin-2-yl)cyclopropyl)-5,8-dimethyl-[1,2,4]triazolo[1,5-a]pyrazine

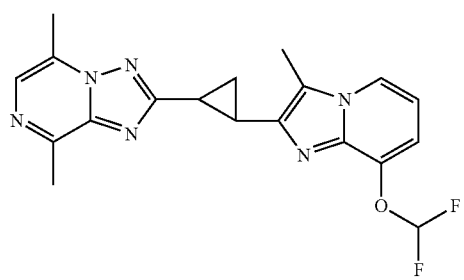 [SMILES: Cc1ncc(C)n2nc(C3CC3c3nc4c(OC(F)F)cccn4c3C)nc12]

1H NMR (400 MHz, CDCl3): δ 7.80 (d, J=0.8 Hz, 1H), 7.66 (dd, J1=6.8 Hz, J2=0.8 Hz, 1H), 7.63 (d, J=0.4 Hz, 1H), 6.90 (d, J=7.2 Hz, 1H), 6.74 (m, 1H), 2.99 (m, 1H), 2.87 (s, 3H), 2.73 (m, 1H), 2.70 (s, 3H), 2.49 (s, 3H), 1.96-1.86 (m, 2H), LC/MS: m/e=385 (M+H)+.

Compound 32: (±)-2-(2-(8-ethoxy-3-methylimidazo[1,2-a]pyridin-2-yl)cyclopropyl)-5,8-dimethyl-[1,2,4]triazolo[1,5-a]pyrazine

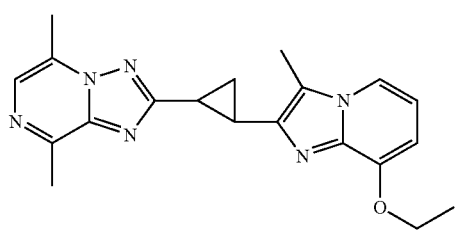 [SMILES: CCOc1cccn2c(C)c(C3CC3c3nc4c(C)ncc(C)n4n3)nc12]

1H NMR (400 MHz, CDCl3): δ 7.78 (m, 1H), 7.43 (m, 1H), 6.68 (m, 1H), 6.43 (d, J=7.6 Hz, 1H), 4.28 (q, J=7.2 Hz, 2H), 2.97 (m, 1H), 2.86 (s, 3H), 2.74 (m, 1H), 2.69 (s, 3H), 2.45 (s, 3H), 2.03 (m, 1H), 1.84 (m, 1H), 1.56 (t, J=7.2 Hz, 3H), LC/MS: m/e=363 (M+H)+.

Compound 33: (±)-2-(2-(6-fluoro-3,7-dimethylimidazo[1,2-a]pyridin-2-yl)cyclopropyl)-5,8-dimethyl-[1,2,4]triazolo[1,5-a]pyrazine

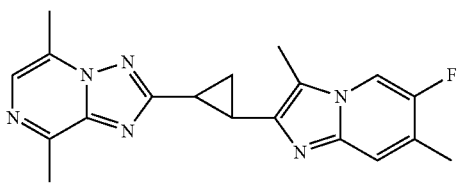 [SMILES: Cc1cc2nc(C3CC3c3nc4c(C)ncc(C)n4n3)c(C)n2cc1F]

1H NMR (400 MHz, CDCl3): δ 7.79 (m, 1H), 7.65 (d, J=4.8 Hz, 1H), 7.30 (d, J=7.2 Hz, 1H), 2.91 (m, 1H), 2.86 (s, 3H), 2.69 (s, 3H), 2.68 (m, 1H), 2.43 (s, 3H), 2.35 (m, 3H), 1.95-1.87 (m, 2H), LC/MS: m/e=351 (M+H)+.

Compound 34: (±)-2-(2-(6-fluoro-8-methoxy-3-methylimidazo[1,2-a]pyridin-2-yl)cyclopropyl)-5,8-dimethyl-[1,2,4]triazolo[1,5-a]pyrazine

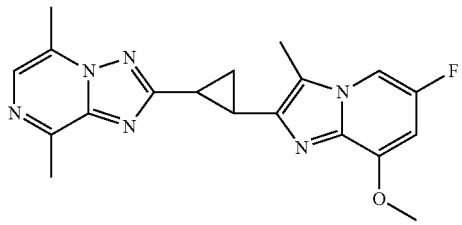 [SMILES: COc1cc(F)cn2c(C)c(C3CC3c3nc4c(C)ncc(C)n4n3)nc12]

$^1$H NMR (400 MHz, CDCl$_3$): δ 7.79 (m, 1H), 7.40 (dd, J$_1$=4.0 Hz, J$_2$=2.0 Hz, 1H), 6.40 (dd, J$_1$=10.4 Hz, J$_2$=2.0 Hz, 1H), 4.02 (s, 3H), 2.96 (m, 1H), 2.86 (s, 3H), 2.69 (s, 3H), 2.68 (m, 1H), 2.43 (s, 3H), 2.05 (m, 1H), 1.90 (m, 1H), LC/MS: m/e=351 (M+H)$^+$.

Compound 35: (±)-9-(2-(5,8-dimethyl-[1,2,4]triazolo[1,5-a]pyrazin-2-yl)cyclopropyl)-8-methyl-2,3-dihydro-[1,4]dioxino[2,3-c]imidazo[1,2-a]pyridine

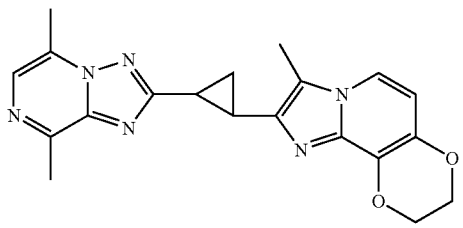 [SMILES: Cc1ncc(C)n2nc(C3CC3c3nc4c5c(ccn4c3C)OCCO5)nc12]

$^1$H NMR (400 MHz, CDCl$_3$): δ 7.78 (m, 1H), 7.31 (d, J=7.2 Hz, 1H), 6.49 (d, J=7.2 Hz, 1H), 4.45 (m, 2H), 4.35 (m, 2H), 2.99 (m, 1H), 2.86 (s, 3H), 2.68 (s, 3H), 2.65 (m, 1H), 2.41 (s, 3H), 2.04 (m, 1H), 1.86 (m, 1H), LC/MS: m/e=377 (M+H)$^+$.

Compound 36: (±)-2-(2-(8-methoxy-3,6-dimethylimidazo[1,2-a]pyridin-2-yl)cyclopropyl)-5,8-dimethyl-[1,2,4]triazolo[1,5-a]pyrazine

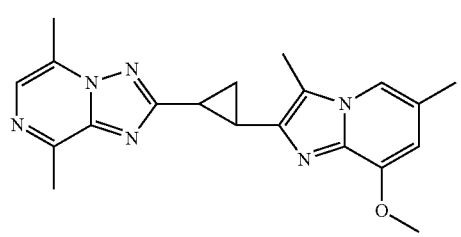 [SMILES: COc1cc(C)cn2c(C)c(C3CC3c3nc4c(C)ncc(C)n4n3)nc12]

$^1$H NMR (400 MHz, CDCl$_3$): δ 7.77 (m, 1H), 7.23 (m, 1H), 6.28 (m, 1H), 3.99 (s, 3H), 2.97 (m, 1H), 2.85 (s, 3H), 2.68 (s, 3H), 2.67 (m, 1H), 2.42 (s, 3H), 2.32 (s, 3H), 2.05 (m, 1H), 1.85 (m, 1H), LC/MS: m/e=363 (M+H)$^+$.

Compound 37: (±)-2-(2-(6,8-dimethoxy-3-methylimidazo[1,2-a]pyridin-2-yl)cyclopropyl)-5,8-dimethyl-[1,2,4]triazolo[1,5-a]pyrazine

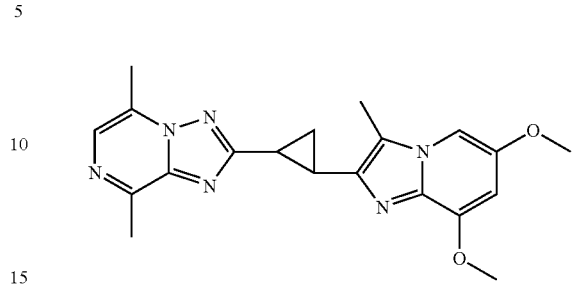

$^1$H NMR (400 MHz, CDCl$_3$): δ 7.77 (m, 1H), 6.96 (d, J=1.6 Hz, 1H), 6.26 (d, J=1.6 Hz, 1H), 3.98 (s, 3H), 3.83 (s, 3H), 2.95 (m, 1H), 2.85 (s, 3H), 2.68 (s, 3H), 2.67 (m, 1H), 2.43 (s, 3H), 2.03 (m, 1H), 1.85 (m, 1H), LC/MS: m/e=379 (M+H)$^+$.

Compound 38: (±)-9-(2-(5,8-dimethyl-[1,2,4]triazolo[1,5-a]pyrazin-2-yl)cyclobutyl)-2,3-dihydro-[1,4]dioxino[2,3-c]imidazo[1,2-a]pyridine

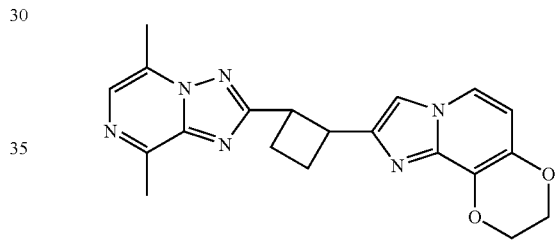

$^1$H NMR (400 MHz, d$^4$-MeOH): δ 7.88 (m, 1H), 7.82 (d, J=7.6 Hz, 1H), 7.52 (s, 1H), 6.53 (d, J=7.6 Hz, 1H), 4.41 (m, 2H), 4.36 (m, 2H), 4.08 (m, 2H), 2.83 (s, 3H), 2.71 (s, 3H), 2.56 (m, 1H), 2.46 (m, 3H), LC/MS: m/e=377 (M+H)$^+$.

Compound 39: (±)-9-(2-(5,8-dimethyl-[1,2,4]triazolo[1,5-a]pyrazin-2-yl)cyclopropyl)-2,3-dihydro-[1,4]dioxino[2,3-c]imidazo[1,2-a]pyridine

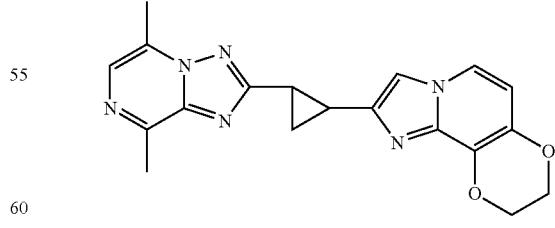

$^1$H NMR (400 MHz, CDCl$_3$): δ 7.78 (s, 1H), 7.55 (d, J=6.8 Hz, 1H), 7.33 (s, 1H), 6.45 (d, J=7.2 Hz, 1H), 4.45 (m, 2H), 4.36 (m, 2H), 2.92 (m, 1H), 2.85 (s, 3H), 2.74 (m, 1H), 2.69 (s, 3H), 1.94 (m, 1H), 1.83 (m, 1H), LC/MS: m/e=363 (M+H)$^+$.

Compound 40: (±)-2-(2-(5,8-dimethyl-[1,2,4]tri-azolo[1,5-a]pyrazin-2-yl)cyclobutyl)-3-methyl-3H-imidazo[4,5-f]quinoline (cis-isomer)

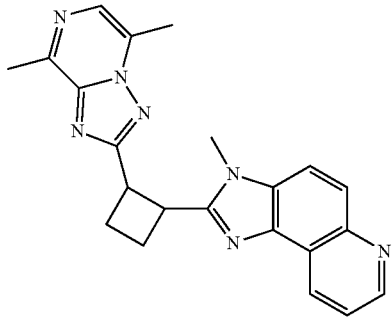 [SMILES: Cc1ncc(C)n2nc(C3CCC3c3nc4c5cccnc5ccc4n3C)nc12]

$^1$H NMR (400 MHz, d$^4$-MeOH): δ 9.03 (d, J=8.0 Hz, 1H), 8.77 (d, J=4.4 Hz, 1H), 7.82 (m, 3H), 7.59 (m, 1H), 4.52 (m, 1H), 4.41 (m, 1H), 3.84 (s, 3H), 2.83 (m, 1H), 2.81 (s, 3H), 2.68 (s, 3H), 2.60 (m, 3H), LC/MS: m/e=384 (M+H)$^+$.

Compound 41: (±)-2-(3-(5,8-dimethyl-[1,2,4]tri-azolo[1,5-a]pyrazin-2-yl)cyclobutyl)-3-methylimi-dazo[2,1-f][1,6]naphthyridine

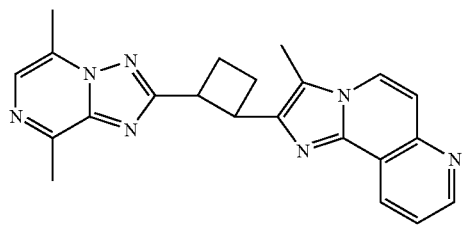 [SMILES: Cc1ncc(C)n2nc(C3CCC3c3nc4c5cccnc5ccn4c3C)nc12]

$^1$H NMR (400 MHz, d$^4$-MeOH): δ 9.05 (dd, J$_1$=8.0 Hz, J$_2$=0.4 Hz, 1H), 8.84 (dd, J$_1$=4.4 Hz, J$_2$=1.2 Hz, 1H), 8.23 (d, J=7.6 Hz, 1H), 7.88 (m, 1H), 7.69 (dd, J$_1$=8.4 Hz, J$_2$=4.4 Hz, 1H), 7.31 (d, J=7.6 Hz, 1H), 4.30 (m, 2H), 2.82 (s, 3H), 2.78 (m, 1H), 2.71 (s, 3H), 2.58 (m, 2H), 2.46 (s, 3H), 2.43 (m, 1H), LC/MS: m/e=384 (M+H)$^+$.

Compound 42: (±)-2-(2-(8-methoxy-3-methylimi-dazo[1,2-a]pyridin-2-yl)cyclobutyl)-5,8-dimethyl-[1,2,4]triazolo[1,5-a]pyrazine

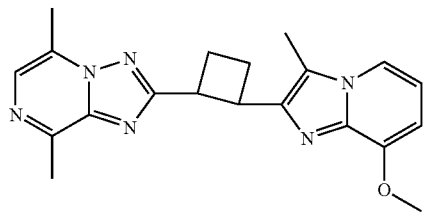 [SMILES: COc1cccn2c(C)c(C3CCC3c3nc4c(C)ncc(C)n4n3)nc12]

$^1$H NMR (400 MHz, d$^4$-MeOH): δ 7.81 (m, 1H), 7.60 (m, 1H), 6.76 (m, 1H), 6.59 (d, J=7.6 Hz, 1H), 4.20 (m, 2H), 3.98 (s, 3H), 2.78 (s, 3H), 2.69 (m, 1H), 2.66 (s, 3H), 2.50 (m, 2H), 2.31 (m, 1H), 2.30 (s, 3H), LC/MS: m/e=363 (M+H)$^+$.

Compound 43: (±)-2-(2-(7-methoxy-3-methylimi-dazo[1,2-a]pyridin-2-yl)cyclobutyl)-5,8-dimethyl-[1,2,4]triazolo[1,5-a]pyrazine

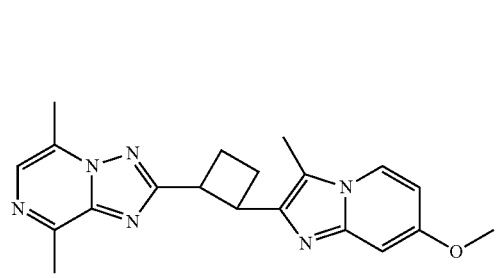 [SMILES: COc1ccn2c(C)c(C3CCC3c3nc4c(C)ncc(C)n4n3)nc2c1]

$^1$H NMR (400 MHz, d$^4$-MeOH): δ 7.85 (m, 1H), 7.84 (s, 1H), 6.81 (d, J=2.4 Hz, 1H), 6.56 (dd, J$_1$=7.6 Hz, J$_2$=2.4 Hz, 1H), 4.16 (m, 2H), 3.86 (s, 3H), 2.80 (s, 3H), 2.68 (s, 3H), 2.67 (m, 1H), 2.50 (m, 2H), 2.35 (m, 1H), 2.29 (s, 3H), LC/MS: m/e=363 (M+H)$^+$.

Compound 44: (±)-2-(2-(3-fluoro-8-methoxy-6-methylimidazo[1,2-a]pyridin-2-yl)cyclopropyl)-5,8-dimethyl-[1,2,4]triazolo[1,5-a]pyrazine

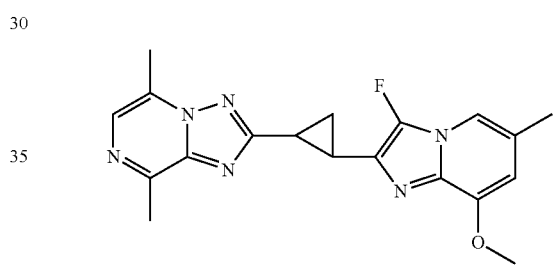

$^1$H NMR (400 MHz, CDCl$_3$): δ 7.71 (s, 1H), 7.20 (s, 1H), 6.16 (s, 1H), 3.91 (s, 3H), 2.86 (m, 1H), 2.77 (s, 3H), 2.70 (m, 1H), 2.61 (s, 3H), 2.23 (s, 3H), 1.91 (m, 1H), 1.80 (m, 1H), LC/MS: m/e=367 (M+H)$^+$.

Compound 45: (±)-2-(2-(5,8-dimethylimidazo[1,2-a]pyrazin-2-yl)cyclopropyl)-5,8-dimethyl-[1,2,4]tri-azolo[1,5-a]pyrazine

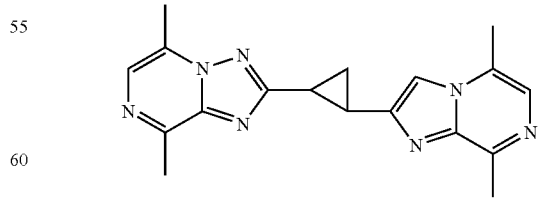

$^1$H NMR (400 MHz, CDCl$_3$): δ 7.81 (s, 1H), 7.56 (s, 1H), 7.40 (s, 1H), 2.90 (m, 2H), 2.86 (s, 3H), 2.83 (s, 3H), 2.70 (s, 3H), 2.50 (s, 3H), 1.94-1.87 (m, 2H), LC/MS: m/e=334 (M+H)$^+$.

Compound 46: (±)-2-(2-(4-methoxy-1-methyl-1H-benzo[d]imidazol-2-yl)cyclopropyl)-5,8-dimethyl-[1,2,4]triazolo[1,5-a]pyrazine

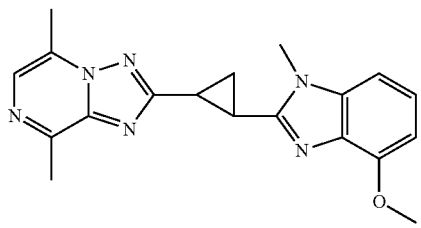 [SMILES: COc1cccc2c1nc(C1CC1c1nc3c(C)ncc(C)n3n1)n2C]

¹H NMR (400 MHz, CDCl₃): δ 7.82 (s, 1H), 7.18 (t, J=8.0 Hz, 2H), 6.91 (d, J=8.0 Hz, 1H), 6.68 (d, J=8.0 Hz, 1H), 4.03 (s, 3H), 3.81 (s, 3H), 3.05 (m, 1H), 2.87 (s, 3H), 2.78 (m, 1H), 2.70 (s, 3H), 2.24 (m, 1H), 1.95 (m, 1H), LC/MS: m/e=349 (M+H)⁺.

Compound 47: (±)-2-(2-(4-methoxy-1H-benzo[d]imidazol-2-yl)cyclopropyl)-5,8-dimethyl-[1,2,4]triazolo[1,5-a]pyrazine

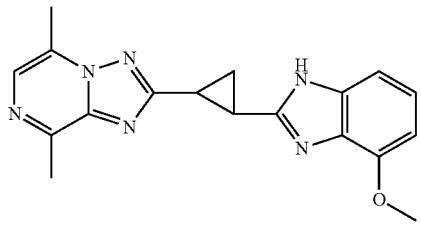 [SMILES: COc1cccc2[nH]c(C3CC3c3nc4c(C)ncc(C)n4n3)nc12]

¹H NMR (400 MHz, CDCl₃): δ 7.81 (s, 1H), 7.13 (t, J=8.0 Hz, 2H), 6.67 (d, J=8.8 Hz, 1H), 3.98 (s, 3H), 3.04 (m, 1H), 2.84 (s, 3H), 2.80 (m, 1H), 2.69 (s, 3H), 2.15 (bs, 1H), 1.94 (m, 1H), LC/MS: m/e=335 (M+H)⁺.

Compound 48: (±)-9-(2-(5,8-dimethyl-[1,2,4]triazolo[1,5-a]pyrazin-2-yl)cyclopropyl)-8-fluoro-2,3-dihydro-[1,4]dioxino[2,3-c]imidazo[1,2-a]pyridine

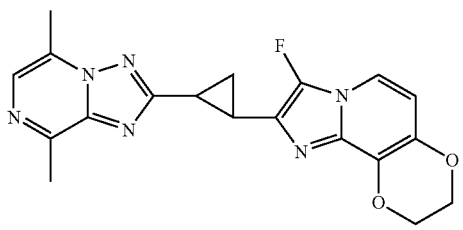

¹H NMR (400 MHz, CDCl₃): δ 7.79 (s, 1H), 7.37 (d, J=7.2 Hz, 1H), 6.54 (d, J=7.2 Hz, 1H), 4.45 (m, 2H), 4.36 (m, 2H), 2.94 (m, 1H), 2.86 (s, 3H), 2.75 (m, 1H), 2.69 (s, 3H), 1.98 (m, 1H), 1.86 (m, 1H), LC/MS: m/e=381 (M+H)⁺.

Compound 49: 2-(2-(6-fluoro-8-methoxy-3-methyl-imidazo[1,2-a]pyridin-2-yl)cyclopropyl)-5,8-dimethyl-[1,2,4]triazolo[1,5-a]pyrazine

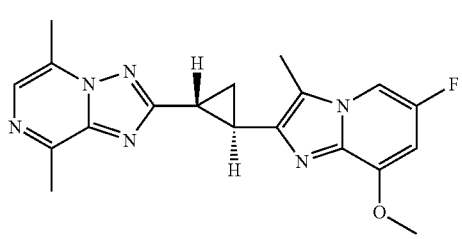 [SMILES: COc1cc(F)cn2c(C)c([C@@H]3C[C@H]3c3nc4c(C)ncc(C)n4n3)nc12]

Chiral Peak 1 of Compound 34. LC/MS: m/e=351 (M+H)⁺. Absolute stereochemistry unknown.

Compound 50: 2-(2-(6-fluoro-8-methoxy-3-methyl-imidazo[1,2-a]pyridin-2-yl)cyclopropyl)-5,8-dimethyl-[1,2,4]triazolo[1,5-a]pyrazine

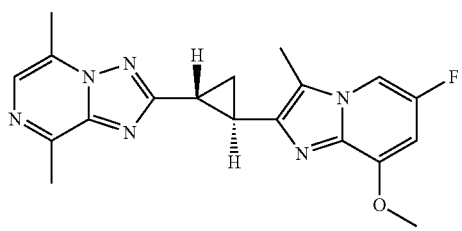 [SMILES: COc1cc(F)cn2c(C)c([C@@H]3C[C@H]3c3nc4c(C)ncc(C)n4n3)nc12]

Chiral Peak 2 of Compound 34 LC/MS: m/e=351 (M+H)⁺. Absolute stereochemistry unknown.

Compound 51: 5,8-dimethyl-2-(2-(1-methyl-4-phenyl-1H-imidazol-2-yl)cyclopropyl)-[1,2,4]triazolo[1,5-a]pyrazine

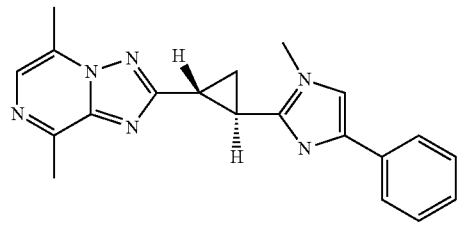

Chiral Peak 1 of Compound 19. LC/MS: m/e=351 (M+H)⁺. Absolute stereochemistry unknown.

Compound 52: 5,8-dimethyl-2-(2-(1-methyl-4-phenyl-1H-imidazol-2-yl)cyclopropyl)-[1,2,4]triazolo[1,5-a]pyrazine

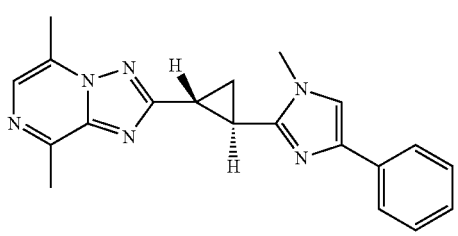 [SMILES: Cc1ncc(C)n2nc([C@@H]3C[C@H]3c3nc(-c4ccccc4)cn3C)nc12]

Chiral Peak 2 of Compound 19. LC/MS: m/e=351 (M+H)⁺. Absolute stereochemistry unknown.

Compound 53: 2-(2-(8-methoxy-3,6-dimethylimidazo[1,2-a]pyridin-2-yl)cyclopropyl)-5,8-dimethyl-[1,2,4]triazolo[1,5-a]pyrazine

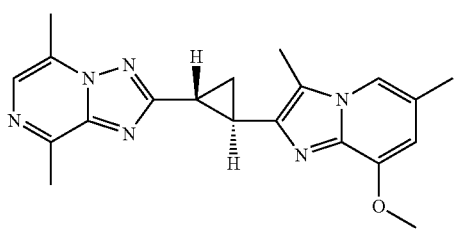 [SMILES: COc1cc(C)cn2c(C)c([C@@H]3C[C@H]3c3nc4c(C)ncc(C)n4n3)nc12]

Chiral Peak 1 of Compound 36. LC/MS: m/e=351 (M+H)⁺. Absolute stereochemistry unknown.

Compound 54: 2-(2-(8-methoxy-3,6-dimethylimidazo[1,2-a]pyridin-2-yl)cyclopropyl)-5,8-dimethyl-[1,2,4]triazolo[1,5-a]pyrazine

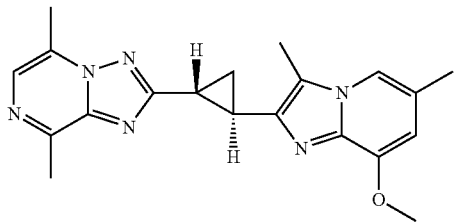 [SMILES: COc1cc(C)cn2c(C)c([C@@H]3C[C@H]3c3nc4c(C)ncc(C)n4n3)nc12]

Chiral Peak 2 of Compound 36. LC/MS: m/e=351 (M+H)⁺. Absolute stereochemistry unknown.

Compound 55: (±)-2-(2-(3-fluoro-8-methoxyimidazo[1,2-a]pyridin-2-yl)cyclopropyl)-5,8-dimethyl-[1,2,4]triazolo[1,5-a]pyrazine

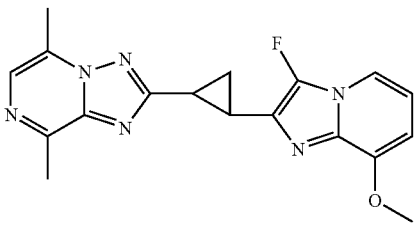 [SMILES: COc1cccn2c(F)c(C3CC3c3nc4c(C)ncc(C)n4n3)nc12]

Racemate. LC/MS: m/e=353 (M+H)⁺.

Compound 56: 2-(2-(3-fluoro-8-methoxyimidazo[1,2-a]pyridin-2-yl)cyclopropyl)-5,8-dimethyl-[1,2,4]triazolo[1,5-a]pyrazine

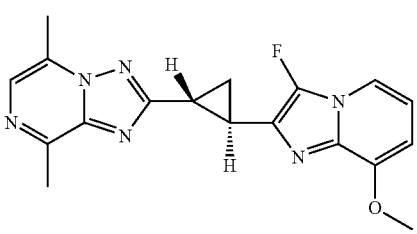 [SMILES: COc1cccn2c(F)c([C@@H]3C[C@H]3c3nc4c(C)ncc(C)n4n3)nc12]

Chiral Peak 1 of Compound 55. Absolute stereochemistry unknown. LC/MS: m/e=353 (M+H)⁺.

Compound 57: 2-(2-(3-fluoro-8-methoxyimidazo[1,2-a]pyridin-2-yl)cyclopropyl)-5,8-dimethyl-[1,2,4]triazolo[1,5-a]pyrazine

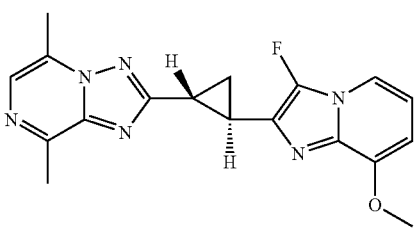 [SMILES: COc1cccn2c(F)c([C@@H]3C[C@H]3c3nc4c(C)ncc(C)n4n3)nc12]

Chiral Peak 2 of Compound 55. Absolute stereochemistry unknown. LC/MS: m/e=353 (M+H)⁺.

Compound 58: (±)-8-chloro-2-(2-(7-fluoroimidazo[1,2-a]pyridin-2-yl)cyclobutyl)imidazo[1,2-a]pyridine

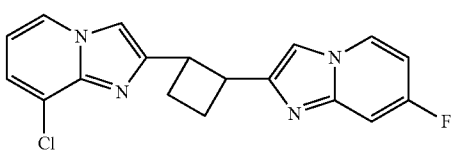 [SMILES: Fc1ccn2cc(C3CCC3c3cn4cccc(Cl)c4n3)nc2c1]

LC/MS: m/e=341 (M+H)⁺.

Compound 59: (±)-2-(2-(8-methoxyimidazo[1,2-a]pyridin-2-yl)cyclopropyl)-5,8-dimethyl-[1,2,4]triazolo[1,5-a]pyrazine

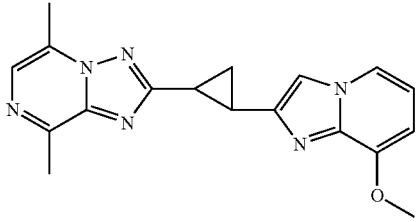 [SMILES: COc1cccn2cc(C3CC3c3nc4c(C)ncc(C)n4n3)nc12]

LC/MS: m/e=336 (M+H)⁺.

C. In Vitro Pharmacology

In one embodiment, the compounds provided herein were assayed for their ability to inhibit human PDE-10A. In one embodiment, the activities of the compounds were determined using the Molecular Devices IMAP PDE Fluorescence Polarization assay using recombinant human PDE-10 enzyme expressed in a baculoviral system. Briefly, 10 μL, of a compound (0.2 nM-20 μM) was added to either a 96-well half area black plate or a 384-well black plate along with 10 μL of Fluorescein-labeled cAMP/cGMP substrate as per manufacturer's instructions and 10 μL of PDE enzyme (activity 0.1 U). Following a 40-minute incubation at 37° C., 60 μL of IMAP binding reagent was added. The plate was then read on a Perkin Elmer Victor (480-535 nm). The data was analyzed using Prism Software (GraphPad Inc, San Diego, Calif.).

The potency of the compounds provided herein in human PDE-10 inhibition assay (enzyme assay $IC_{50}$) is summarized in the table below.

$IC_{50} \leq 0.01$ μM ++++;
$0.01 < IC_{50} \leq 0.1$ μM +++;
$0.1 < IC_{50} \leq 0.5$ μM ++;
$IC_{50} > 0.5$ μM +.

| Compound No. | PDE-10 $IC_{50}$ (μM) |
|---|---|
| 1 | ++++ |
| 2 | + |
| 3 | ++++ |
| 4 | + |
| 5 | +++ |
| 6 | ++ |
| 7 | + |
| 8 | + |
| 9 | + |
| 10 | + |
| 11 | + |
| 12 | + |
| 13 | ++ |
| 14 | + |
| 15 | +++ |
| 16 | + |
| 17 | +++ |
| 18 | + |
| 19 | +++ |
| 20 | ++ |
| 21 | +++ |
| 22 | ++ |
| 23 | ++ |
| 24 | + |
| 25 | + |
| 26 | ++ |
| 27 | ++++ |
| 28 | ++ |
| 29 | ++++ |
| 30 | +++ |
| 31 | ++ |
| 32 | +++ |
| 33 | ++ |
| 34 | +++ |
| 35 | +++ |
| 36 | +++ |
| 37 | +++ |
| 38 | ++ |
| 39 | +++ |
| 40 | + |
| 41 | ++ |
| 42 | + |
| 43 | + |
| 44 | +++ |
| 45 | + |
| 46 | ++ |
| 47 | ++ |
| 48 | +++ |
| 49 | ++ |
| 50 | ++++ |
| 51 | ++ |
| 52 | +++ |
| 53 | ++ |
| 54 | +++ |
| 55 | +++ |
| 56 | + |
| 57 | +++ |
| 58 | + |
| 59 | ++ |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is better understood with reference to the appended claims.

At Column 139, Lines 60-65, the chemical structure 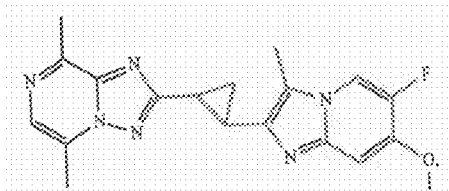 should be replaced with 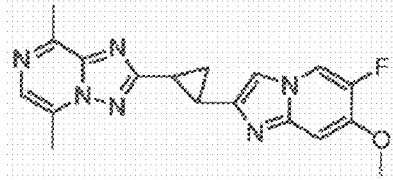

What is claimed:
1. A compound of formula (I):

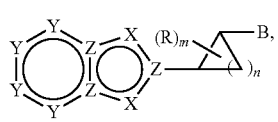

or a pharmaceutically acceptable salt or stereoisomer thereof, wherein

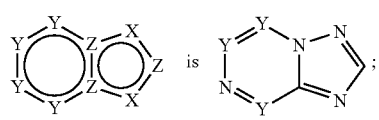

n is 1, 2, or 3;

m is 0, 1, 2, 3, 4, 5, 6, 7, or 8; provided that (i) when n is 1, m is 0, 1, 2, 3, or 4; (ii) when n is 2, m is 0, 1, 2, 3, 4, 5, or 6; and (iii) when n is 3, m is 0, 1, 2, 3, 4, 5, 6, 7, or 8;

each R is independently halo or ($C_1$-$C_4$) alkyl;

each Y is $CR^3$;

each $R^3$ is independently hydrogen, halo, cyano, alkyl, alkenyl, alkoxy, aminoalkyl, heteroalkyl, cycloalkyl, aryl, heteroaryl, heterocyclyl, amino, amido or thiol;

B is

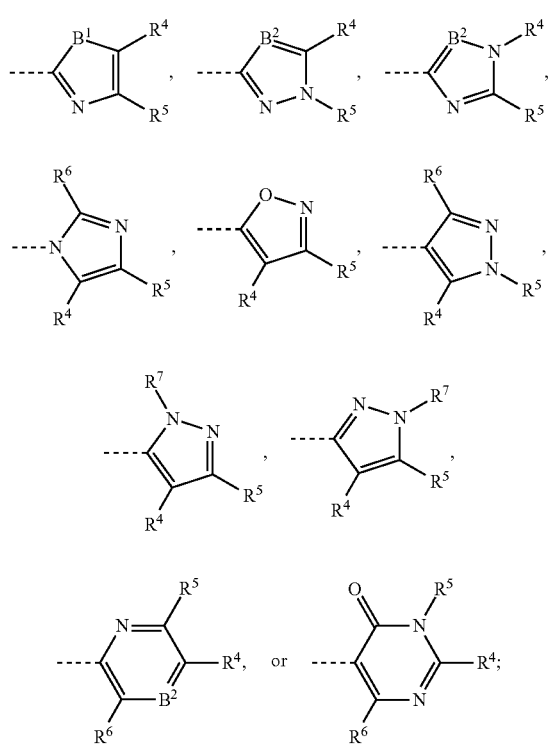

(i) $R^4$ and $R^5$ together with the atoms to which they are attached form a monocyclic or multicyclic aryl, heteroaryl, cycloalkyl, or heterocyclyl ring; or (ii) $R^4$ and $R^5$ are each independently hydrogen, cyano, halo, alkyl, alkenyl, alkoxy, aminoalkyl, heteroalkyl, cycloalkyl, aralkyl, heteroaralkyl, heteroaryl, heterocyclyl, hydroxy, amino, imino, amido or thiol;

$B^1$ is O, S, or $NR^8$;

$B^2$ is $CR^9$ or N;

$R^6$ is hydrogen, halo, cyano, alkyl, alkenyl, alkoxy, aminoalkyl, heteroalkyl, cycloalkyl, aralkyl, heteroaralkyl, aryl, heteroaryl, heterocyclyl, amino, amido or thiol;

$R^7$ is hydrogen, alkyl, alkenyl, heteroalkyl, cycloalkyl, aryl, heteroaryl or heterocyclyl;

$R^8$ is hydrogen, alkyl, alkenyl, heteroalkyl, cycloalkyl, aryl, heteroaryl, or heterocyclyl; and $R^9$ is hydrogen, halo, cyano, alkyl, alkenyl, alkoxy, aminoalkyl, heteroalkyl, cycloalkyl, aralkyl, heteroaralkyl, aryl, heteroaryl, heterocyclyl, amino, amido or thiol;

provided that a compound of formula (I) is not:

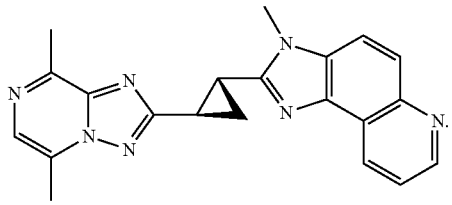 [SMILES: Cc1ncc(C)n2nc([C@@H]3C[C@H]3c3nc4c5cccnc5ccc4n3C)nc12]

2. The compound of claim 1, or a pharmaceutically acceptable salt or stereoisomer thereof, wherein $R^4$ and $R^5$ are each independently hydrogen, cyano, halo, alkyl, alkenyl, alkoxy, aminoalkyl, heteroalkyl, cycloalkyl, aralkyl, heteroaralkyl, heteroaryl, heterocyclyl, hydroxy, amino, imino, amido or thiol.

3. The compound of claim 1, or a pharmaceutically acceptable salt or stereoisomer thereof, wherein $R^4$ and $R^5$ together with the atoms to which they are attached form a monocyclic or multicyclic aryl, heteroaryl, cycloalkyl, or heterocyclyl ring.

4. The compound of claim 3, or a pharmaceutically acceptable salt or stereoisomer thereof, wherein m is 0.

5. The compound of claim 3, or a pharmaceutically acceptable salt or stereoisomer thereof, wherein R is methyl and m is 1 or 2.

6. The compound of claim 3, or a pharmaceutically acceptable salt or stereoisomer thereof, wherein $R^4$ and $R^5$ together form a monocyclic aryl, heteroaryl, cycloalkyl, or heterocyclyl ring and B is a bicyclic ring system.

7. The compound of claim 3, or a pharmaceutically acceptable salt or stereoisomer thereof, wherein $R^4$ and $R^5$ together form a multicyclic aryl, heteroaryl, cycloalkyl, or heterocyclyl ring and B is a tricyclic ring system.

8. The compound of claim 3, or a pharmaceutically acceptable salt or stereoisomer thereof, wherein n is 2.

9. The compound of claim 8, wherein the compound is:

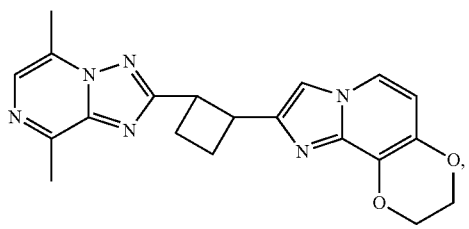

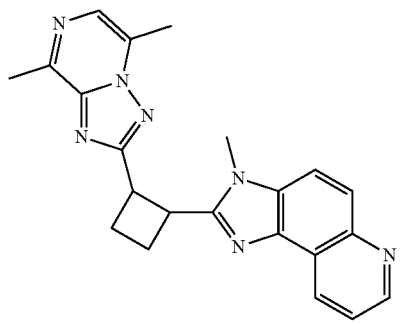

-continued

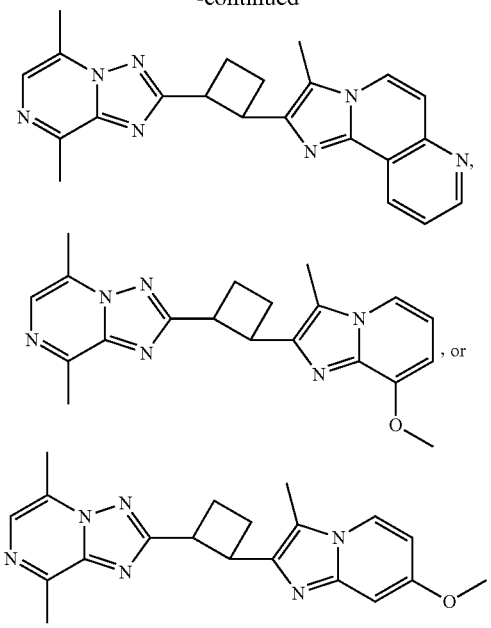

or a pharmaceutically acceptable salt thereof.

10. The compound of claim 3, or a pharmaceutically acceptable salt or stereoisomer thereof, wherein n is 1.

11. The compound of claim 10, or a pharmaceutically acceptable salt or stereoisomer thereof, wherein B is:

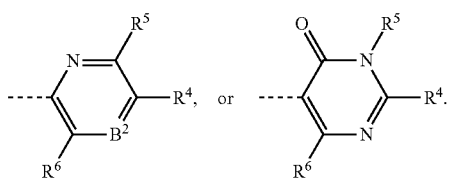

12. The compound of claim 10, or a pharmaceutically acceptable salt or stereoisomer thereof, wherein B is:

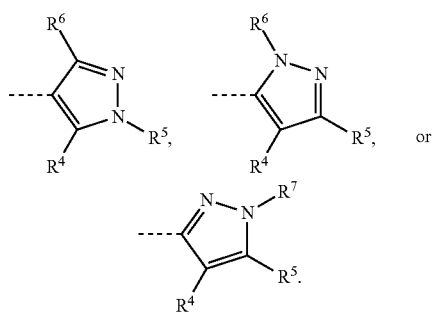

13. The compound of claim 10, having formula:

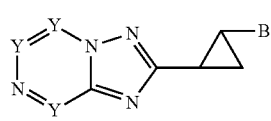

or a pharmaceutically acceptable salt or stereoisomer thereof.

14. The compound of claim 13, or a pharmaceutically acceptable salt or stereoisomer thereof, wherein B is

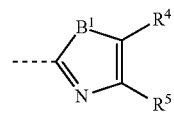

and $B^1$ is $NR^8$.

15. The compound of claim 14, wherein the compound is

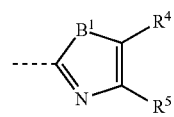

or or pharmaceutically acceptable salt thereof.

16. The compound of claim 13, or a pharmaceutically acceptable salt or stereoisomer thereof, wherein B is

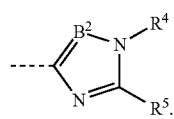

17. The compound of claim 16, or a pharmaceutically acceptable salt or stereoisomer thereof, wherein B is a bicyclic ring system.

18. The compound of claim 17, wherein the compound is:

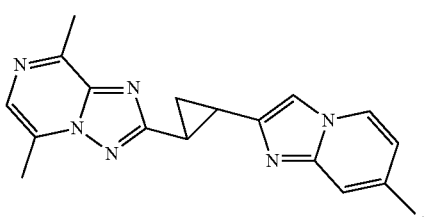

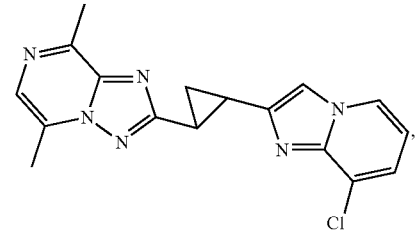

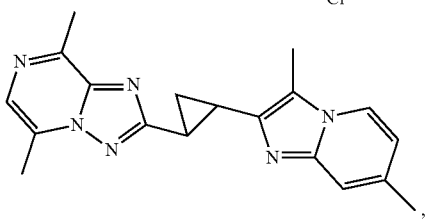

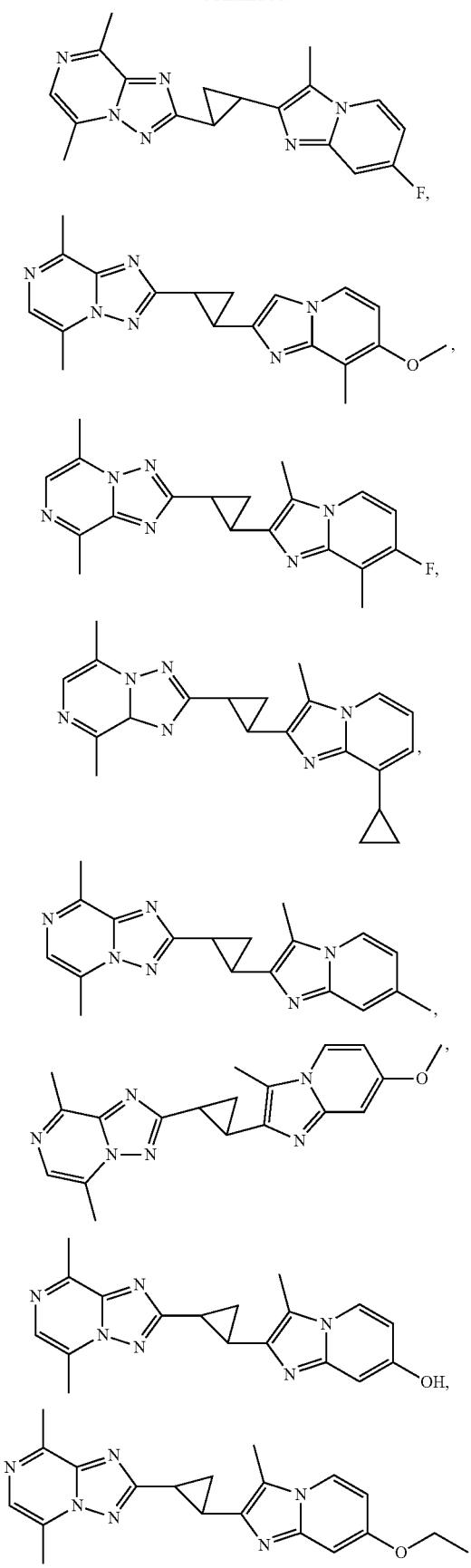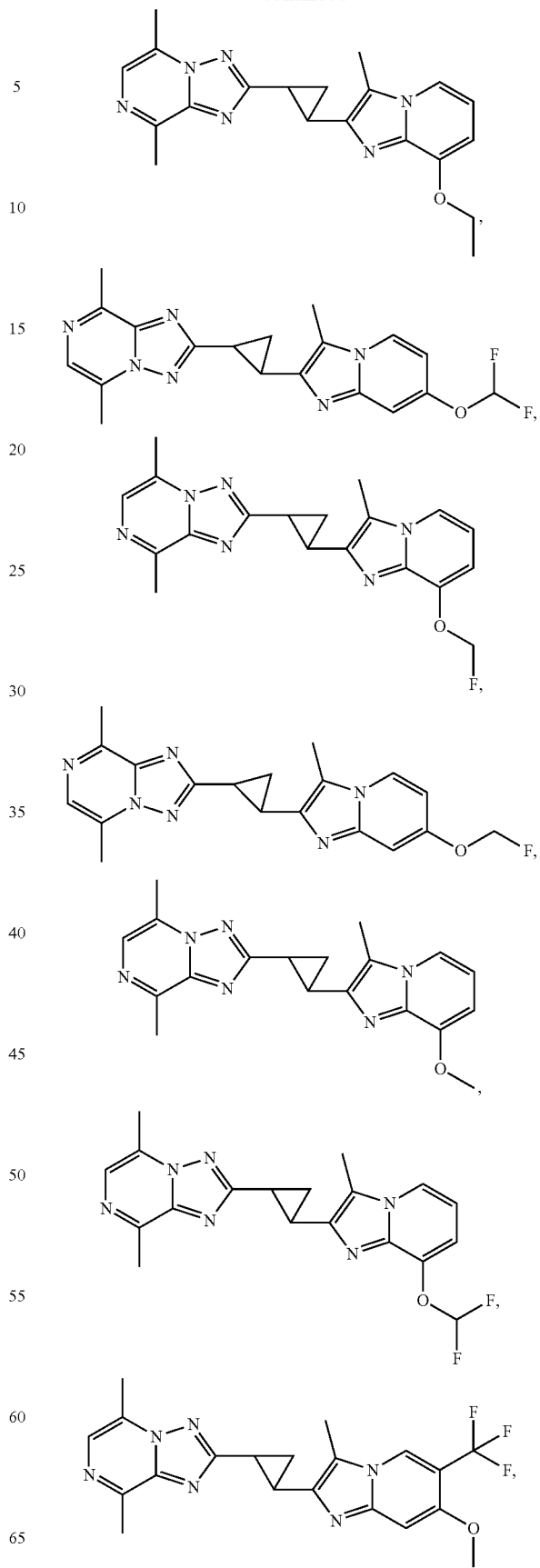

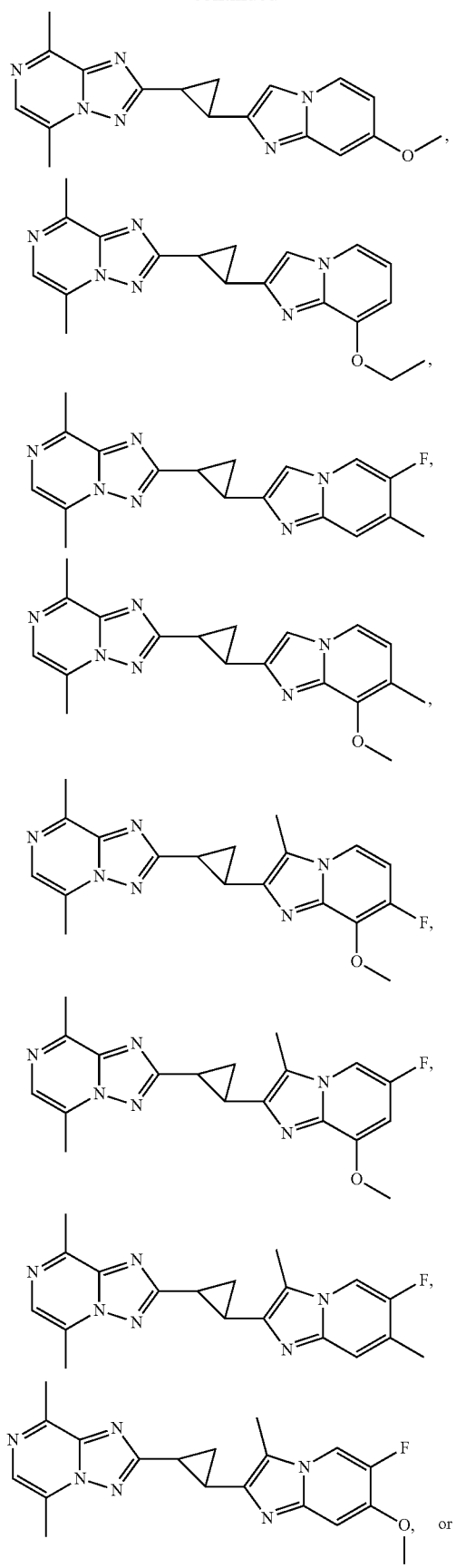
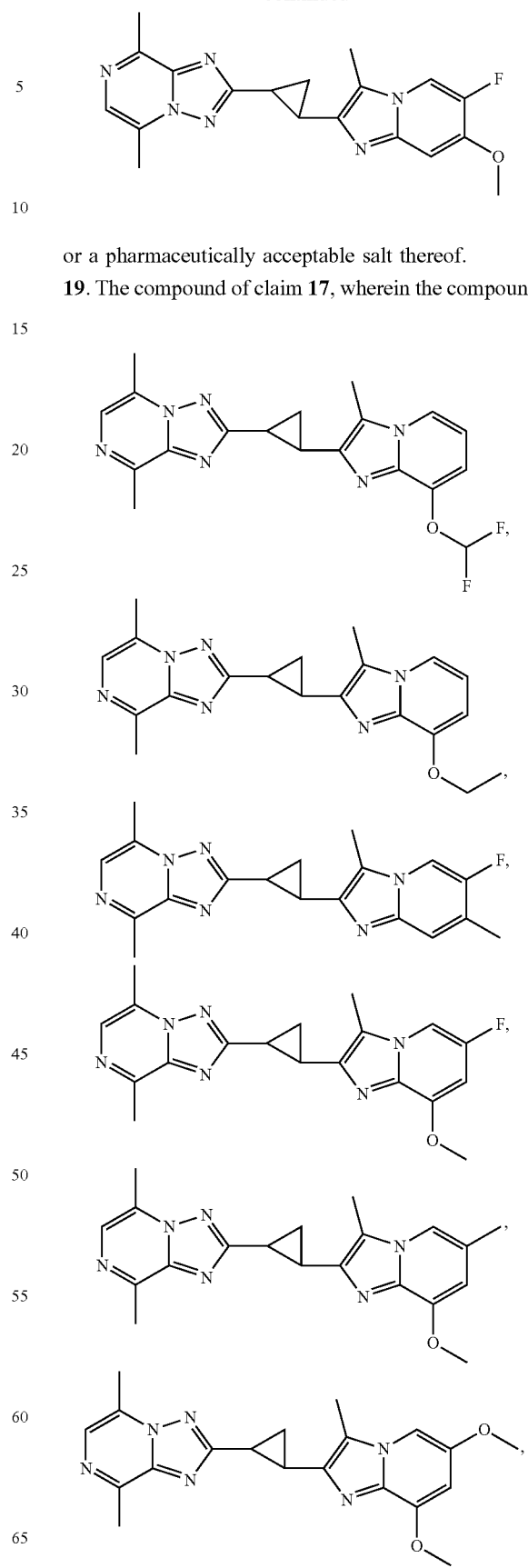
or a pharmaceutically acceptable salt thereof.
19. The compound of claim 17, wherein the compound is:

-continued
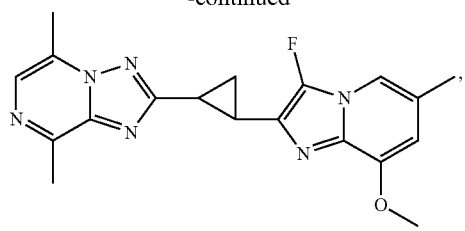
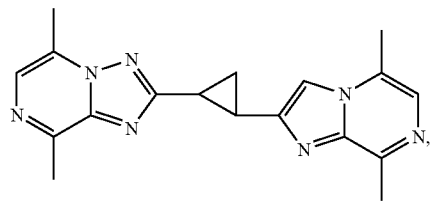
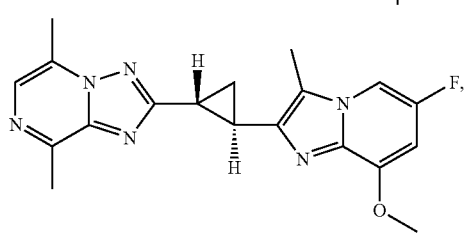
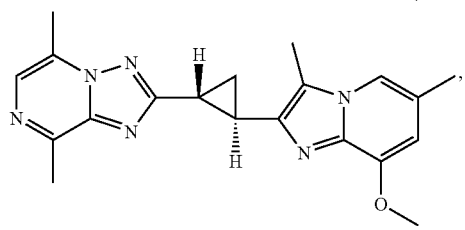
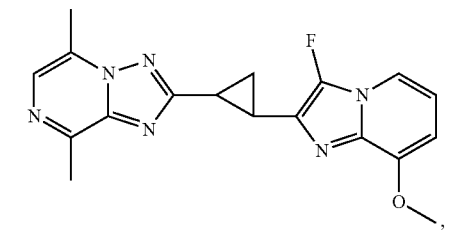
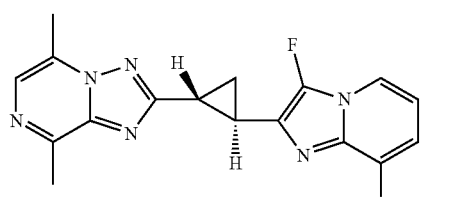
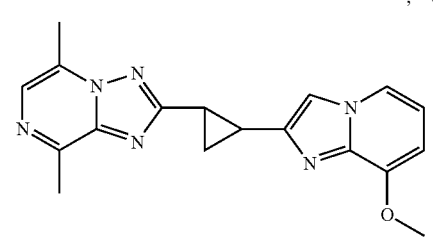
or a pharmaceutically acceptable salt thereof.
20. The compound of claim 16, or a pharmaceutically acceptable salt or stereoisomer thereof, wherein B is a tricyclic ring system.
21. The compound of claim 20, wherein the compound is:
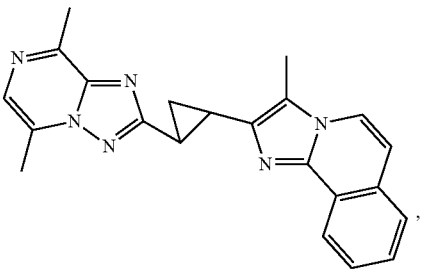
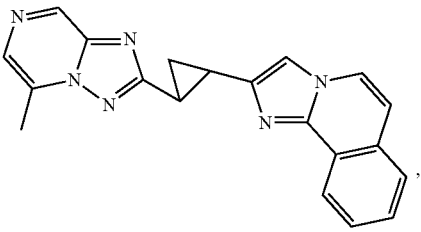
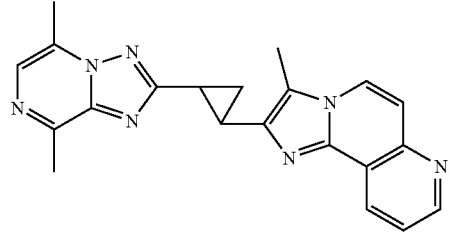
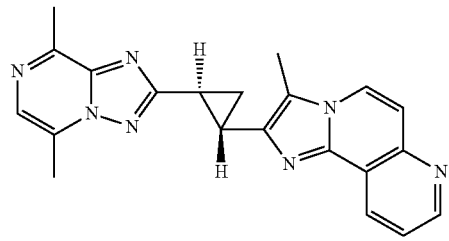
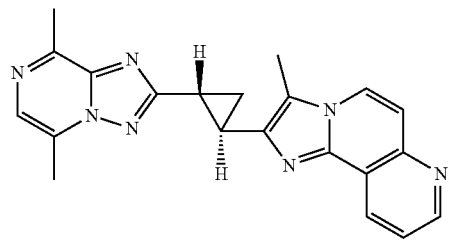
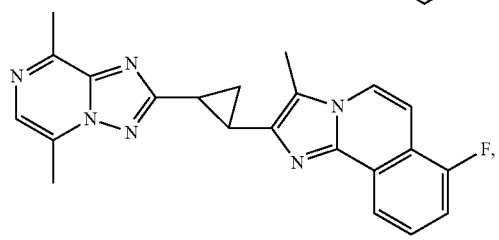
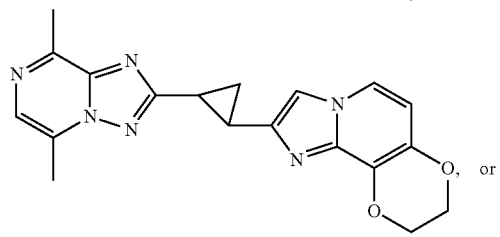
or

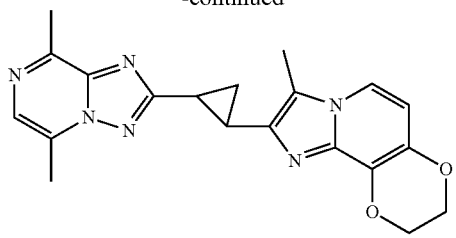

or a pharmaceutically acceptable salt thereof.

22. The compound of claim 20, wherein the compound is:

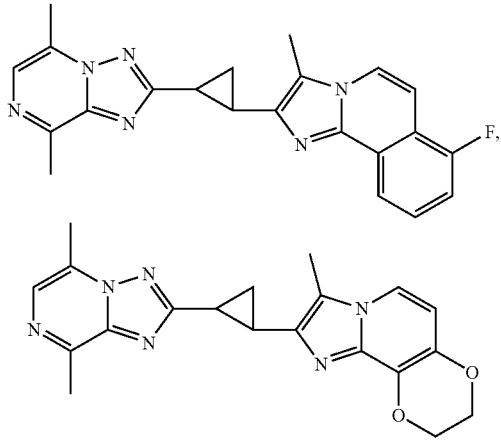

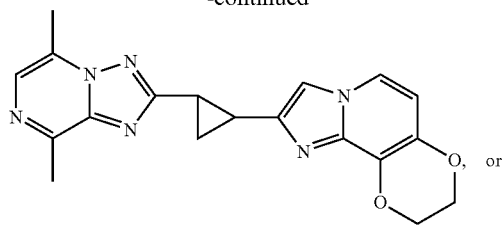

or a pharmaceutically acceptable salt thereof.

23. A pharmaceutical composition comprising a compound of claim 1 or a pharmaceutically acceptable salt or stereoisomer thereof, and a pharmaceutically acceptable excipient, diluent, or carrier.

24. The pharmaceutical composition of claim 23, which further comprises one or more additional active agents.

* * * * *

UNITED STATES PATENT AND TRADEMARK OFFICE
CERTIFICATE OF CORRECTION

PATENT NO. : 9,505,751 B2  
APPLICATION NO. : 14/409866  
DATED : November 29, 2016  
INVENTOR(S) : John Emmerson Campbell, Phillip G. Jones and Scott Malcolm Page 1 of 2

It is certified that error appears in the above-identified patent and that said Letters Patent is hereby corrected as shown below:

At Column 135, Lines 45-50, the chemical structure 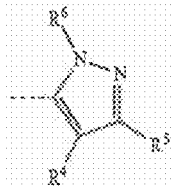 should be replaced with 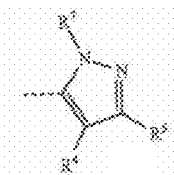

At Column 136, Lines 15-20, the chemical structure 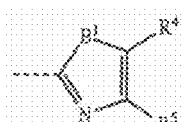 should be replaced with

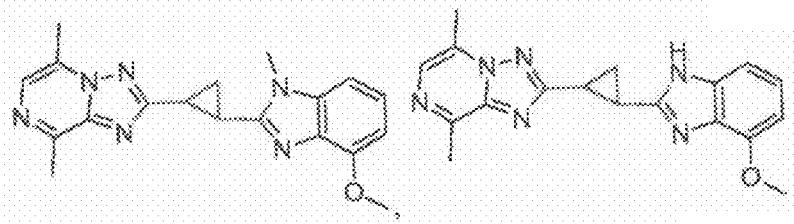

Signed and Sealed this  
Tenth Day of July, 2018

Andrei Iancu  
*Director of the United States Patent and Trademark Office*

CERTIFICATE OF CORRECTION (continued)
U.S. Pat. No. 9,505,751 B2